United States Patent
Kitamura et al.

(10) Patent No.: US 8,735,878 B2
(45) Date of Patent: May 27, 2014

(54) CHARGE TRANSPORTING MATERIAL AND ORGANIC ELECTROLUMINESCENCE DEVICE

(75) Inventors: Tetsu Kitamura, Kanagawa (JP); Toru Watanabe, Kanagawa (JP); Toshihiro Ise, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 161 days.

(21) Appl. No.: 13/518,239

(22) PCT Filed: Dec. 28, 2010

(86) PCT No.: PCT/JP2010/073816
§ 371 (c)(1),
(2), (4) Date: Jun. 21, 2012

(87) PCT Pub. No.: WO2011/086861
PCT Pub. Date: Jul. 21, 2011

(65) Prior Publication Data
US 2012/0256173 A1    Oct. 11, 2012

(30) Foreign Application Priority Data

| Jan. 15, 2010 | (JP) | 2010-007535 |
| May 20, 2010 | (JP) | 2010-116666 |
| Nov. 4, 2010 | (JP) | 2010-247908 |

(51) Int. Cl.
*H01L 35/24*    (2006.01)

(52) U.S. Cl.
USPC .................. 257/40; 257/E51.001

(58) Field of Classification Search
USPC ........................... 257/40, E51.001
See application file for complete search history.

(56) References Cited

U.S. PATENT DOCUMENTS

| 6,617,051 B1 | 9/2003 | Higashi et al. |
| 2004/0007971 A1 | 1/2004 | Higashi et al. |
| 2006/0051613 A1 | 3/2006 | Tomita et al. |
| 2006/0159959 A1 | 7/2006 | Higashi et al. |
| 2007/0104976 A1 | 5/2007 | Iwakuma et al. |
| 2007/0128467 A1 | 6/2007 | Iwakuma et al. |
| 2007/0247063 A1 | 10/2007 | Murase et al. |

FOREIGN PATENT DOCUMENTS

| JP | 2007-063501 A | 3/2007 |
| JP | 2008-147353 A | 6/2008 |
| JP | 2008-084913 A | 10/2008 |
| JP | 2009-218547 A | 9/2009 |
| JP | 2010-087488 A | 4/2010 |
| WO | 00/41443 A1 | 7/2000 |
| WO | 2004/074399 A1 | 9/2004 |
| WO | 2005/057987 A1 | 6/2005 |
| WO | 2005/063920 A1 | 7/2005 |
| WO | 2005/113531 A1 | 12/2005 |

OTHER PUBLICATIONS

International Search Report for PCT/JP2010/073816 dated Mar. 22, 2011, 2010 [PCT/ISA/210].
Communication from the Japanese Patent Office dated Aug. 10, 2010, in a counterpart application No. 2010-116666.

*Primary Examiner* — Anthony Ho
(74) *Attorney, Agent, or Firm* — Morgan Lewis & Bockius LLP

(57) ABSTRACT

In order to provide an organic electroluminescence device with high luminous efficiency and good durability, the present invention provides a charge transporting material including a compound represented by Formula (Cz-1) wherein the content of a particular halogen-containing impurity in the charge transporting material is from 0.000% to 0.10% when the content is calculated as a proportion of the absorption intensity area of the impurity with respect to the total absorption intensity area of the charge transporting material, as measured by high-performance liquid chromatography at a measurement wavelength of 254 nm, and an organic electroluminescence device wherein the charge transporting material is included in an organic layer:

Formula (Cz-1)
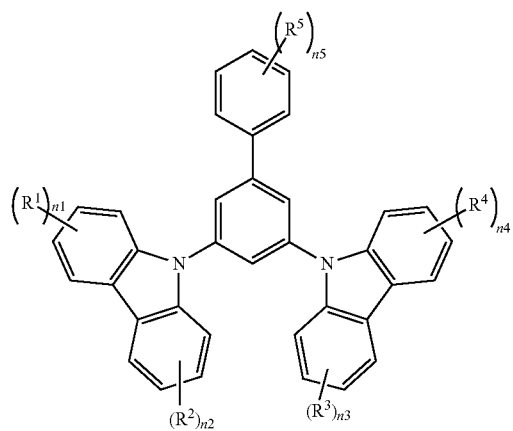
wherein in Formula (Cz-1), each of $R^1$ to $R^5$ independently represents a particular atom or group; and each of n1 to n5 independently represents a particular integer.
15 Claims, 1 Drawing Sheet

US 8,735,878 B2

CHARGE TRANSPORTING MATERIAL AND ORGANIC ELECTROLUMINESCENCE DEVICE

TECHNICAL FIELD

The present invention relates to a charge transporting material and an organic electroluminescence device.

BACKGROUND ART

Research and development is being actively performed on organic electroluminescence devices (hereinafter, also referred to as "devices" or "organic EL devices") due to their ability to emit light with high luminance intensity at low driving voltages. An organic electroluminescence device has a pair of electrodes and an organic layer therebetween in which electrons injected from the cathode recombine with holes injected from the anode in the organic layer to create excitons whose energy is utilized for light emission.

Phosphorescent materials are currently used to achieve high efficiency of devices. Further, dope-type devices using light emitting layers in which host materials are doped with light emitting materials are widely employed.

Host materials are also being developed. For example, Patent Document 1 discloses a 1,3-bis(N-carbazolyl)benzene (mCP) derivative substituted with a phenyl group for the purpose of fabricating a device with high luminous efficiency, few pixel defects and good heat resistance. The patent document also discloses an organic electroluminescence device using the derivative as a host material.

However, there is still a need for organic electroluminescence devices whose luminous efficiency and durability are compatible with each other at a higher level than the device described in Patent Document 1.

Patent Document 2 discloses an organic EL device which includes at least one organic compound layer composed of an organic compound material having an impurity concentration below 1,000 ppm thereby improving durability of a device. However, Patent Document 2 fails to specify the kind of impurities that have a great influence on the performance of the device.

Further, Patent Document 3 discloses organic EL devices using, as host materials, various N-carbazolylbenzene derivatives having a purity of 99.3% to 99.9%, as analyzed by high-performance liquid chromatography (HPLC). However, Patent Document 3 also fails to specify the kind of impurities that have a great influence on the performance of the devices.

RELATED ART

Patent Document

Patent Document 1: International Publication No. 04/074399
Patent Document 2: International Publication No. 00/41443
Patent Document 3: International Publication No. 05/063920

DISCLOSURE OF INVENTION

Problems to be Solved by the Invention

Generally, a certain organic compound material contains a plurality of halogen-containing impurities, but not all of them give the same influence on the durability of an organic electroluminescence device using the organic compound material, and it is impossible to simply know what structures of the halogen-containing impurities give a great influence on the durability of the device.

Improvements in the performance of devices resulting from a reduction of unspecified impurities have already been reported in the literature, including Patent Document 2, but depending on the structure of charge transporting materials, kinds of impurities giving an influence on the device performance vary. Not all impurities contained in organic compound materials give an influence to the same extent on the performance of devices and the kind of impurities giving a great influence on the performance of devices may vary depending on the structure of materials or the intended purpose of use thereof (for example, depending on the layers of devices that the materials are used). It has been found that a reduction in the content of a trace bromo compound having a particular structure in a charge transporting material of the present invention leads to a considerable improvement in durability, and other impurities having different structures do not give an influence on the durability even though they are bromo compounds.

An object of the invention is to provide an organic electroluminescence device with high luminous efficiency and good durability that uses an mCP derivative substituted with a phenyl group while specifying the kind of impurity species giving a bad influence on the performance of the device.

Another object of the invention is to provide a charge transporting material suitable for use in the fabrication of an organic electroluminescence device with high luminous efficiency and good durability. Another object of the invention is to provide a light emission apparatus, a display apparatus and an illumination apparatus, each of which includes the organic electroluminescence device of the present invention.

Means for Solving the Problems

As a result of a review, the present inventors have been found that an impurity compound having a particular structure present in a 1,3-bis(N-carbazolyl)benzene (mCP) derivative substituted with a phenyl group as a charge transporting material gives a great influence on the performance of a device, and that when the content of the corresponding impurity is reduced, luminous efficiency and durability can be compatible with each other at a high level.

That is, the present invention can be accomplished by the following features.

[1] A charge transporting material, comprising:
a compound represented by Formula (Cz-1),
wherein a content of an impurity represented by Formula (I-1) in the charge transporting material is from 0.000% to 0.10% when the content is calculated as a proportion of an absorption intensity area of the impurity represented by Formula (I-1) with respect to a total absorption intensity area of the charge transporting material, as measured by high-performance liquid chromatography at a measurement wavelength of 254 nm:

Formula (Cz-1)

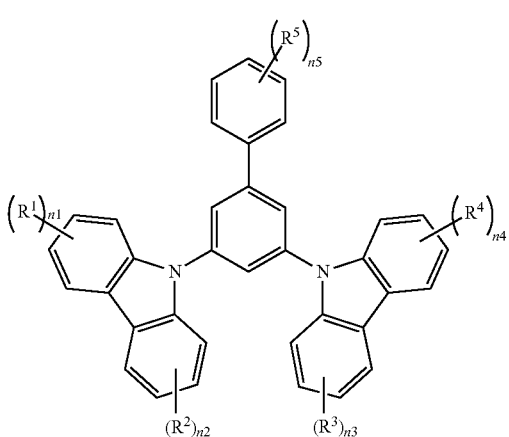

wherein in Formula (Cz-1), each of $R^1$ to $R^4$ independently represents a fluorine atom, an alkyl group, an aryl group, a silyl group or a cyano group, provided that when $R^1$ to $R^4$ respectively exist in plurality, a plurality of $R^1$'s to a plurality of $R^4$'s may be the same or different respectively;

$R^5$ represents an alkyl group, an aryl group or a silyl group, provided that $R^5$ does not represent a carbazolyl group or a perfluoroalkyl group, and when $R^5$ exists in plurality, a plurality of $R^5$'s may be the same or different or a plurality of $R^5$'s may be bonded together to form an aryl ring;

each of n1 to n4 independently represents an integer from 0 to 4; and n5 represents an integer from 0 to 5:

Formula (I-1)

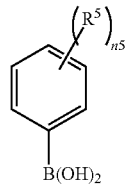

wherein in Formula (I-1), $R^1$ to $R^4$ are the same atoms or groups as defined for $R^1$ to $R^4$ in Formula (Cz-1) respectively; and n1 to n4 are the same integers as defined for n1 to n4 in Formula (Cz-1) respectively.

[2] The charge transporting material as described in [1] above, wherein a proportion of a sum of absorption intensity areas of the compound represented by Formula (Cz-1), the impurity represented by Formula (I-1), an impurity represented by Formula (II-1) and 1,3,5-tribromobenzene with respect to the total absorption intensity area of the charge transporting material, as measured by high-performance liquid chromatography at a measurement wavelength of 254 nm, is 100%:

Formula (II-1)

wherein in Formula (II-1), $R^5$ is the same group as defined for $R^5$ in Formula (Cz-1); and n5 is the same integer as defined for n5 in Formula (Cz-1).

[3] The charge transporting material as described in [1] or [2] above, wherein the compound represented by Formula (Cz-1) is represented by Formula (Cz-2) and the impurity represented by Formula (I-1) is represented by Formula (I-2):

Formula (Cz-2)

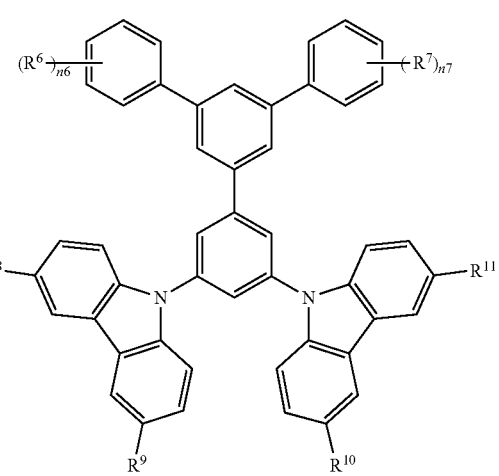

wherein in Formula (Cz-2), each of $R^8$ to $R^{11}$ independently represents a hydrogen atom, a fluorine atom, an alkyl group, an aryl group, a silyl group or a cyano group;

each of $R^6$ and $R^7$ independently represents an alkyl group, an aryl group, a cyano group or a fluorine atom, provided that when $R^6$ and $R^7$ respectively exist in plurality, a plurality of $R^6$'s and a plurality of $R^7$'s may be the same or different respectively or a plurality of $R^6$'s and a plurality of $R^7$'s may be bonded together to form an aryl ring that may have an alkyl group respectively; and each of n6 and n7 independently represents an integer from 0 to 5:

Formula (I-2)

wherein in Formula (I-2), $R^8$ to $R^{11}$ are the same atoms or groups as defined for $R^8$ to $R^{11}$ in Formula (Cz-2) respectively.

[4] The charge transporting material as described in [3] above, wherein a proportion of a sum of absorption intensity areas of the compound represented by Formula (Cz-2), the impurity represented by Formula (I-2), an impurity represented by Formula (II-2) and 1,3,5-tribromobenzene with respect to the total absorption intensity area of the charge transporting material, as measured by high-performance liquid chromatography at a measurement wavelength of 254 nm, is 100%:

Formula (II-2)

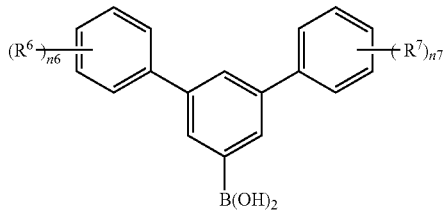

wherein in Formula (II-2), $R^6$ and $R^7$ are the same atoms or groups as defined for $R^6$ and $R^7$ in Formula (Cz-2) respectively; and n6 and n7 are the same integers as defined for n6 and n7 in Formula (Cz-2) respectively.

[5] The charge transporting material as described in [3] or [4] above, wherein in Formulae (Cz-2) and (II-2), $R^6$ and $R^7$ represent phenyl groups and each of n6 and n7 independently represents 0 or 1, and in Formulae (Cz-2) and (I-2), each of $R^8$ to $R^{11}$ independently represents a hydrogen atom, a t-butyl group, a phenyl group, a trimethylsilyl group or a triphenylsilyl group.

[6] A composition, comprising:
the charge transporting material as described in any one of [1] to [5] above.

[7] A thin film, comprising:
the charge transporting material as described in any one of [1] to [5] above.

[8] An organic electroluminescence device, comprising on a substrate:
a pair of electrodes; and
at least one layer of an organic layer including a light emitting layer between the electrodes,
wherein any layer of the at least one layer of an organic layer contains the charge transporting material as described in any one of [1] to [5] above.

[9] The organic electroluminescence device as described in [8] above,
wherein the light emitting layer contains the charge transporting material.

[10] The organic electroluminescence device as described in [8] or [9] above,
wherein at least one layer of the organic layer between the pair of electrodes is formed by a solution coating method.

[11] A light emission apparatus using the organic electroluminescence device as described in any one of [8] to [10] above.

[12] A display apparatus using the organic electroluminescence device as described in any one of [8] to [10] above.

[13] An illumination apparatus using the organic electroluminescence device as described in any one of [8] to [10] above.

Effects of the Invention

According to the present invention, an organic electroluminescence device with high luminous efficiency and good durability can be provided.

EMBODIMENTS FOR CARRYING OUT THE INVENTION

Figure 1:
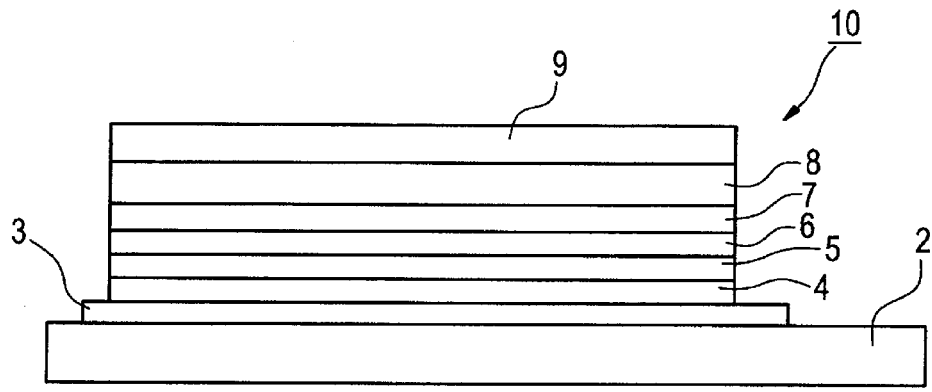
FIG. 1 is a schematic view illustrating an exemplary construction of an organic electroluminescence device according to the present invention.

In the present invention, the group A of substituents, the group B of substituents and substituent Z' are defined as follows.

(Group A of Substituents)

Examples include alkyl groups (having preferably 1 to 30 carbon atoms, more preferably 1 to 20 carbon atoms, and particularly preferably 1 to 10 carbon atoms, and examples thereof include methyl, ethyl, isopropyl, t-butyl, n-octyl, n-decyl, n-hexadecyl, cyclopropyl, cyclopentyl, cyclohexyl and the like), alkenyl groups (having preferably 2 to 30 carbon atoms, more preferably 2 to 20 carbon atoms, and particularly preferably 2 to 10 carbon atoms, and examples thereof include vinyl, allyl, 2-butenyl, 3-pentenyl and the like), alkynyl groups (having preferably 2 to 30 carbon atoms, more preferably 2 to 20 carbon atoms, and particularly preferably 2 to 10 carbon atoms, and examples thereof include propargyl, 3-pentynyl and the like), aryl groups (having preferably 6 to 30 carbon atoms, more preferably having 6 to 20 carbon atoms, and particularly preferably 6 to 12 carbon atoms, and examples thereof include phenyl, p-methylphenyl, naphthyl, anthranyl and the like), amino groups (having preferably 0 to 30 carbon atoms, more preferably 0 to 20 carbon atoms, and particularly preferably 0 to 10 carbon atoms, and examples thereof include amino, methylamino, dimethylamino, diethylamino, dibenzylamino, diphenylamino, ditolylamino and the like), alkoxy groups (having preferably 1 to 30 carbon atoms, more preferably 1 to 20 carbon atoms, and particularly preferably 1 to 10 carbon atoms, and examples thereof include methoxy, ethoxy, butoxy, 2-ethylhexyloxy and the like), aryloxy groups (having preferably 6 to 30 carbon atoms, more preferably 6 to 20 carbon atoms, and particularly preferably 6 to 12 carbon atoms, and examples thereof include phenyloxy, 1-naphthyloxy, 2-naphthyloxy and the like), heterocyclic oxy groups (having preferably 1 to 30 carbon atoms, more preferably 1 to 20 carbon atoms, and particularly preferably 1 to 12 carbon atoms, and examples thereof include pyridyloxy, pyradyloxy, pyrimidyloxy, quinolyloxy and the like), acyl groups (having preferably 2 to 30 carbon atoms, more preferably 2 to 20 carbon atoms, and particularly preferably 2 to 12 carbon atoms, and examples thereof include acetyl, benzoyl, formyl, pivaroyl and the like), alkoxycarbonyl groups (having preferably 2 to 30 carbon atoms, more preferably 2 to 20 carbon atoms, and particularly preferably 2 to 12 carbon atoms, and examples thereof include methoxycarbonyl, ethoxycarbonyl and the like), aryloxycarbonyl groups (having preferably 7 to 30 carbon atoms, more preferably 7 to 20 carbon atoms, and particularly preferably 7 to 12 carbon atoms, and examples thereof include phenyloxycarbonyl and the like), acyloxy groups (having preferably 2 to 30 carbon atoms, more preferably 2 to 20 carbon atoms, and particularly preferably 2 to 10 carbon atoms, and examples thereof include acetoxy, benzoyloxy and the like), acylamino groups (having 2 to 30 carbon atoms, more preferably 2 to 20 carbon atoms, and particularly preferably 2 to 10 carbon atoms, and examples thereof include acetylamino, benzoylamino and the like), alkoxycarbonylamino groups (having preferably 2 to 30 carbon atoms, more preferably 2 to 20 carbon atoms, and particularly preferably 2 to 12 carbon atoms, and examples thereof include methoxycarbonylamino and the like), aryloxycarbonylamino groups (having preferably 7 to 30 carbon atoms, more preferably 7 to 20 carbon atoms, and particularly preferably 7 to 12 carbon atoms, and examples thereof include phenyloxycarbonylamino and the like), sulfonylamino groups (having preferably 1 to 30 carbon atoms, more preferably 1 to 20 carbon atoms, and particularly preferably 1 to 12 carbon atoms, and examples thereof include methanesulfonylamino, benzenesulfonylamino and the like), sulfamoyl groups (having preferably 0 to 30 carbon atoms, more preferably 0 to 20 carbon atoms, and particularly preferably 0 to 12 carbon atoms, and examples thereof include sulfamoyl, methylsulfamoyl, dimethylsulfamoyl, phenylsulfamoyl and the like), carbamoyl groups (having preferably 1 to 30 carbon atoms, more preferably 1 to 20 carbon atoms, and particularly preferably 1 to 12 carbon atoms, and examples thereof include carbamoyl, methylcarbamoyl, diethylcarbamoyl, phenylcarbamoyl and the like), alkylthio groups (having preferably 1 to 30 carbon atoms, more preferably 1 to 20 carbon atoms, and particularly preferably 1 to 12 carbon atoms, and examples thereof include methylthio, ethylthio and the like), arylthio groups (having preferably 6 to 30 carbon atoms, more preferably 6 to 20 carbon atoms, and particularly preferably 6 to 12 carbon atoms, and examples thereof include phenylthio and the like), heterocyclic thio groups (having preferably 1 to 30 carbon atoms, more preferably 1 to 20 carbon atoms, and particularly preferably 1 to 12 carbon atoms, and examples thereof include pyridylthio, 2-benzimizolylthio, 2-benzoxazolylthio, 2-benzthiazolylthio and the like), sulfonyl groups (having preferably 1 to 30 carbon atoms, more preferably 1 to 20 carbon atoms, and particularly preferably 1 to 12 carbon atoms, and examples thereof include mesyl, tosyl and the like), sulfinyl groups (having preferably 1 to 30 carbon atoms, more preferably 1 to 20 carbon atoms, and particularly preferably 1 to 12 carbon atoms, and examples thereof include methanesulfinyl, benzenesulfinyl and the like), ureido groups (having preferably 1 to 30 carbon atoms, more preferably 1 to 20 carbon atoms, and particularly preferably 1 to 12 carbon atoms, and examples thereof include ureido, methylureido, phenylureido and the like), phosphoric acid amide groups (having preferably 1 to 30 carbon atoms, more preferably 1 to 20 carbon atoms, and particularly preferably 1 to 12 carbon atoms, and examples thereof include diethylphosphoric acid amide, phenylphosphoric acid amide and the like), hydroxyl groups, mercapto groups, halogen atoms (for example, fluorine atom, chlorine atom, bromine atom and iodine atom), cyano group, sulfo group, carboxyl group, nitro group, hydroxamic acid group, sulfino group, hydrazino group, imino group, heterocyclic groups (also including aromatic heterocyclic groups, and having preferably 1 to 30 carbon atoms, more preferably 1 to 12 carbon atoms, in which the heteroatoms may include, for example, nitrogen atom, oxygen atom, sulfur atom, phosphorus atom, silicon atom, selenium atom and tellurium atom, and examples thereof include, specifically, pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, carbazolyl, azepinyl, silolyl groups and the like), silyl groups (having preferably 3 to 40 carbon atoms, more preferably 3 to 30 carbon atoms, and particularly preferably 3 to 24 carbon atoms, and examples thereof include trimethylsilyl, triphenylsilyl and the like), silyloxy groups (having preferably 3 to 40 carbon atoms, more preferably 3 to 30 carbon atoms, and particularly preferably 3 to 24 carbon atoms, and examples thereof include trimethylsilyloxy, triphenylsilyloxy and the like), and phosphoryl groups (examples thereof include a diphenylphosphoryl group, a dimethylphosphoryl group and the like). These substituents may be additionally substituted, and the additional substituents may include a group selected from the group A of substituents. The substituents additionally substituted with substituents may be further substituted, and the further substituents may include a group selected from the group A of substituents. The substituents additionally substituted with substituents further substituted with substituents may be further substituted, and the further substituents may include a group selected from the group A of substituents.

(Group B of Substituents)

Examples include alkyl groups (having preferably 1 to 30 carbon atoms, more preferably 1 to 20 carbon atoms, and particularly preferably 1 to 10 carbon atoms, and examples thereof include methyl, ethyl, isopropyl, t-butyl, n-octyl, n-decyl, n-hexadecyl, cyclopropyl, cyclopentyl, cyclohexyl and the like), alkenyl groups (having preferably 2 to 30 carbon atoms, more preferably 2 to 20 carbon atoms, and particularly preferably 2 to 10 carbon atoms, and examples thereof include vinyl, allyl, 2-butenyl, 3-pentenyl and the like), alkynyl groups (having preferably 2 to 30 carbon atoms, more preferably 2 to 20 carbon atoms, and particularly preferably 2 to 10 carbon atoms, and examples thereof include propargyl, 3-pentynyl and the like), aryl groups (having preferably 6 to 30 carbon atoms, more preferably 6 to 20 carbon atoms, and particularly preferably 6 to 12 carbon atoms, and examples thereof include phenyl, p-methylphenyl, naphthyl, anthranyl and the like), cyano group, and heterocyclic groups (also including aromatic heterocyclic group, and having preferably 1 to 30 carbon atoms, more preferably 1 to 12 carbon atoms in which the heteroatoms may include, for example, a nitrogen atom, an oxygen atom, a sulfur atom, a phosphorus atom, a silicon atom, a selenium atom and a tellurium atom, and examples thereof include, specifically, pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, carbazolyl, azepinyl, silolyl groups and the like). These substituents may be additionally substituted, and the additional substituents may include a group selected from the group B of substituents. The substituents additionally substituted with substituents may be further substituted, and the further substituents may include a selected from the group B of substituents. The substituents additionally substituted with substituents further substituted with substituents may be further substituted, and the further substituents may include a group selected from the group B of substituents.

(Substituent Z')

Substituent Z' represents an alkyl group, an aryl group or an aromatic heterocyclic group. Substituent Z' is preferably an alkyl group having 1 to 6 carbon atoms, an aryl group having 6 to 18 carbon atoms or an aromatic heterocyclic group having 5 to 10 carbon atoms.

In the following descriptions of Formulas (Cz-1), (Cz-2), (C-1) to (C-7) and (T-1), hydrogen atoms are intended to include isotopes thereof (such as deuterium atoms), and additionally, atoms constituting substituents are also intended to include isotopes thereof.

An organic electroluminescence device of the present invention includes on a substrate a pair of electrodes and at least one layer of an organic layer including a light emitting layer between the electrodes wherein any constituent layer of the at least one layer of an organic layer includes a charge transporting material of the present invention. The charge transporting material of the present invention includes a compound represented by Formula (Cz-1) wherein the content of an impurity represented by Formula (I-1) in the charge transporting material is from 0.000% to 0.10% when the content is calculated as a proportion of the absorption intensity area of the impurity represented by Formula (I-1) with respect to the total absorption intensity area of the charge transporting material, as measured by high-performance liquid chromatography at a measurement wavelength of 254 nm.

[Charge Transporting Material]

Hereinafter, an explanation will be given of the charge transporting material including the compound represented by Formula (Cz-1).

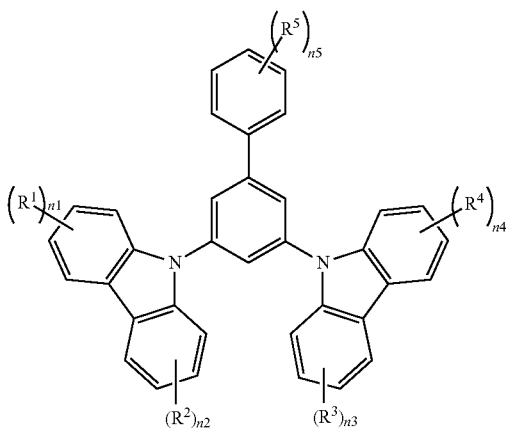

Formula (Cz-1)

In Formula (Cz-1), each of $R^1$ to $R^4$ independently represents a fluorine atom, an alkyl group, an aryl group, a silyl group or a cyano group. When $R^1$ to $R^4$ respectively exist in plurality, a plurality of $R^1$'s to a plurality of $R^4$'s may be the same or different respectively.

$R^5$ represents an alkyl group, an aryl group or a silyl group, provided that $R^5$ does not represent a carbazolyl group or a perfluoroalkyl group. When $R^5$ exists in plurality, a plurality of $R^5$'s may be the same or different. A plurality of $R^5$'s may be bonded together to form an aryl ring.

Each of n1 to n4 independently represents an integer from 0 to 4.

n5 represents an integer from 0 to 5.

The alkyl groups represented by $R^1$ to $R^4$ are preferably alkyl groups that may have a fluorine atom, more preferably $C_1$-$C_6$ alkyl groups that may have a fluorine atom, even more preferably $C_1$-$C_4$ alkyl groups that may have a fluorine atom, and among these, unsubstituted alkyl groups are preferred. Examples thereof include a methyl group, a trifluoromethyl group, an ethyl group, a n-propyl group, an isopropyl group, a n-butyl group, an isobutyl group, a sec-butyl group, a t-butyl group, a n-pentyl group, an isopentyl group, a 2-methylpentyl group, a neopentyl group, a n-hexyl group, a 4-methylpentyl group, a 3-methylpentyl group, a 2-methylpentyl group, a 2-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group and the like, and among these, a methyl group, a trifluoromethyl group, an isopropyl group, a t-butyl group or a neopentyl group is preferred, and a t-butyl group is more preferred.

The aryl groups represented by $R^1$ to $R^4$ are preferably aryl groups that may have an alkyl group, more preferably $C_6$-$C_{18}$ aryl groups that may have a $C_1$-$C_6$ alkyl group, even more preferably $C_6$-$C_{12}$ aryl groups that may have a $C_1$-$C_4$ alkyl group. Examples thereof include a phenyl group, a dimethylphenyl group, a biphenyl group, a terphenyl group, a naphthyl group, a methylnaphthyl group, a t-butylnaphthyl group, an anthranyl group, a phenanthryl group, a chrysenyl group and the like, and among these, a phenyl group, a dimethylphenyl group or a terphenyl group is preferred, and a phenyl group is more preferred.

The silyl groups represented by $R^1$ to $R^4$ may have a substituent. In the case of having a substituent, the substituent may be substituent Z' as described above, substituent Z' may be preferably an alkyl group or an aryl group, more preferably a methyl group or a phenyl group, most preferably a phenyl group.

The silyl groups represented by $R^1$ to $R^4$ are preferably $C_3$-$C_{18}$ silyl groups, more preferably $C_3$-$C_{18}$ silyl groups. The $C_3$-$C_{18}$ silyl groups are preferably $C_3$-$C_{18}$ silyl groups that are substituted with a $C_1$-$C_6$ alkyl group or an aryl group, more preferably those in which the three hydrogen atoms of the silyl group are wholly replaced by either of $C_1$-$C_6$ alkyl groups and aryl groups, even more preferably silyl groups in which the three hydrogen atoms of the silyl group are wholly replaced by phenyl groups. Examples thereof include a trimethylsilyl group, a triethylsilyl group, a t-butyldimethylsilyl group, a diethylisopropylsilyl group, a dimethylphenylsilyl group, a diphenylmethylsilyl group, a triphenylsilyl group and the like, and among these, a trimethylsilyl group, a dimethylphenylsilyl group or a triphenylsilyl group is preferred, and a triphenylsilyl group is more preferred.

From the viewpoint of charge transportability and stability against charges, it is preferred that each of $R^1$ to $R^4$ is independently selected from fluorine atom, $C_1$-$C_6$ alkyl groups that may have a fluorine atom, $C_6$-$C_{18}$ aryl groups that may have a $C_1$-$C_6$ alkyl group, $C_3$-$C_{18}$ silyl groups that may be substituted with a $C_1$-$C_6$ alkyl group or a phenyl group and cyano group, more preferably selected from fluorine atom, $C_1$-$C_4$ alkyl groups that may have a fluorine atom, $C_6$-$C_{12}$ aryl groups that may have a $C_1$-$C_4$ alkyl group, $C_3$-$C_{18}$ silyl groups that may be substituted with a $C_1$-$C_4$ alkyl group or a phenyl group and cyano group.

Among these, each of $R^1$ to $R^4$ is independently preferably selected from a methyl group, an isopropyl group, a t-butyl group, a neopentyl group, a trifluoromethyl group, a phenyl group, a dimethylphenyl group, a trimethylsilyl group, a triphenylsilyl group, a fluorine atom and a cyano group, more preferably selected from a t-butyl group, a phenyl group, a trimethylsilyl group and a triphenylsilyl group, even more preferably selected from a t-butyl group, a phenyl group and a triphenylsilyl group.

Each of n1 to n4 is independently preferably an integer from 0 to 2, more preferably 0 or 1. When the substituents are introduced into the carbazol structures, the 3- and 6-positions of the carbazol structures are reactive active sites, and it is preferred to introduce the substituents into the 3- and 6-positions of the carbazol structures from the viewpoint of ease of synthesis and chemical stability.

The alkyl group represented by $R^5$ is preferably a $C_1$-$C_6$ alkyl group, more preferably a $C_1$-$C_4$ alkyl group. However, the alkyl group represented by $R^5$ is not a perfluoroalkyl group. Examples thereof include a methyl group, an ethyl group, an n-propyl group, an isopropyl group, a n-butyl group, an isobutyl group, a sec-butyl group, a t-butyl group, a n-pentyl group, an isopentyl group, a 2-methylpentyl group, a neopentyl group, a n-hexyl group, a 4-methylpentyl group, a 3-methylpentyl group, a 2-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group and the like, and among these, a methyl group, an isopropyl group, a t-butyl group or a neopentyl group is preferred, a methyl group or a t-butyl group is more preferred, and a t-butyl group is even more preferred.

The aryl group represented by $R^5$ is preferably a $C_6$-$C_{18}$ aryl group that may have a $C_1$-$C_6$ alkyl group optionally substituted with a fluorine atom, a fluorine atom or a cyano group, more preferably a $C_6$-$C_{18}$ aryl group that may have a $C_1$-$C_4$ alkyl group. Examples thereof include a phenyl group, a dimethylphenyl group, a biphenyl group, a terphenyl group, a naphthyl group, a methylnaphthyl group, a t-butylnaphthyl group, an anthranyl group, a phenanthryl group, a chrysenyl group, a cyanophenyl group, a trifluoromethylphenyl group, a fluorinated phenyl group and the like, and among these, a phenyl group, a biphenyl group, a terphenyl group, a naphthyl group, a methylnaphthyl group or a t-butylnaphthyl group is preferred, and a phenyl group, a biphenyl group or a terphenyl group is more preferred.

Specific examples and preferred examples of the silyl group represented by $R^5$ are the same as those of the silyl groups represented by $R^1$ to $R^4$.

When $R^5$ exists in plurality, a plurality of $R^5$'s may be the same or different. A plurality of $R^5$'s may be bonded together to form an aryl ring.

The aryl ring formed by the bonding of a plurality of $R^5$'s is preferably a $C_6$-$C_{30}$ aryl ring, more preferably a $C_6$-$C_{14}$ aryl ring, including carbon atoms to which the plurality of $R^5$'s are substituted. The corresponding aryl ring is preferably selected from a benzene ring, a naphthalene ring and a phenanthrene ring, more preferably selected from a benzene ring and a phenanthrene ring, even more preferably a benzene ring. A plurality of $R^5$'s may form a plurality of rings, and for example, a plurality of $R^5$'s may be bonded together to form two benzene rings, which may form a phenanthrene ring together with a benzene ring to which the plurality of $R^5$'s are substituted.

From the viewpoint of charge transportability and stability against charges, $R^5$ is preferably selected from an alkyl group, an aryl group that may have an alkyl group, and a silyl group substituted with an alkyl group or a phenyl group, more preferably a $C_6$-$C_{18}$ aryl group that may have a $C_1$-$C_6$ alkyl group, even more preferably a $C_6$-$C_{18}$ aryl group that may have a $C_1$-$C_4$ alkyl group.

Among these, $R^5$ is preferably a methyl group, a t-butyl group, a neopentyl group, an unsubstituted phenyl group, a phenyl group substituted with a cyano group, a fluorine atom or a trifluoromethyl group, a biphenyl group, a terphenyl group, an unsubstituted naphthyl group, a naphthyl group substituted with a methyl group or a t-butyl group, a triphenylsilyl group, or a benzene ring, a naphthalene ring or a phenanthrene ring, formed by the bonding of a plurality of alkyl groups or aryl groups, more preferably an unsubstituted phenyl group, a biphenyl group, a terphenyl group or a benzene ring formed by the bonding of a plurality of alkyl groups, even more preferably an unsubstituted phenyl group, a biphenyl group or a benzene ring formed by the bonding of a plurality of alkyl groups.

n5 is preferably an integer from 0 to 4, more preferably an integer from 0 to 3, even more preferably an integer from 0 to 2, particularly preferably 1 or 2.

The compound represented by Formula (Cz-1) is more preferably a compound represented by Formula (Cz-2).

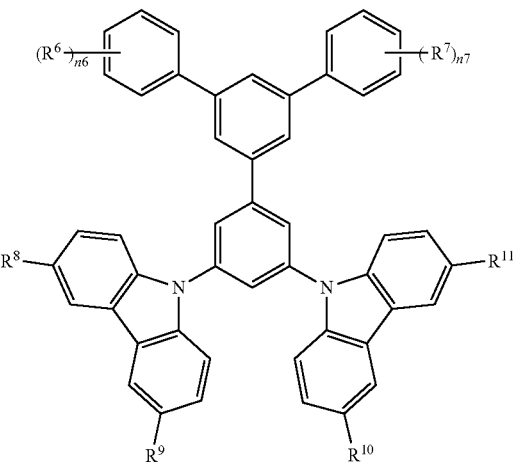

Formula (Cz-2)

In Formula (Cz-2), each of $R^8$ to $R^{11}$ independently represents a hydrogen atom, a fluorine atom, an alkyl group, an aryl group, a silyl group or a cyano group.

Each of $R^6$ and $R^7$ independently represents an alkyl group, an aryl group, a cyano group or a fluorine atom. When $R^6$ and $R^7$ respectively exist in plurality, a plurality of $R^6$'s and a plurality of $R^7$'s may be the same or different respectively. In addition, a plurality of $R^6$'s and a plurality of $R^7$'s may be bonded together to form an aryl ring that may have an alkyl group respectively.

Each of n6 and n7 independently represents an integer from 0 to 5.

Specific examples and preferred examples of an alkyl group, an aryl a plurality of $R^6$'s and a plurality of $R^7$'s may be bonded together to form an aryl ring that may have an alkyl group respectively and a silyl group represented by $R^8$ to $R^{11}$ are the same as those of the alkyl group, the aryl group and the silyl group represented by $R^1$ to $R^4$ in Formula (Cz-1).

From the viewpoint of charge transportability and stability against charges, each of $R^8$ to $R^{11}$ is independently preferably selected from a hydrogen atom, a fluorine atom, a $C_1$-$C_6$ alkyl group that may have a fluorine atom, a $C_6$-$C_{18}$ aryl group that may have a $C_1$-$C_6$ alkyl group, a $C_3$-$C_{18}$ silyl group substituted with a $C_1$-$C_6$ alkyl group or a phenyl group and a cyano group, more preferably selected from a hydrogen atom, a fluorine atom, a $C_1$-$C_4$ alkyl group that may have a fluorine atom, a $C_6$-$C_{12}$ aryl group that may have a $C_1$-$C_4$ alkyl group, a $C_3$-$C_{18}$ silyl group substituted with a $C_1$-$C_4$ alkyl group or a phenyl group, and a cyano group.

Among these, each of $R^8$ to $R^{11}$ is independently preferably selected from a hydrogen atom, a methyl group, an isopropyl group, a t-butyl group, a neopentyl group, a trifluoromethyl group, a phenyl group, a dimethylphenyl group, a trimethylsilyl group, a triphenylsilyl group, a fluorine atom and a cyano group, more preferably selected from a hydrogen atom, a t-butyl group, a phenyl group, a trimethylsilyl group and a triphenylsilyl group, even preferably selected from a hydrogen atom, a t-butyl group, a phenyl group and a triphenylsilyl group.

Specific examples and preferred examples of an alkyl group represented by $R^6$ and $R^7$ are the same as those of the alkyl group represented by $R^1$ to $R^4$ in Formula (Cz-1).

The aryl groups represented by $R^6$ and $R^7$ may have an alkyl group, and in the case of having an alkyl group, the alkyl group is preferably a $C_1$-$C_6$ alkyl group, more preferably a $C_1$-$C_4$ alkyl group. Specific examples and preferred examples of the alkyl group are the same as those of the alkyl group represented by $R^1$ to $R^4$ in Formula (Cz-1).

In the case where the aryl group represented by $R^6$ and $R^7$ has an alkyl group, the aryl group is preferably a $C_6$-$C_{18}$ aryl group, more preferably a $C_6$-$C_{12}$ aryl group. Examples thereof include a phenyl group, a biphenyl group, a terphenyl group, a naphthyl group, an anthranyl group, a phenanthryl group, a chrysenyl group and the like, and among these, a phenyl group, a biphenyl group, a terphenyl group or a naphthyl group is preferred, and a phenyl group, a biphenyl group or a terphenyl group is more preferred.

The aryl group represented by $R^6$ and $R^7$ is preferably unsubstituted aryl group.

Examples of the aryl group represented by $R^6$ and $R^7$ includes a phenyl group, a dimethylphenyl group, a t-butylphenyl group, a biphenyl group, a terphenyl group, a naphthyl group, a methylnaphthyl group, a t-butylnaphthyl group, an anthranyl group, a phenanthryl group, a chrysenyl group and the like, and preferably a phenyl group, a t-butylphenyl group or a biphenyl group, and more preferably a phenyl group.

When $R^6$ and $R^7$ respectively exist in plurality, a plurality of $R^6$'s and a plurality of $R^7$'s may be the same or different respectively. In addition, a plurality of $R^6$'s and a plurality of $R^7$'s may be bonded together to form an aryl ring that may have an alkyl group respectively.

The aryl ring that may have an alkyl group, which are formed by the bonding of each of the plurality of $R^6$'s and the plurality of $R^7$'s is preferably a $C_6$-$C_{30}$ aryl ring that may have a $C_1$-$C_6$ alkyl group, more preferably a $C_6$-$C_{14}$ aryl ring that may have a $C_1$-$C_4$ alkyl group, including carbon atoms to which the plurality of $R^6$'s and the plurality of $R^7$'s are substituted respectively. The formed ring is preferably selected from a benzene ring, a naphthalene ring and a phenanthrene ring, each of which may have a $C_1$-$C_4$ alkyl group, more preferably a benzene ring that may have a $C_1$-$C_4$ alkyl group, for example, a benzene ring or a benzene ring substituted with a t-butyl group. In addition, the plurality of $R^6$'s and the plurality of $R^7$'s may form a plurality of rings, respectively, and for example, the plurality of $R^6$'s or the plurality of $R^7$'s may be bonded together to form two benzene rings, which may form phenanthrene ring together with a benzene ring to which the plurality of $R^6$'s or the plurality of $R^7$'s are substituted.

From the viewpoint of charge transportability and stability against charges, each of $R^6$ and $R^7$ is independently preferably selected from an alkyl group, an aryl group that may have an alkyl group, a cyano group and a fluorine atom, more preferably selected from a $C_1$-$C_6$ alkyl group, a $C_6$-$C_{18}$ aryl group that may have a $C_1$-$C_6$ alkyl group, a cyano group and a fluorine atom, even more preferably selected from a $C_1$-$C_4$ alkyl group, a $C_6$-$C_{12}$ aryl group that may have a $C_1$-$C_4$ alkyl group, a cyano group and a fluorine atom. From the viewpoint of charge transportability and stability against charges, it is preferred that each of $R^6$ and $R^7$ independently represents an alkyl group or an aryl group that may have an alkyl group.

Among these, each of $R^6$ and $R^7$ is independently preferably selected from a methyl group, a trifluoromethyl group, a t-butyl group, an unsubstituted phenyl group, a phenyl group substituted with a t-butyl group, a biphenyl group, a cyano group, a fluorine atom, an unsubstituted benzene ring or a benzene ring substituted with a t-butyl group, formed by the bonding of a plurality of alkyl groups, more preferably selected from a methyl group, a trifluoromethyl group, an unsubstituted phenyl group, a cyano group, a fluorine atom, an unsubstituted benzene ring or a benzene ring substituted with a t-butyl group, formed by the bonding of a plurality of alkyl groups, most preferably an unsubstituted phenyl group.

Each of n6 and n7 are independently preferably an integer from 0 to 4, more preferably an integer from 0 to 2, even more preferably 0 or 1.

It is preferred from the viewpoint of driving durability that the compound represented by Formula (Cz-1) or (Cz-2) consists of a carbon atom, a hydrogen atom and a nitrogen atom only.

The molecular weight of the compound represented by Formula (Cz-1) or (Cz-2) is preferably from 400 to 1,000, more preferably from 450 to 800, even more preferably from 500 to 700. A molecular weight of 400 or higher is advantageous in forming a high-quality amorphous thin film. Meanwhile, a molecular weight of 1,000 or lower contributes to solubility or sublimability improvement, thus being advantageous in improving the purity of the compound.

The compound represented by Formula (Cz-1) or (Cz-2) may be used as a host material of a light emitting layer of an organic electroluminescence device or as a charge transporting material of a layer adjacent to a light emitting layer of an organic electroluminescence device. In this case, the use of the compound represented by Formula (Cz-1) or (Cz-2) having a larger energy gap in the form of a thin film that a light emitting material (in the case where the light emitting material is a phosphorescent material, the energy gap refers to a lowest triplet excitation energy ($T_1$) in the form of a thin film) prevents emitted light from being quenched, thus being advantageous in efficiency improvement. On the other hand, it is preferred that the energy gap is not too large and the $T_1$ energy is not too high taking into consideration the chemical stability of the compound.

The $T_1$ energy of the compound represented by Formula (Cz-1) or (Cz-2) in the form of a film is preferably from 2.69 eV (62 kcal/mol) to 3.47 eV (80 kcal/mol), more preferably from 2.75 eV (63.5 kcal/mol) to 2.61 eV (75 kcal/mol), even more preferably from 2.82 eV (65 kcal/mol) to 3.04 eV (70 kcal/mol). Particularly, when a phosphorescent material is used as a light emitting material, it is preferred that the $T_1$ energy falls within the range defined above.

The T1 energy can be obtained from the short wavelength limit of a phosphorescence spectrum of a thin film of the material. For example, after the material is formed into a film having a thickness of about 50 nm on a pre-cleaned quartz glass substrate by vacuum deposition, a phosphorescence spectrum of the thin film is measured using a fluorescence spectrophotometer (F-7000, Hitachi High-Technologies) at a temperature of liquid nitrogen. The rising wavelengths in a short wavelength region of the emission spectrum are expressed as energy units, from which the T1 energy is calculated.

From the viewpoint of achieving stable operation of an organic electroluminescence device during driving at high temperature or against heat emitted during driving, the glass transition temperature ($T_g$) of the compound represented by Formula (Cz-1) or (Cz-2) is preferably from 80° C. to 400° C., more preferably from 100° C. to 400° C., even more preferably from 120° C. to 400° C.
Specific examples of the compound represented by Formula (Cz-1) or (Cz-2) are exemplified below, but the present invention is not limited thereto.
(1)
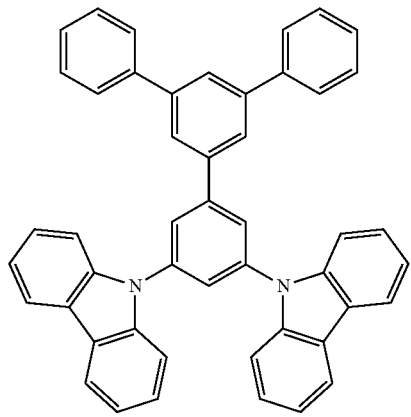
(2)
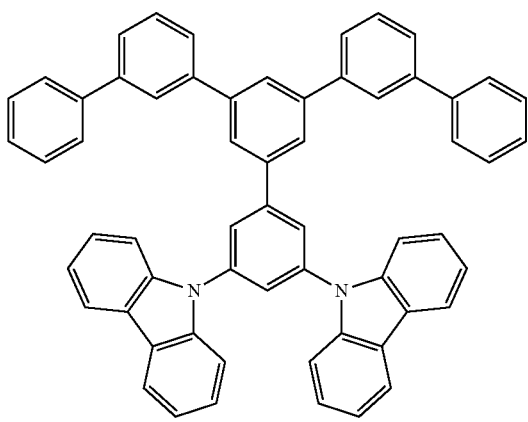
(3)
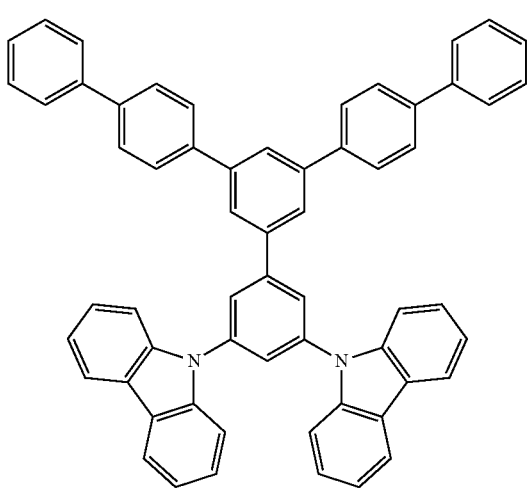
-continued
(4)
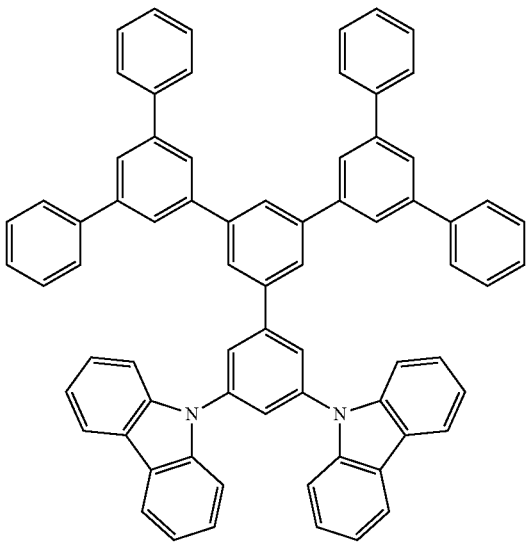
(5)
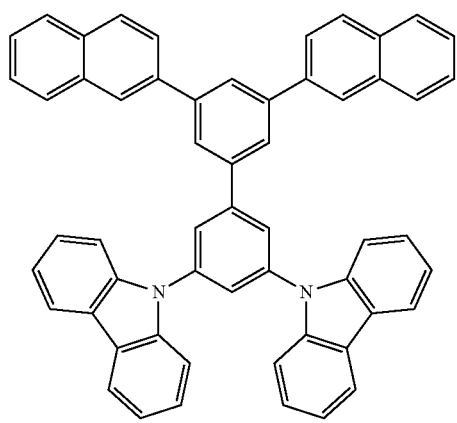
(6)
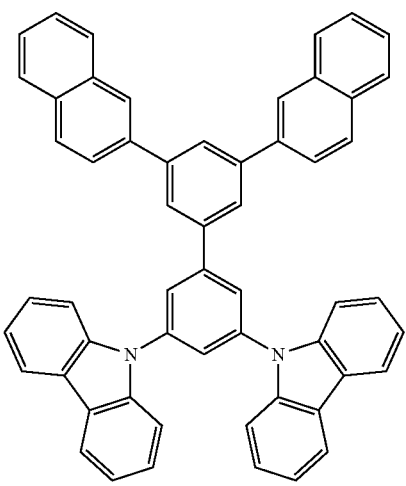

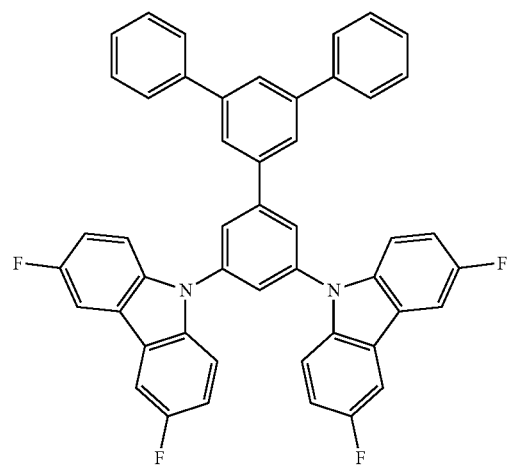
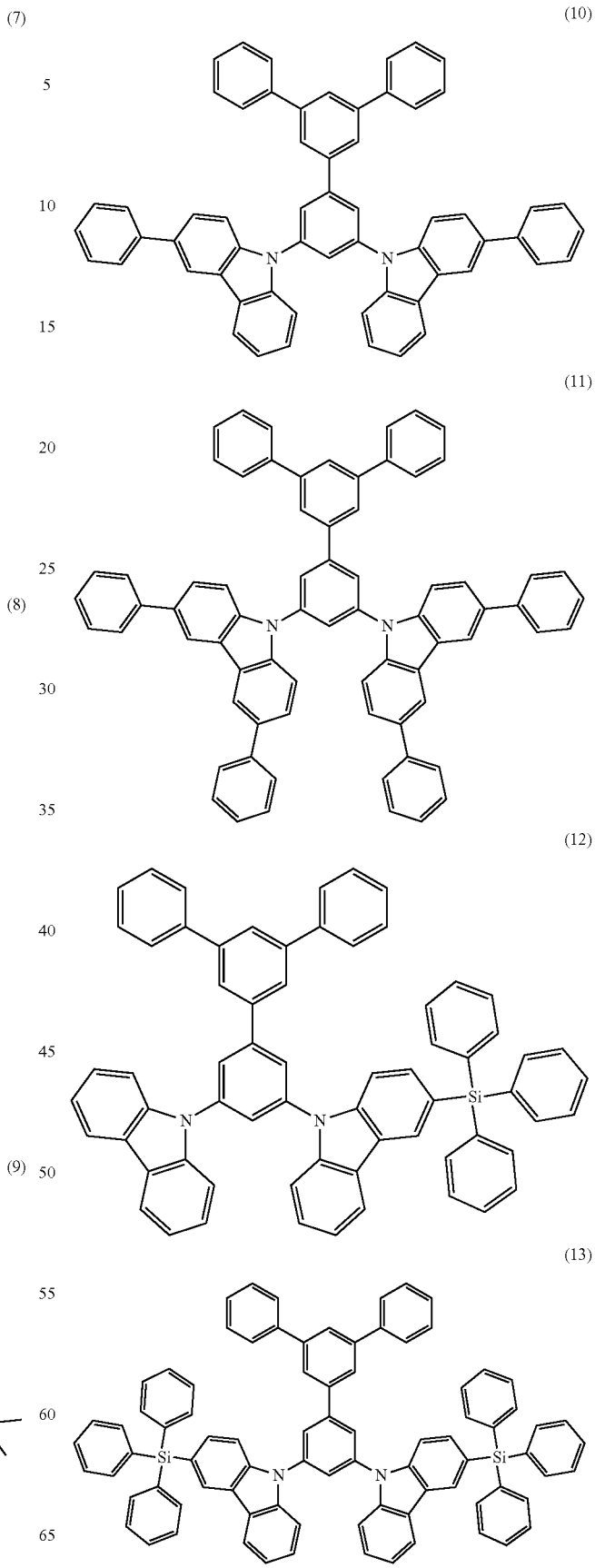

-continued
(14)
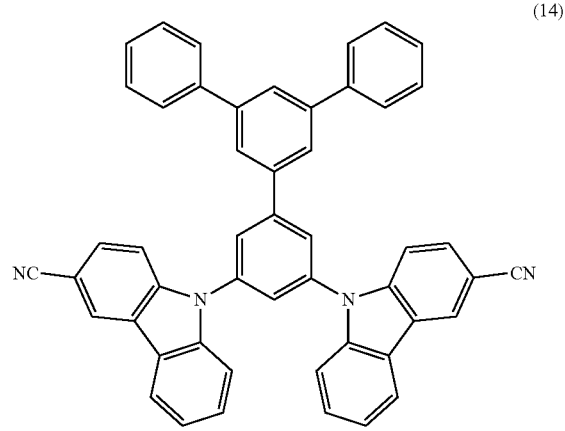
(15)
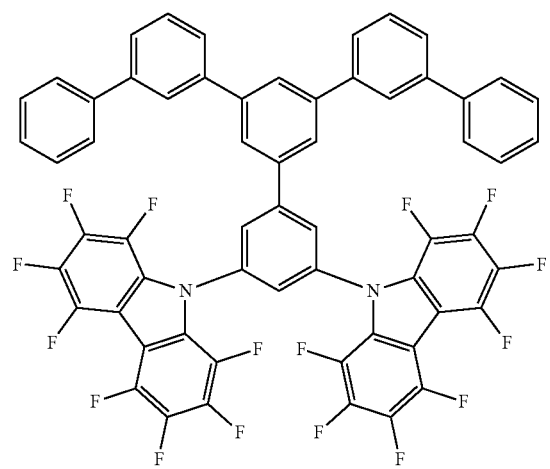
(16)
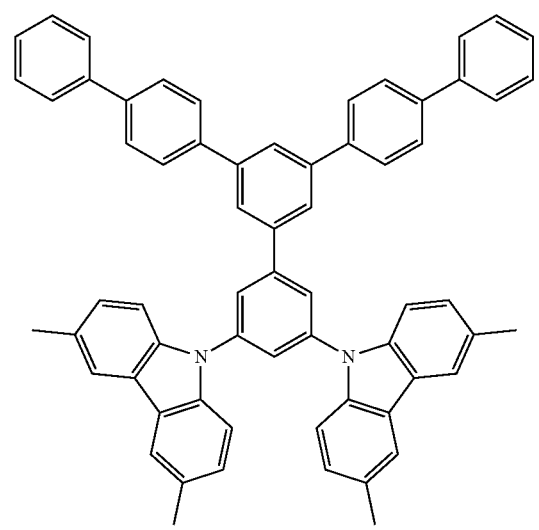
-continued
(17)
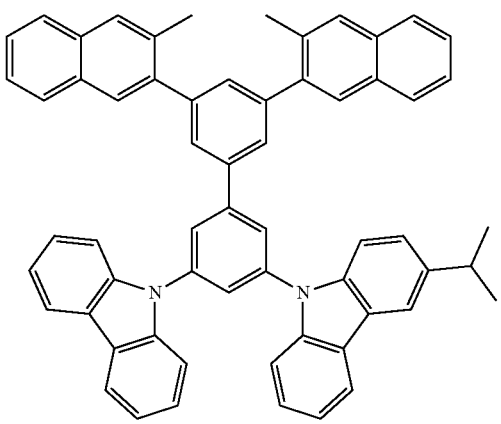
(18)
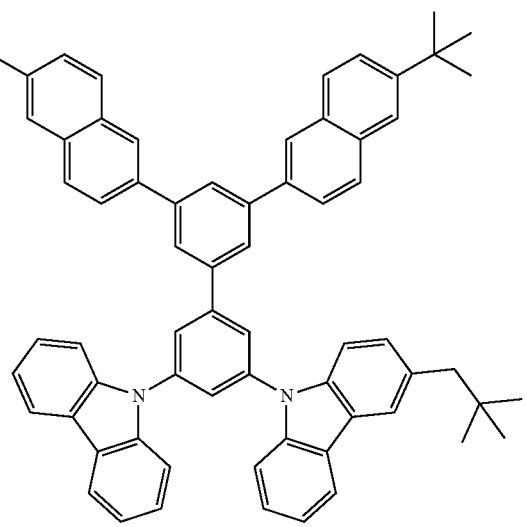
(19)
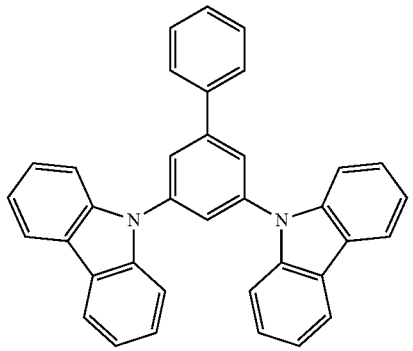

(20)
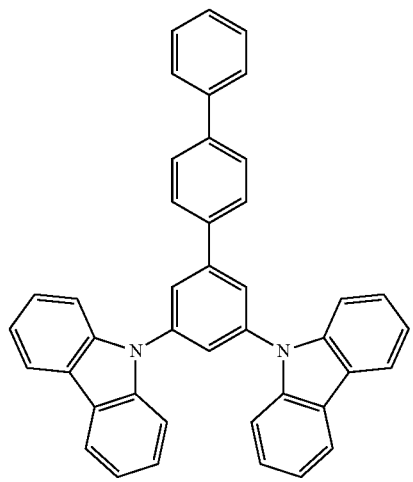
(21)
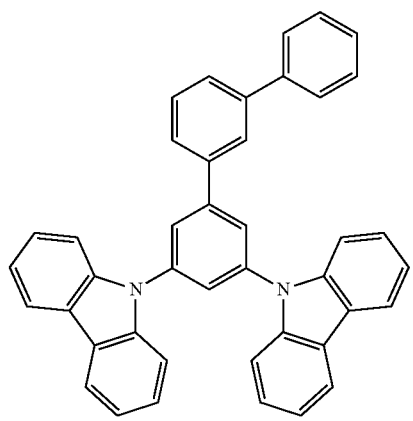
(22)
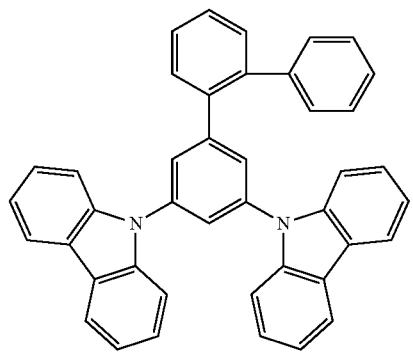
(23)
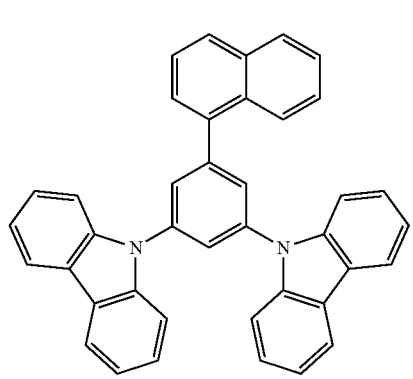
(24)
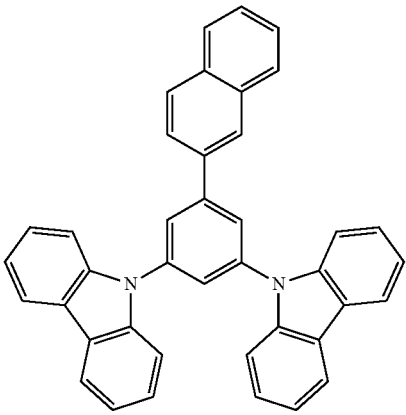
(25)
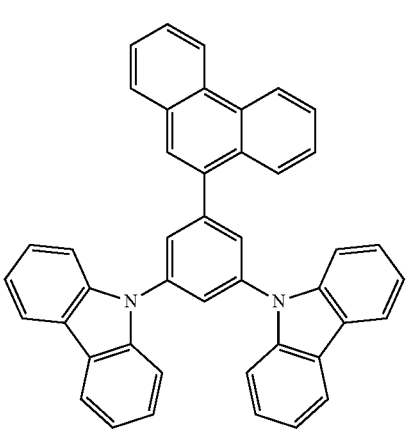
(26)
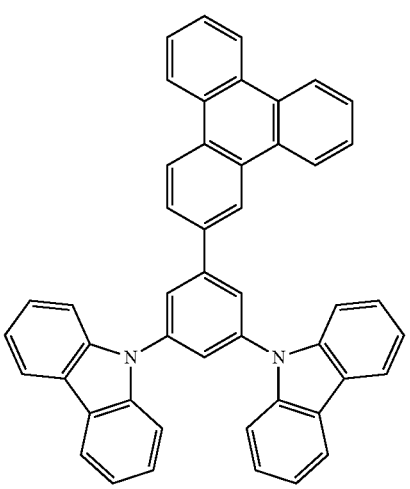

-continued
(27)
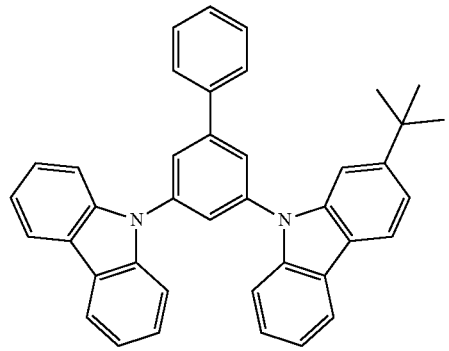
(28)
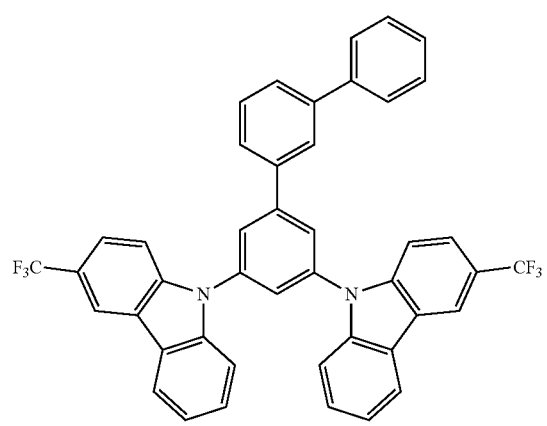
(29)
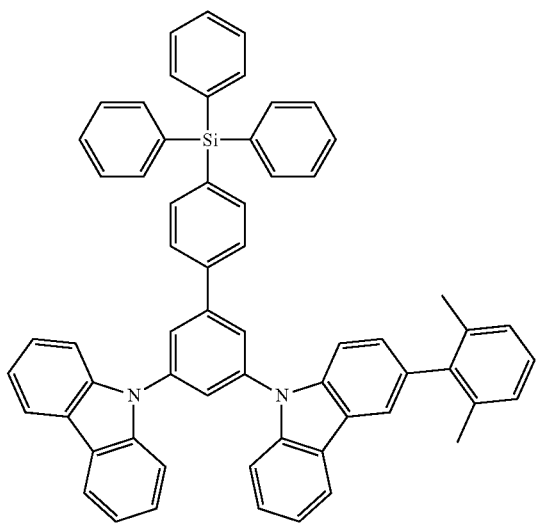
(30)
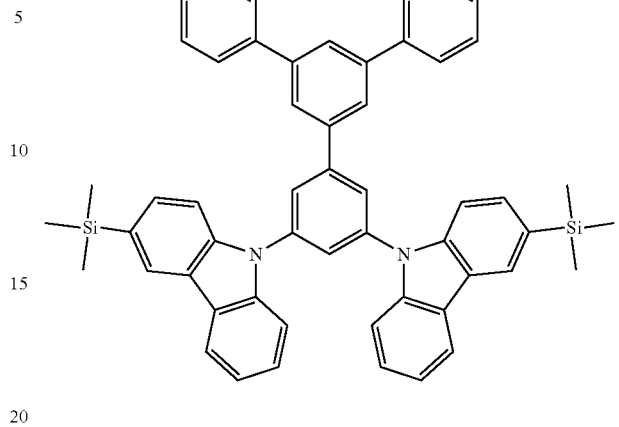
(31)
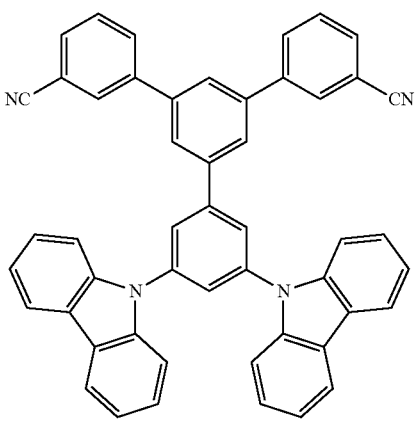
(32)
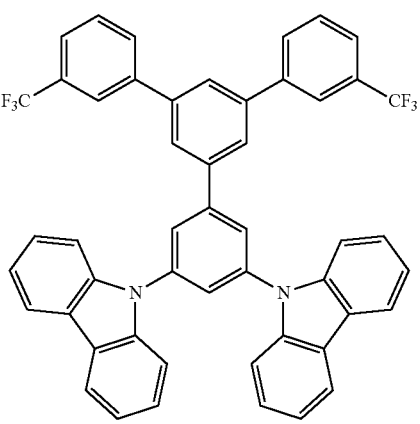

(33)
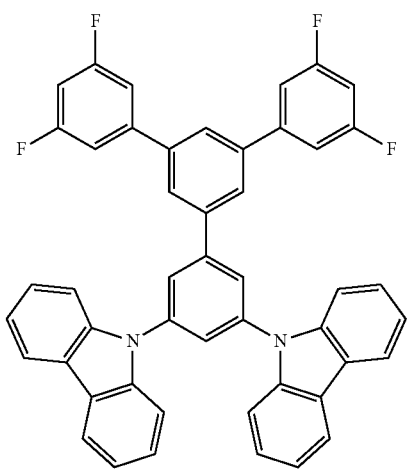

(34)
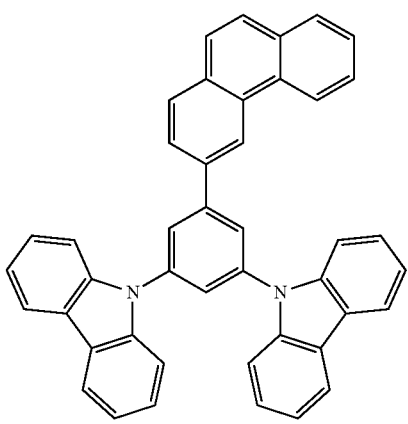

(35)
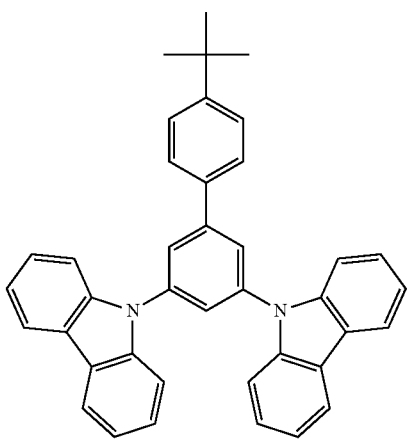

(36)
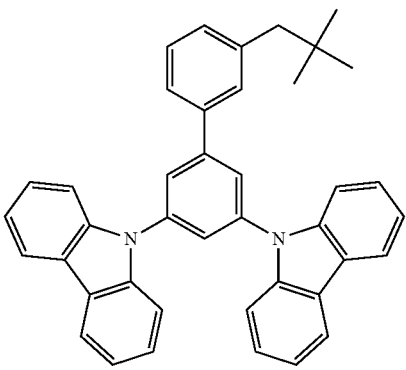

(37)
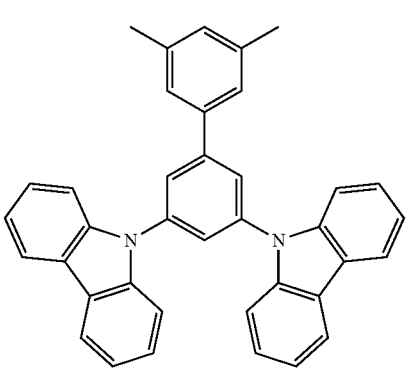

The compounds exemplified as the compound represented by Formula (Cz-1) or (Cz-2) can be synthesized with reference to the pamphlet of International Publication No. 2004/074399. For example, the exemplified compound (1) can be synthesized through the following synthetic route by the method of Synthesis Example 2 described at page 52, line 22 to page 54, line 15 of International Publication No. 2004/074399.

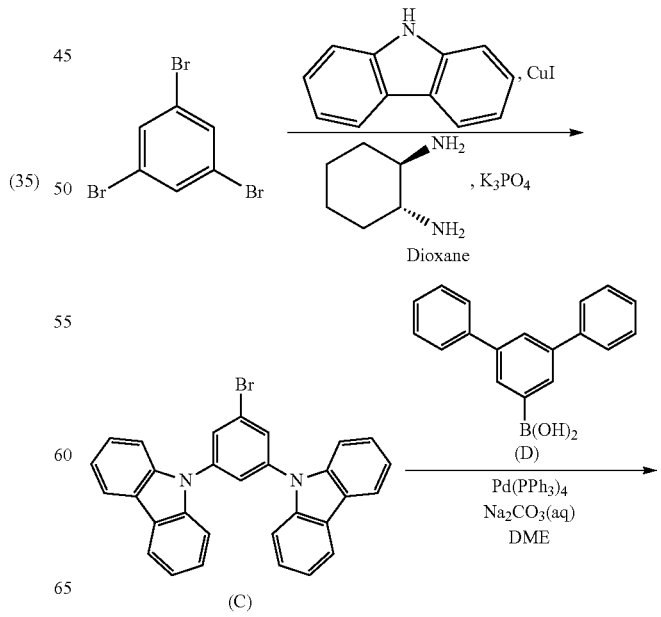

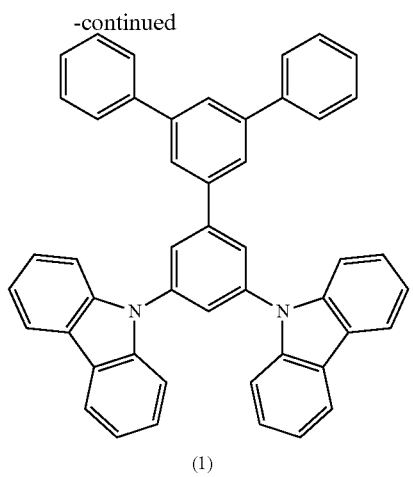

(1)

In the present invention, the compound represented by Formula (Cz-1) or (Cz-2) may be contained in any constituent layer of an organic layer but is not limited to this use. The compound represented by Formula (Cz-1) or (Cz-2) is preferably introduced into a light emitting layer, a layer between a light emitting layer and a cathode, a layer between a light emitting layer and an anode, or a plurality of layers thereof. The compound is more preferably contained in a light emitting layer, a hole injection layer, a hole transporting layer, an electron transporting layer, an electron injection layer, an exciton blocking layer, a charge blocking layer, or a plurality of layers thereof.

In the present invention, in order to suppress a change in chromaticity after driving at high temperature, the compound represented by Formula (Cz-1) or (Cz-2) is preferably contained in a light emitting layer or a layer adjacent to a light emitting layer, more preferably in a light emitting layer. Alternatively, the compound represented by Formula (Cz-1) or (Cz-2) may be contained in both a light emitting layer and a layer adjacent to the light emitting layer.

When the compound represented by Formula (Cz-1) or (Cz-2) is contained in a light emitting layer, it is preferably included in an amount of 0.1 to 99% by mass, more preferably 1 to 95% by mass, even more preferably 10 to 95% by mass, based on the total mass of the light emitting layer.

When the compound represented by Formula (Cz-1) or (Cz-2) is contained in a layer in addition to in a light emitting layer, it is preferably included in an amount of 70 to 100% by mass, more preferably 85 to 100% by mass, based on the total mass of the corresponding layer.

Next, an explanation will be given regarding impurities in a charge transporting material including the compound represented by Formula (Cz-1) or (Cz-2).

In the present invention, the content of an impurity represented by Formula (I-1) in the charge transporting material including the compound represented by Formula (Cz-1) is limited to 0.000% to 0.10% when it is calculated as a proportion of the absorption intensity area of the impurity represented by Formula (I-1) with respect to the total absorption intensity area of the charge transporting material, as measured by high-performance liquid chromatography at a measurement wavelength of 254 nm.

In the case where the charge transporting material of the present invention includes the compound represented by Formula (Cz-2), the content of an impurity represented by Formula (I-2) in the charge transporting material is limited to 0.000% to 0.10% when it is calculated as a proportion of the absorption intensity area of the impurity represented by Formula (I-2) with respect to the total absorption intensity area of the charge transporting material, as measured by high-performance liquid chromatography at a measurement wavelength of 254 nm.

Since the impurity represented by Formula (I-1) or (I-2) has a very great influence on the device performance, a lower content of the impurity in the charge transporting material is more preferable. When calculated by the above-described method, the impurity content is preferably 0.05% or less, more preferably 0.01% or less, most preferably 0%.

On the other hand, since a further reduction in the trace amount of the impurity of 0.10% or less is very technically difficult and causes loss of the material, it is not desirable in terms of production cost to purify the material at a higher level than is necessary. From the viewpoint of performance, the presence of the impurity in an amount of 0.10% or less is sufficient to obtain good effects over a device known in the related art and does not make any significant difference in terms of performance within the range of 0.10% or less. Therefore, the content of the impurity represented by Formula (I-1) or (I-2) in the charge transporting material is preferably greater than 0.000%, more preferably 0.001% or more, even more preferably 0.005% or more, particularly preferably 0.010% or more, when calculated by the above-described method.

In addition, the detection limit of general high-performance liquid chromatography is about 0.001% by mass at a sample concentration of 0.05% by mass. The expression "a certain component is present in an amount of 0%" in the present invention means that the component is not detected by high-performance liquid chromatography, implying the presence of the component in a very small amount below the detection limit of high-performance liquid chromatography. Further, the expression "the proportion of the sum of the absorption intensity area of a certain component and the absorption intensity area of another certain component is 100%" means that components other than the certain components are present in very small amounts below the detection limit of high-performance liquid chromatography.

The compound represented by Formula (I-1) or (I-2) corresponds to the intermediate (C) in the synthetic route described in International Publication No. 2004/074399. That is, the compound represented by Formula (I-1) or (I-2) is used as the intermediate (C) for the synthesis of the compound represented by Formula (Cz-1) or (Cz-2). The compound represented by Formula (I-1) or (I-2) remains unreacted in the product, and thus, becomes an impurity.

Formula (I-1)

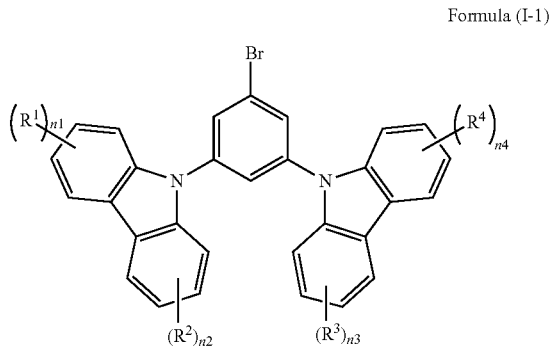

$R^1$ to $R^4$ in Formula (I-1) are the same atoms or groups as defined for $R^1$ to $R^4$ in Formula (Cz-1) respectively.

n1 to n4 are the same integers as defined for n1 to n4 in Formula (Cz-1) respectively.

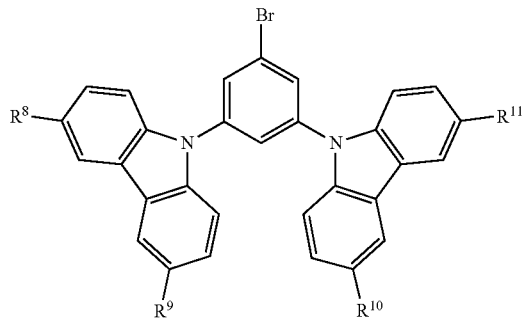

Formula (I-2)

$R^8$ to $R^{11}$ in Formula (I-2) are the same atoms or groups as defined for $R^8$ to $R^{11}$ in Formula (Cz-2) respectively.

According to a present inventors' review, the presence of the impurity represented by Formula (I-1) or (I-2) in an amount exceeding 0.10% in the charge transporting material including the compound represented by Formula (Cz-1) or (Cz-2) when the content of the impurity is calculated as a proportion of the absorption intensity area of the impurity represented by Formula (I-1) or (I-2) with respect to the total absorption intensity area of the charge transporting material, as measured by high-performance liquid chromatography at a measurement wavelength of 254 nm, has proved to adversely affect the device performance, particularly durability, and to be difficult to make luminous efficiency and durability compatible with each other at a high level. The reason for these remains unknown but is thought to be as follows. An impurity having a molecular weight and a structure close to those of a desired charge transporting material is difficult to be separated from the charge transporting material by purification and tends to be incorporated into a film after deposition due to its sublimation temperature close to that of the charge transporting material. In addition, the HOMO and LUMO values of a desired charge transporting material are close to those of an impurity having a similar structure to the charge transporting material and the orbitals of the charge transporting material largely overlap those of the impurity due to their similar structures. For these reasons, charges are loaded even on the impurity during charge transport, permitting the impurity to act as a charge transport trap. The substitution of such an impurity having a similar structure with a bromine atom allows the impurity to react with reactive active species in various states, such as radical cation, radical anion and excited states, created during driving of a device, or causes the impurity to become more reactive active species in various states, such as radical cation, radical anion and excited states, which degrades a charge transporting material, and accordingly, this mechanism is thought to worsen the durability of the device.

The contents of the impurity represented by Formula (I-1) or (I-2) and other impurities in the charge transporting material of the present invention and the purity of the charge transporting material of the present invention can be determined, for example, by high-performance liquid chromatography (HPLC) under the following analysis conditions.

(Analysis Conditions for HPLC)
HPLC system: HPLC manufactured by Shimadzu Corporation (LC-10 ADVP pump, CTO-10 ACVP column oven, SIL-10 ADVP autosampler, RID-10 A differential refractive index detector, CLASS-VP analysis software)
Column: TSKgel ODS-100Z, Tosoh
Mobile layer, flow rate: 60% aqueous tetrahydrofuran (THF) solution, 1.0 ml/min
Column temperature: 40° C.
Sample concentration: 0.05% by mass In the present invention, values calculated from the area ratios of the absorption intensities at 254 nm are used as the "contents" of the impurities and the "purity" of the charge transporting material. In the following description, unless specified otherwise, the "contents" of the impurities and the "purity" of the charge transporting material mean values calculated by the above-described method.

In addition to the compound represented by Formula (I-1) or (I-2), 1,3,5-tribromobenzene as a starting material for the synthesis of the compound represented by Formula (I-1) or (I-2) and the compound corresponding to the intermediate (D) in the synthetic route described in International Publication No. 2004/074399 (hereinafter, the compound represented by Formula (II-1) or (II-2)) may be included as impurities in the charge transporting material of the present invention. That is, the compound represented by Formula (II-1) or (II-2) is used as an intermediate (D) for the synthesis of the compound represented by Formula (Cz-1) or (Cz-2) and remains unreacted in the product and thus becomes an impurity.

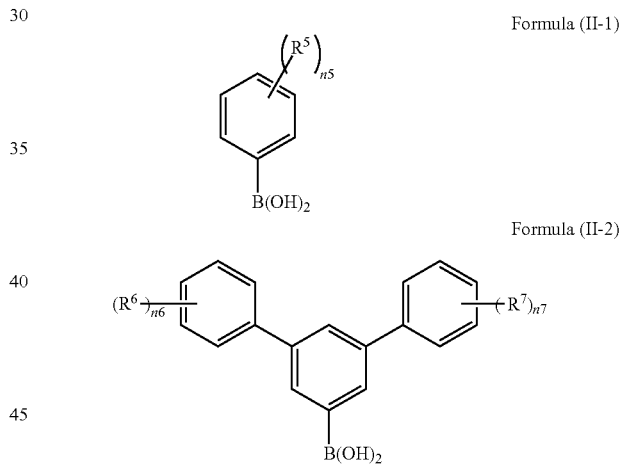

In Formula (II-1), $R^5$ is the same group as defined for $R^5$ in Formula (Cz-1).

n5 is the same integer as defined for n5 in Formula (Cz-1).

In Formula (II-2), $R^6$ and $R^7$ are the same groups or atoms as defined for $R^6$ and $R^7$ in Formula (Cz-2) respectively.

n6 and n7 are the same integers as defined for n6 and n7 in Formula (Cz-2) respectively.

According to a present inventors' review, unlike the presence of the impurity represented by Formula (I-1) or (I-2), the presence of the impurity represented by Formula (II-1) or (II-2) and 1,3,5-tribromobenzene in the charge transporting material including the compound represented by Formula (Cz-1) or (Cz-2) has proved to have no adverse influence on the device performance, such as external quantum efficiency or durability. Particularly, from the fact that 1,3,5-tribromobenzene has no adverse influence on the device performance, such as external quantum efficiency or durability, it could be known that not all bromo compounds adversely affect the device performance and the particular impurity represented by Formula (I-1) or (I-2) specifically adversely affects the device performance.

The content of the impurity represented by Formula (II-1) or (II-2) that may remain in the charge transporting material of the present invention is typically from 0.000% to 1.0%, preferably from 0.000% to 0.5%.

The content of 1,3,5-tribromobenzene that may remain in the charge transporting material of the present invention is typically from 0.000% to 1.0%, preferably from 0.000% to 0.5%.

In addition, the purity of the charge transporting material of the present invention is preferably from 99.0% to 100%, more preferably from 99.5% to 100%, even more preferably from 99.9% to 100%.

It is preferred that any impurities other than the impurity represented by Formula (I-1) or (I-2), the impurity represented by Formula (II-1) or (II-2) and 1,3,5-tribromobenzene are not detected by high-performance liquid chromatography described above.

That is, in the charge transporting material of the present invention containing the compound represented by Formula (Cz-1), it is preferred that the proportion of the sum of the absorption intensity areas of the compound represented by Formula (Cz-1), the impurity represented by Formula (I-1), the impurity represented by Formula (II-1) and 1,3,5-tribromobenzene with respect to the total absorption intensity area of the charge transporting material, as measured by high-performance liquid chromatography at a measurement wavelength of 254 nm, is preferably 100%.

Likewise, in the charge transporting material of the present invention containing the compound represented by Formula (Cz-2), it is preferred that the proportion of the sum of the absorption intensity areas of the compound represented by Formula (Cz-2), the impurity represented by Formula (I-2), the impurity represented by Formula (II-2) and 1,3,5-tribromobenzene with respect to the total absorption intensity area of the charge transporting material, as measured by high-performance liquid chromatography at a measurement wavelength of 254 nm, is preferably 100%.

As described above, the compound represented by Formula (Cz-1) or (Cz-2) is synthesized and purified by the method of Synthesis Example 2 described at page 52, line 22 to page 54, line 15 of International Publication No. 2004/074399. However, since the content of the impurity represented by Formula (I-1) or (I-2) in the product prepared by the method is larger than 0.10%, further purification is necessitated. Purification processes known in the related art can be applied without particular limitation such that the content of the impurity represented by Formula (I-1) or (I-2) in the charge transporting material is limited to 0.10% or less. It is preferred to purify the charge transporting material by column chromatography and/or recrystallization, followed by sublimation. The purification by sublimation enables effective removal of inorganic salts or residual solvents as well as separation of the organic impurities. In addition, it is preferred to perform the purification procedure by recrystallization and sublimation several times.

[Applications of the Charge Transporting Material of the Present Invention]

The charge transporting material of the present invention can applications in various organic electronic devices, preferably electrophotographic devices, organic transistors, organic photovoltaic devices (for example, for energy conversion and sensors), organic electroluminescence devices, and the like, particularly preferably organic electroluminescence devices.

The charge transporting material of the present invention may be contained in any layer of organic layers of an organic electroluminescence device. The charge transporting material of the present invention is preferably used in any layer of a hole injection layer, a hole transporting layer, a light emitting layer, an electron transporting layer and an electron injection layer, more preferably a light emitting layer, an electron transporting layer and an electron injection layer, even more preferably a light emitting layer and an electron transporting layer, most preferably a light emitting layer.

[Composition Containing the Charge Transporting Material of the Present Invention]

The present invention also relates to a composition including the charge transporting material. The content of the compound represented by Formula (Cz-1) or (Cz-2) in the composition of the present invention is preferably from 30 to 99% by mass, more preferably from 50 to 95% by mass, even more preferably from 70 to 90% by mass, based on the solids content of the composition. In addition to the charge transporting material, the composition of the present invention may contain any organic or inorganic material. Examples of suitable organic materials include host materials, fluorescent materials, phosphorescent materials and hydrocarbon materials, which will be described below. Host materials, phosphorescent materials and hydrocarbon materials are preferred.

The composition of the present invention can be used to form an organic layer of an organic electroluminescence device, for example, by a dry film formation process, such as deposition or sputtering, a transfer process or a printing process.

[Thin Film Containing the Charge Transporting Material of the Present Invention]

The present invention also relates to a thin film containing the charge transporting material including the compound represented by Formula (Cz-1) or (Cz-2). The thin film of the present invention may be formed, for example, by a dry film formation process, such as deposition or sputtering, a transfer process or a printing process using the composition of the present invention. The thickness of the thin film may vary depending on the intended use but is preferably from 0.1 nm to 1 mm, more preferably 0.5 nm to 1 µm, even more preferably 1 nm to 200 nm, particularly preferably from 1 nm to 100 nm.

[Organic Electroluminescence Device]

A detailed explanation will be given regarding an organic electroluminescence device of the present invention.

The organic electroluminescence device of the present invention has a pair of electrodes on a substrate and at least one layer of an organic layer including a light emitting layer between the electrodes wherein any constituent layer of the at least one layer of an organic layer includes the charge transporting material of the present invention. In view of the characteristics of the luminescence device, it is preferred that at least one electrode of the anode and cathode as the pair of electrodes is transparent or translucent.

In addition to the light emitting layer, the organic layer may include a hole injection layer, a hole transporting layer, blocking layers (such as a hole blocking layer and an exciton blocking layer) and an electron transporting layer. Each constituent layer of the organic layer may be provided in plurality. In this case, the constituent layers may be formed of the same material or different materials.

An exemplary construction of the organic electroluminescence device according to the present invention is illustrated in FIG. 1. The organic electroluminescence device 10 of FIG. 1 has a pair of electrodes (i.e. an anode 3 and a cathode 9) on a substrate 2 and an organic layer including a light emitting layer 6 between the electrodes. The organic layer has a structure in which a hole injection layer 4, a hole transporting layer 5, the light emitting layer 6, a hole blocking layer 7 and an electron transporting layer 8 are laminated in this order on the anode 3.

<Construction of the Organic Layer>

No particular restriction is imposed on the construction of the organic layer. The organic layer can be suitably selected according to the intended use and purpose of the organic electroluminescence device, but is preferably formed on the transparent or translucent electrode. In this case, the organic layer is formed over the entire surface or on one surface of the transparent or translucent electrode.

The shape, size, thickness and the like of the organic layer are not particularly limited and may be suitably selected depending on the intended purpose.

Specific constructions of the organic layer are exemplified below, but the present invention is not limited to these constructions.

- Anode/hole transporting layer/light emitting layer/electron transporting layer/cathode,
- Anode/hole transporting layer/light emitting layer/blocking layer/electron transporting layer/cathode,
- Anode/hole transporting layer/light emitting layer/blocking layer/electron transporting layer/electron injection layer/cathode,
- Anode/hole transporting layer/light emitting layer/electron transporting layer/electron injection layer/cathode
- Anode/hole injection layer/hole transporting layer/light emitting layer/blocking layer/electron transporting layer/cathode,
- Anode/hole injection layer/hole transporting layer/light emitting layer/blocking layer/electron transporting layer/electron injection layer/cathode.

The constructions, substrates, cathodes and anodes of organic electroluminescence devices are described in the literature, for example, Japanese Patent Application Laid-Open No. 2008-270736, and the description of the patent publication can be applied to the present invention.

<Substrate>

The substrate used in the present invention is preferably one that does not scatter or attenuate light emitted from the organic layer. The substrate is particularly preferably made of an organic material having good heat resistance, dimensional stability, solvent resistance, electrical insulation and processability.

<Anode>

So long as the anode has an electrode function of supplying holes to the organic layer, no particular restriction is imposed on the shape, structure, size and the like of the anode. The anode material can be suitably selected from known electrode materials according to the intended use or purpose of the luminescence device. As described above, the anode is usually made of a transparent electrode material.

<Cathode>

So long as the cathode has an electrode function of injecting electrons to the organic layer, no particular restriction is imposed on the shape, structure, size and the like of the cathode. The cathode material can be suitably selected from known electrode materials according to the intended use or purpose of the luminescence device.

<Organic Layer>

An explanation will be given regarding the organic layer in the present invention.

—Formation of the Organic Layer—

In the organic electroluminescence device of the present invention, the constituent layers of the organic layer may be suitably formed, for example, by a dry film formation process, such as deposition and sputtering, a transfer process, a printing process, a spin coating process or a bar coating process. It is preferred to form at least one constituent layer of the organic layer by a solution coating process.

(Light Emitting Layer)

The light emitting layer has a function of accepting holes from the anode, the hole injection layer or the hole transporting layer, accepting electrons from the cathode, the electron injection layer or the electron transporting layer, and providing a site where the holes recombine the electrons to emit light, in response to an applied electric field.

<Light Emitting Material>

In the present invention, either a fluorescent material or a phosphorescent material or both of them may be used as a light emitting material.

Examples of the fluorescent material and the phosphorescent material are described in Paragraph Nos. [0100] to [0164] of Japanese Patent Application Laid-Open No. 2008-270736 and Paragraph Nos. [0088] to [0090] of Japanese Patent Application Laid-Open No. 2007-266458. The descriptions of these patent publications can be applied to the present invention.

From the viewpoint of luminous efficiency and the like, a phosphorescent material is preferred as the light emitting material. Examples of phosphorescent material usable in the present invention include phosphorescent compounds described in the following patent documents: U.S. Pat. No. 6,303,238B1, U.S. Pat. No. 6,097,147, WO 00/57676, WO 00/70655, WO 01/08230, WO 01/39234 A2, WO 01/41512 A1, WO 02/02714 A2, WO 02/15645 A1, WO 02/44189 A1, WO 05/19373 A2, Japanese Patent Application Laid-Open No. 2001-247859, Japanese Patent Application Laid-Open No. 2002-302671, Japanese Patent Application Laid-Open No. 2002-117978, Japanese Patent Application Laid-Open No. 2003-133074, Japanese Patent Application Laid-Open No. 2002-235076, Japanese Patent Application Laid-Open No. 2003-123982, Japanese Patent Application Laid-Open No. 2002-170684, EP 1211257, Japanese Patent Application Laid-Open No. 2002-226495, Japanese Patent Application Laid-Open No. 2002-234894, Japanese Patent Application Laid-Open No. 2001-247859, Japanese Patent Application Laid-Open No. 2001-298470, Japanese Patent Application Laid-Open No. 2002-173674, Japanese Patent Application Laid-Open No. 2002-203678, Japanese Patent Application Laid-Open No. 2002-203679, Japanese Patent Application Laid-Open No. 2004-357791, Japanese Patent Application Laid-Open No. 2006-256999, Japanese Patent Application Laid-Open No. 2007-19462, Japanese Patent Application Laid-Open No. 2007-84635, Japanese Patent Application Laid-Open No. 2007-96259 and the like, and among these, Ir complexes, Pt complexes, Cu complexes, Re complexes, W complexes, Rh complexes, Ru complexes, Pd complexes, Os complexes, Eu complexes, Tb complexes, Gd complexes, Dy complexes and Ce complexes are more preferred luminescent dopants. Particularly preferred are Ir complexes, Pt complexes or Re complexes, particularly preferably those including at least one coordination mode of metal-carbon bonds, metal-nitrogen bonds, metal-oxygen bonds and metal-sulfur bonds. From the viewpoint of luminous efficiency, driving durability, chromaticity and the like, particularly preferred are Ir complexes and Pt complexes, and most preferred are Ir complexes.

Preferred is a platinum complex represented by Formula (C-1).

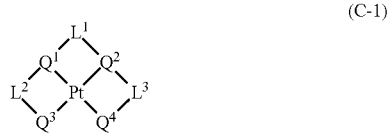

(C-1)

(wherein each of $Q^1$, $Q^2$, $Q^3$ and $Q^4$ independently represents a ligand coordinated to Pt and each of $L^1$, $L^2$ and $L^3$ independently represents a single bond or a divalent linking group).

Formula (C-1) will be explained below. Each of $Q^1$, $Q^2$, $Q^3$ and $Q^4$ independently represents a ligand coordinated to Pt. $Q^1$, $Q^2$, $Q^3$ and $Q^4$ may be bound to Pt through any bonding, such as covalent bonding, ionic bonding, coordinate bonding or the like. The atoms in $Q^1$, $Q^2$, $Q^3$ and $Q^4$ bound to Pt are preferably carbon atoms, nitrogen atoms, oxygen atoms, sulfur atoms and phosphorus atoms. At least one of the atoms in $Q^1$, $Q^2$, $Q^3$ and $Q^4$ bound to Pt is preferably a carbon atom. Two of the atoms in $Q^1$, $Q^2$, $Q^3$ and $Q^4$ bound to Pt are more preferably carbon atoms. The atoms in $Q^1$, $Q^2$, $Q^3$ and $Q^4$ bound to Pt are particularly preferably two carbon atoms and two nitrogen atoms.

$Q^1$, $Q^2$, $Q^3$ and $Q^4$ bound to Pt via carbon atoms may be anionic or neutral ligands. Examples of the anionic ligands include vinyl ligands, aromatic hydrocarbon ring ligands (for example, benzene, naphthalene, anthracene, phenanthrene ligands and the like), and heterocyclic ligands (for example, furan ligands, thiophene ligands, pyridine ligands, pyrazine ligands, pyrimidine ligands, pyridazine ligands, triazine ligands, thiazole ligands, oxazole ligands, pyrrole ligands, imidazole ligands, pyrazole ligands, triazole ligands, and condensed rings including these ligands (for example, quinoline, benzothiazole ligands and the like)). Examples of the neutral ligands include carbene ligands.

$Q^1$, $Q^2$, $Q^3$ and $Q^4$ bound to Pt via nitrogen atoms may be neutral or anionic ligands. Examples of the neutral ligands include nitrogen-containing aromatic heterocyclic ligands (for example, pyridine ligands, pyrazine ligands, pyrimidine ligands, pyridazine ligands, triazine ligands, imidazole ligands, pyrazole ligands, triazole ligands, oxazole ligands, thiazole ligands, and condensed rings including these ligands (for example, quinoline, benzimidazole ligands and the like)), amine ligands, nitrile ligands and imine ligands. Examples of the anionic ligands include amino ligands, imino ligands and nitrogen-containing aromatic heterocyclic ligands (for example, pyrrole ligands, imidazole ligands, triazole ligands, and condensed rings including these ligands (for example, indole, benzimidazole ligands and like)).

$Q^1$, $Q^2$, $Q^3$ and $Q^4$ bound to Pt via oxygen atoms may be neutral or anionic ligands. Examples of the neutral ligands include ether ligands, ketone ligands, ester ligands, amide ligands, and oxygen-containing heterocyclic ligands (for example, furan ligands and oxazole ligands, and condensed rings including these ligands (for example, benzoxazole ligands and the like)). Examples of the anionic ligands include alkoxy ligands, aryloxy ligands, heteroaryloxy ligands, acyloxy ligands, silyloxy ligands and the like.

$Q^1$, $Q^2$, $Q^3$ and $Q^4$ bound to Pt via sulfur atoms may be neutral or anionic ligands. Examples of the neutral ligands include thioether ligands, thioketone ligands, thioester ligands, thioamide ligands and sulfur-containing heterocyclic ligands (for example, thiophene ligands, thiazole ligands and condensed rings including these ligands (for example, benzothiazole ligands and the like)). Examples of the anionic ligands include alkylmercapto ligands, arylmercapto ligands, heteroarylmercapto ligands and the like.

$Q^1$, $Q^2$, $Q^3$ and $Q^4$ bound to Pt via phosphorus atoms may be neutral or anionic ligands. Examples of the neutral ligands include phosphine ligands, phosphoric acid ester ligands, phosphorous acid ester ligands, and phosphorus-containing heterocyclic ligands (such as phosphinine ligands). Examples of the anionic ligands include phosphino ligands, phosphinyl ligands, phosphoryl ligands and the like.

The groups represented by $Q^1$, $Q^2$, $Q^3$ and $Q^4$ may have substituents. The substituents can be suitably selected from those exemplified in the group A of substituents. The substituents may be linked to each other (for example, when $Q^3$ is linked to $Q^4$, the Pt complex has cyclic tetradentate ligands).

The groups represented by $Q^1$, $Q^2$, $Q^3$ and $Q^4$ are preferably aromatic hydrocarbon ring ligands bound to Pt via carbon atoms, aromatic heterocyclic ligands bound to Pt via carbon atoms, nitrogen-containing aromatic heterocyclic ligands bound to Pt via nitrogen atoms, acyloxy ligands, alkyloxy ligands, aryloxy ligands, heteroaryloxy ligands or silyloxy ligands, more preferably aromatic hydrocarbon ring ligands bound to Pt via carbon atoms, aromatic heterocyclic ligands bound to Pt via carbon atoms, nitrogen-containing aromatic heterocyclic ligands bound to Pt via nitrogen atoms, acyloxy ligands or aryloxy ligands, even more preferably aromatic hydrocarbon ring ligands bound to Pt via carbon atoms, aromatic heterocyclic ligands bound to Pt via carbon atoms, nitrogen-containing aromatic heterocyclic ligands bound to Pt via nitrogen atoms or acyloxy ligands.

$L^1$, $L^2$ and $L^3$ represent single bonds or divalent linking groups. Examples of the divalent linking groups represented by $L^1$, $L^2$ and $L^3$ include alkylene groups (such as methylene, ethylene and propylene), arylene groups (such as phenylene and naphthalenediyl), heteroarylene groups (such as pyridinediyl and thiophenediyl), imino groups (—$NR_L$—) (such as phenylimino groups), oxy groups (—O—), thio groups (—S—), phosphinidene groups (—$PR_L$—) (such as phenylphosphinidene groups), and silylene groups (—$SiR_LR_L'$—) (such as dimethylsilylene and diphenylsilylene groups), and combinations thereof. Herein, each of $R_L$ and $R_L'$ independently represents an alkyl group, an aryl group and the like. These linking groups may further have a substituent.

From the viewpoint of stability and emission quantum efficiency of the complex, $L^1$, $L^2$ and $L^3$ are preferably selected from single bonds, alkylene groups, arylene groups, heteroarylene groups, imino groups, oxy groups, thio groups and silylene groups, more preferably selected from single bonds, alkylene groups, arylene groups and imino groups, even more preferably selected from single bonds, alkylene groups and arylene groups, still more preferably selected from single bonds, methylene groups and phenylene groups, still even more preferably selected from single bonds and disubstituted methylene groups, most preferably selected from single bonds, dimethylmethylene groups, diethylmethylene groups, diisobutylmethylene groups, dibenzylmethylene groups, ethylmethylmethylene groups, methylpropylmethylene groups, isobutylmethylmethylene groups, diphenylmethylene groups, methylphenylmethylene groups, cyclohexanediyl groups, cyclopentanediyl groups, fluorenediyl groups and fluoromethylmethylene groups.

$L_1$ is particularly preferably a dimethylmethylene group, a diphenylmethylene group, or a cyclohexanediyl group, most preferably a dimethylmethylene group.

$L^2$ and $L^3$ are most preferably single bonds.

The platinum complex represented by Formula (C-1) is more preferably one represented by Formula (C-2).

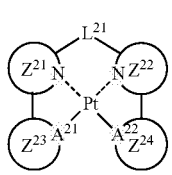

Formula (C-2)

(wherein $L^{21}$ represents a single bond or a divalent linking group, each of $A^{21}$ and $A^{22}$ independently represents a carbon atom or a nitrogen atom, each of $Z^{21}$ and $Z^{22}$ independently represents a nitrogen-containing aromatic heterocycle, and each of $Z^{23}$ and $Z^{24}$ independently represents a benzene ring or an aromatic heterocycle).

An explanation will be given regarding Formula (C-2). $L^{21}$ has the same meaning and preferred range as $L^1$ in Formula (C-1).

Each of $A^{21}$ and $A^{22}$ independently represents a carbon atom or a nitrogen atom. At least one of $A^{21}$ and $A^{22}$ is preferably a carbon atom. From the viewpoint of stability and emission quantum efficiency of the complex, it is preferred that both $A^{21}$ and $A^{22}$ are carbon atoms.

Each of $Z^{21}$ and $Z^{22}$ independently represents a nitrogen-containing aromatic heterocycle. Examples of the nitrogen-containing aromatic heterocycles represented by $Z^{21}$ and $Z^{22}$ include pyridine, pyrimidine, pyrazine, triazine, imidazole, pyrazole, oxazole, thiazole, triazole, oxadiazole, thiadiazole rings and the like. From the viewpoint of stability, emission wavelength control and emission quantum efficiency of the complex, the rings represented by $Z^{21}$ and $Z^{22}$ are preferably pyridine, pyrazine, imidazole and pyrazole rings, more preferably pyridine, imidazole and pyrazole rings, even more preferably pyridine and pyrazole rings, particularly preferably pyridine rings.

The nitrogen-containing aromatic heterocycles represented by $Z^{21}$ and $Z^{22}$ may have substituents. The substituents on the carbon atoms may be those exemplified in the group A of substituents and the substituents on the nitrogen atoms may be those exemplified in the group B of substituents. The substituents on the carbon atoms are preferably alkyl groups, perfluoroalkyl groups, aryl groups, aromatic heterocyclic groups, dialkylamino groups, diarylamino groups, alkoxy groups, cyano groups and fluorine atoms. The substituents are suitably selected for emission wavelength or potential control. For shorter emission wavelengths, electron donating groups, fluorine atoms and aromatic cyclic groups are preferred and, for example, alkyl groups, dialkylamino groups, alkoxy groups, fluorine atoms, aryl groups, aromatic heterocyclic groups and the like are selected. For longer emission wavelengths, electron attracting groups are preferred and, for example, cyano groups, perfluoroalkyl groups and the like are selected. The substituents on the nitrogen atoms are preferably alkyl, aryl and aromatic heterocyclic groups. From the viewpoint of stability of the complex, alkyl and aryl groups are preferred. The substituents may be linked to each other to form a condensed ring. Examples of such condensed rings include benzene, pyridine, pyrazine, pyridazine, pyrimidine, imidazole, oxazole, thiazole, pyrazole, thiophene, furan rings and the like.

Each of $Z^{23}$ and $Z^{24}$ independently represents a benzene ring or an aromatic heterocycle. Examples of the nitrogen-containing aromatic heterocycles represented by $Z^{23}$ and $Z^{24}$ include pyridine, pyrimidine, pyrazine, pyridazine, triazine, imidazole, pyrazole, oxazole, thiazole, triazole, oxadiazole, thiadiazole, thiophene, furan rings and the like. From the viewpoint of stability, emission wavelength control and emission quantum efficiency of the complex, the rings represented by $Z^{23}$ or $Z^{24}$ are preferably benzene, pyridine, pyrazine, imidazole, pyrazole and thiophene rings, more preferably benzene, pyridine and pyrazole rings, even more preferably benzene and pyridine rings.

The benzene rings and nitrogen-containing aromatic heterocycles represented by $Z^{23}$ or $Z^{24}$ may have substituents. The substituents on the carbon atoms may be those exemplified in the group A of substituents and the substituents on the nitrogen atoms may be those exemplified in the group B of substituents. The substituents on the carbon atoms are preferably alkyl groups, perfluoroalkyl groups, aryl groups, aromatic heterocyclic groups, dialkylamino groups, diarylamino groups, alkoxy groups, cyano groups and fluorine atoms. The substituents are suitably selected for emission wavelength or potential control. For longer emission wavelengths, electron donating groups and aromatic cyclic groups are preferred and, for example, alkyl, dialkylamino, alkoxy, aryl, aromatic heterocyclic groups and the like are selected. For shorter emission wavelengths, electron attracting groups are preferred and, for example, fluorine atoms, cyano groups, perfluoroalkyl groups and the like are selected. The substituents on the nitrogen atoms are preferably alkyl, aryl and aromatic heterocyclic groups. From the viewpoint of stability of the complex, alkyl and aryl groups are preferred. The substituents may be linked to each other to form a condensed ring. Examples of such condensed rings include benzene, pyridine, pyrazine, pyridazine, pyrimidine, imidazole, oxazole, thiazole, pyrazole, thiophene and furan rings and the like.

A preferred embodiment of the platinum complex represented by Formula (C-2) is a platinum complex represented by Formula (C-4).

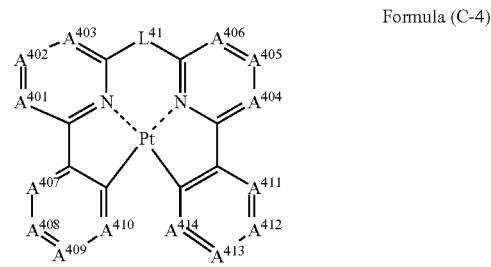

Formula (C-4)

(In Formula (C-4), each of $A^{401}$ to $A^{414}$ independently represents C—R or a nitrogen atom, R represents a hydrogen atom or a substituent, and $L^{41}$ represents a single bond or a divalent linking group).

An explanation will be given regarding Formula (C-4).

Each of $A^{401}$ to $A^{414}$ independently represents C—R or a nitrogen atom. R represents a hydrogen atom or a substituent.

The substituent represented by R may be one exemplified in the group A of substituents.

Each of $A^{401}$ to $A^{406}$ preferably represents C—R. The substituents R in $A^{401}$ to $A^{406}$ may be linked to each other to form a ring. $A^{401}$ to $A^{406}$ may be all C—R. In this case, the substituents R in $A^{402}$ and $A^{405}$ are preferably selected from hydrogen atoms, alkyl groups, aryl groups, amino groups, alkoxy groups, aryloxy groups, fluorine atoms, and cyano groups, more preferably selected from hydrogen atoms, amino groups, alkoxy groups, aryloxy groups and fluorine atoms, particularly preferably selected from hydrogen and fluorine atoms. The substituents R in $A^{401}$, $A^{403}$, $A^{404}$ and $A^{406}$ are preferably selected from hydrogen atoms, alkyl groups, aryl groups, amino groups, alkoxy groups, aryloxy groups, fluorine atoms, and cyano groups, more preferably selected from hydrogen atoms, amino groups, alkoxy groups, aryloxy groups and fluorine atoms, particularly preferably hydrogen atoms.

$L^{41}$ has the same meaning and preferred range as $L^{41}$ in Formula (C-1).

As for $A^{407}$ to $A^{414}$, the number of N (nitrogen atoms) in each of $A^{407}$ to $A^{410}$ and $A^{11}$ to $A^{414}$ is preferably from 0 to 2, more preferably from 0 to 1. When it is intended to shift the emission wavelength to a shorter wavelength, at least one of $A^{408}$ and $A^{412}$ is preferably a nitrogen atom and both of $A^{408}$ and $A^{412}$ are more preferably nitrogen atoms.

When $A^{407}$ to $A^{414}$ are C—R, the substituents R in $A^{408}$ and $A^{412}$ are preferably selected from hydrogen atoms, alkyl groups, perfluoroalkyl groups, aryl groups, amino groups, alkoxy groups, aryloxy groups, fluorine atoms and cyano groups, more preferably selected from hydrogen atoms, perfluoroalkyl groups, alkyl groups, aryl groups, fluorine atoms and cyano groups, particularly preferably selected from hydrogen atoms, phenyl groups, perfluoroalkyl groups and cyano groups. The substituents R in $A^{407}$, $A^{409}$, $A^{411}$ and $A^{413}$ are preferably selected from hydrogen atoms, alkyl groups, perfluoroalkyl groups, aryl groups, amino groups, alkoxy groups, aryloxy groups, fluorine atoms and cyano groups, more preferably selected from hydrogen atoms, perfluoroalkyl groups, fluorine atoms and cyano groups, particularly preferably selected from hydrogen atoms, phenyl groups and fluorine atoms. The substituents R in $A^{410}$ and $A^{414}$ are preferably selected from hydrogen and fluorine atoms, more preferably hydrogen atoms. When any one of $A^{407}$ to $A^{409}$ and $A^{411}$ to $A^{413}$ represents C—R, the substituents R may be linked to each other to form a ring.

A more preferred embodiment of the platinum complex represented by Formula (C-2) is a platinum complex represented by Formula (C-5).

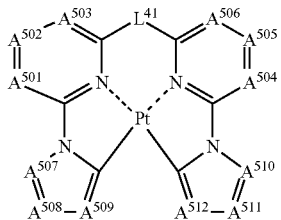

(C-5)

(In Formula (C-5), each of $A^{501}$ to $A^{512}$ independently represents C—R or a nitrogen atom, R represents a hydrogen atom or a substituent, and $L^{51}$ represents a single bond or a divalent linking group).

An explanation will be given regarding Formula (C-5). $A^{501}$ to $A^{506}$ and $L^{51}$ have the same meanings and preferred ranges as $A^{401}$ to $A^{406}$ and $L^{41}$ in Formula (C-4), respectively.

Each of $A^{507}$ to $A^{509}$ and $A^{510}$ to $A^{512}$ independently represents C—R or a nitrogen atom. R represents a hydrogen atom or a substituent. The substituent represented by R may be one exemplified in the group A of substituents. $A^{507}$ to $A^{509}$ and $A^{510}$ to $A^{512}$ may be C—R. In this case, the substituents R are preferably selected from hydrogen atoms, alkyl groups, perfluoroalkyl groups, aryl groups, aromatic heterocyclic groups, dialkylamino groups, diarylamino groups, alkyloxy groups, cyano groups and fluorine atoms, more preferably selected from hydrogen atoms, alkyl groups, perfluoroalkyl groups, aryl groups, dialkylamino groups, cyano groups and fluorine atoms, even more preferably selected from hydrogen atoms, alkyl groups, trifluoromethyl groups and fluorine atoms. If possible, the substituents may be linked to each other to form a condensed ring structure. At least one of $A^{507}$ to $A^{509}$ and $A^{510}$ to and $A^{512}$ is preferably a nitrogen atom, and $A^{510}$ or $A^{507}$ is particularly preferably a nitrogen atom.

Another preferred embodiment of the platinum complex represented by Formula (C-1) is a platinum complex represented by Formula (C-6).

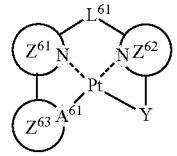

Formula (C-6)

(wherein $L^{61}$ represents a single bond or a divalent linking group, $A^{61}$ represents a carbon or nitrogen atom, each of $Z^{61}$ and $Z^{62}$ independently represents a nitrogen-containing aromatic heterocycle, $Z^{63}$ represents a benzene ring or an aromatic heterocycle, and Y represents an anionic acyclic ligand bound to Pt).

An explanation will be given regarding Formula (C-6). $L^{61}$ has the same meaning and preferred range as $L^1$ in Formula (C-1).

$A^{61}$ represents a carbon or nitrogen atom. From the viewpoint of stability and emission quantum efficiency of the complex, $A^{61}$ is preferably a carbon atom.

$Z^{61}$ and $Z^{62}$ have the same meanings and preferred ranges as $Z^{21}$ and $Z^{22}$ in Formula (C-2), respectively. $Z^{63}$ has the same meaning and preferred range as $Z^{23}$ in Formula (C-2).

Y represents an anionic acyclic ligand bound to Pt. The term "acyclic ligand" means a ligand whose atom bound to Pt does not form a ring. The atom in Y bound to Pt is preferably a carbon, nitrogen, oxygen or sulfur atom, more preferably a nitrogen or oxygen atom, most preferably an oxygen atom.

Y bound to Pt via a carbon atom may be, for example, a vinyl ligand. Y bound to Pt via a nitrogen atom may be, for example, an amino or imino ligand. Y bound to Pt via an oxygen atom may be, for example, an alkoxy, aryloxy, heteroaryloxy, acyloxy, silyloxy, carboxyl, phosphoric acid, sulfonic acid ligand or the like. Y bound to Pt via a sulfur atom may be, for example, an alkylmercapto, arylmercapto, heteroarylmercapto, thiocarboxylic acid ligand or the like.

The ligand represented by Y may have one or more substituents. The substituents may be suitably selected from those exemplified in the group A of substituents. In addition, the substituents may be linked to each other.

The ligand represented by Y is preferably a ligand bound to Pt via an oxygen atom, more preferably an acyloxy, alkyloxy, aryloxy, heteroaryloxy or silyloxy ligand, more preferably an acyloxy ligand.

A more preferred embodiment of the platinum complex represented by Formula (C-6) is a platinum complex represented by Formula (C-7):

Formula (C-7)

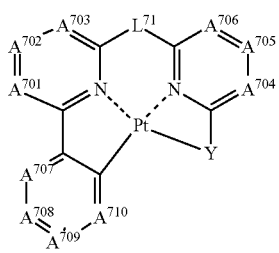

(wherein each of $A^{701}$ to $A^{710}$ independently represents C—R or a nitrogen atom, R represents a hydrogen atom or a substituent, $L^{71}$ represents a single bond or a divalent linking group, and Y represents an anionic acyclic ligand hound to Pt).

An explanation will be given regarding Formula (C-7). $L^{71}$ has the same meaning and preferred range as $L^{61}$ in Formula (C-6). $A^{701}$ to $A^{710}$ have the same meanings and preferred ranges as $A^{401}$ to $A^{410}$ in Formula (C-4), respectively. Y has the same meaning and preferred range as Y in Formula (C-6).

Specific examples of the platinum complex represented by Formula (C-1) include the compounds described in Paragraphs [0143] to [0152], [0157] to [0158] and [0162] to [0168] of Japanese Patent Application Laid-Open No. 2005-310733, the compounds described in Paragraphs [0065] to [0083] of Japanese Patent Application Laid-Open No. 2006-256999, the compounds described in Paragraphs [0065] to [0090] of Japanese Patent Application Laid-Open No. 2006-93542, the compounds described in Paragraphs [0063] to [0071] of Japanese Patent Application Laid-Open No. 2007-73891, the compounds described in Paragraphs [0079] to [0083] of Japanese Patent Application Laid-Open No. 2007-324309, the compounds described in [0065] to [0090] of Japanese Patent Application Laid-Open No. 2006-93542, the compounds described in Paragraphs [0055] to [0071] of Japanese Patent Application Laid-Open No. 2007-96255, and the compounds described in Paragraphs [0043] to [0046] of Japanese Patent Application Laid-Open No. 2006-313796. Other examples include platinum complexes exemplified below.

1-1

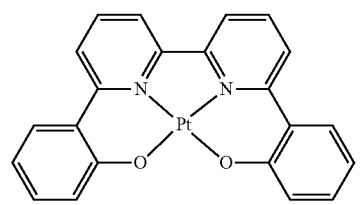

1-2

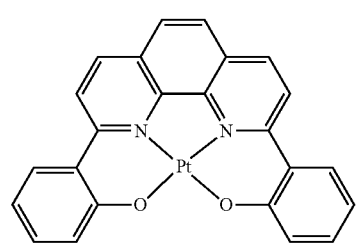

1-3

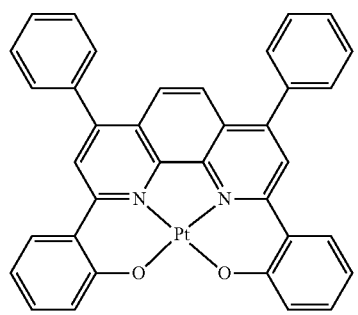

2-0

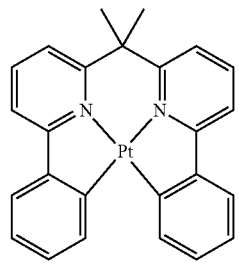

2-1

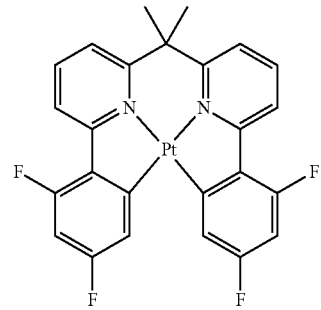

2-2

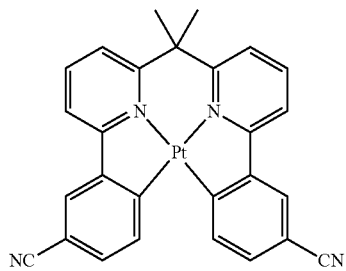

2-3

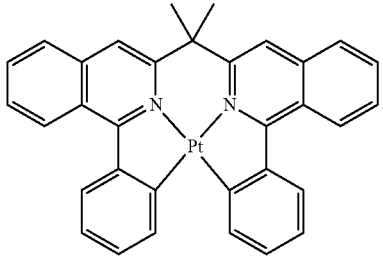

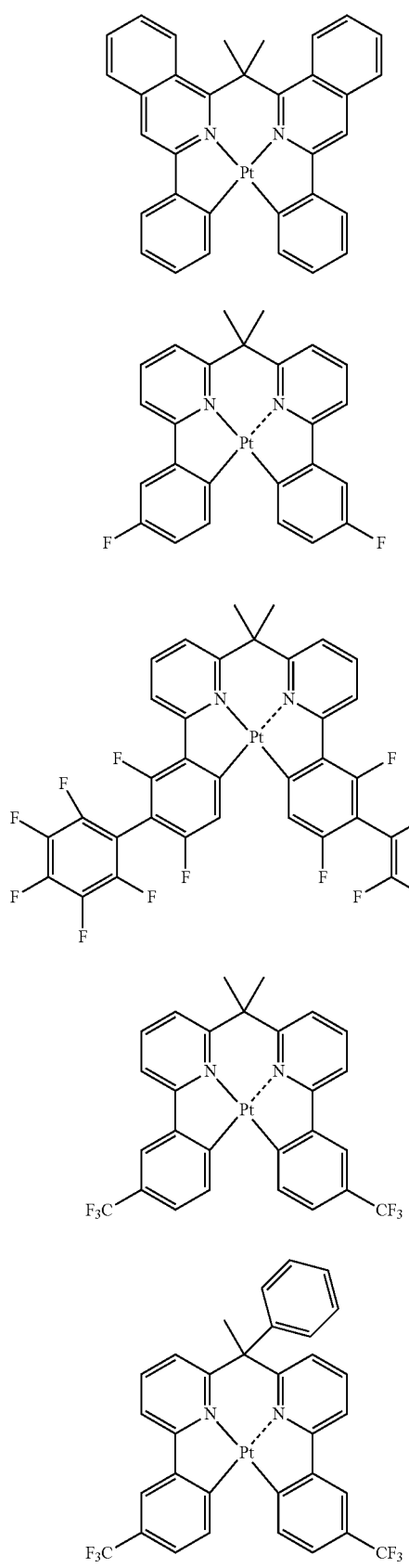
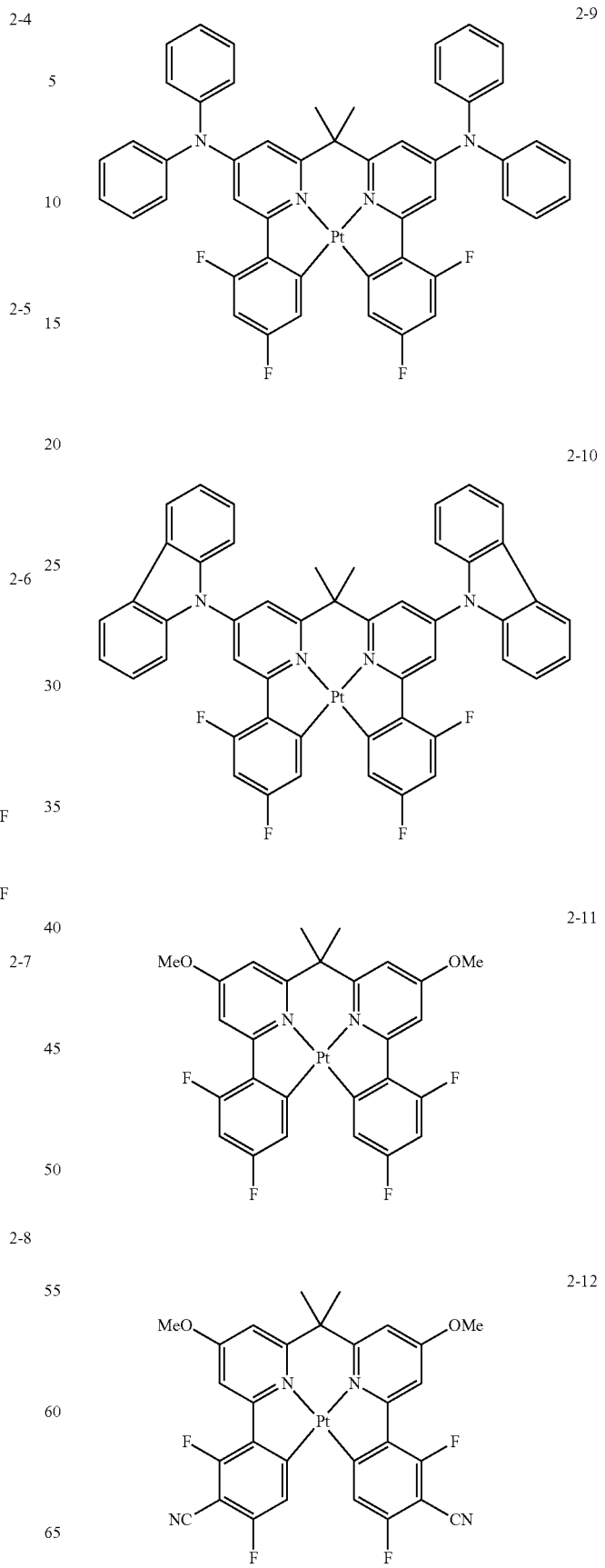

-continued
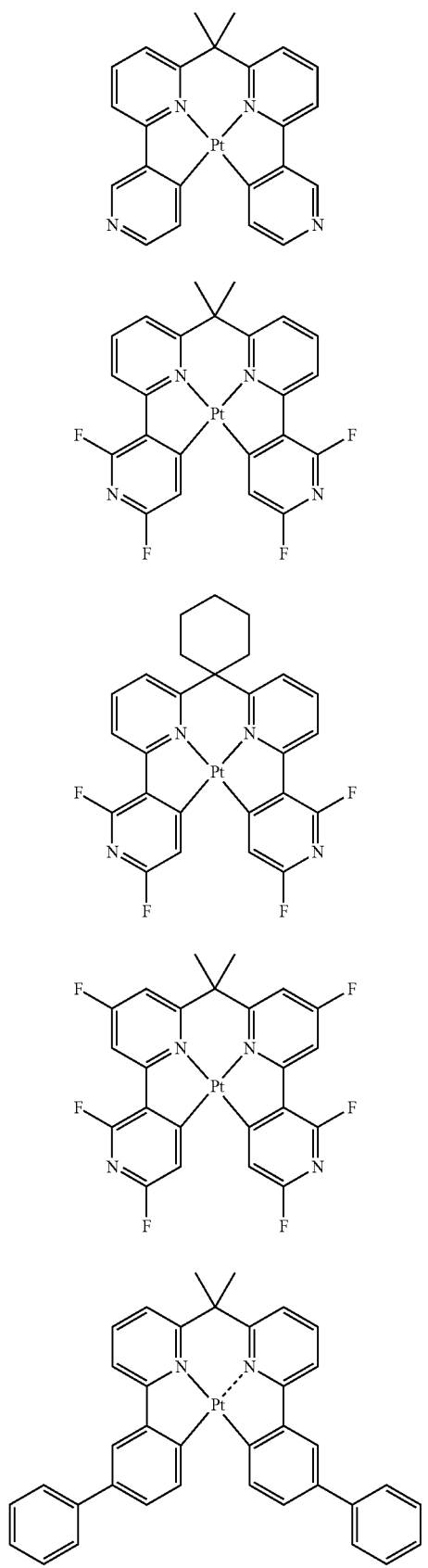
3-1
3-2
3-3
3-4
3-5
-continued
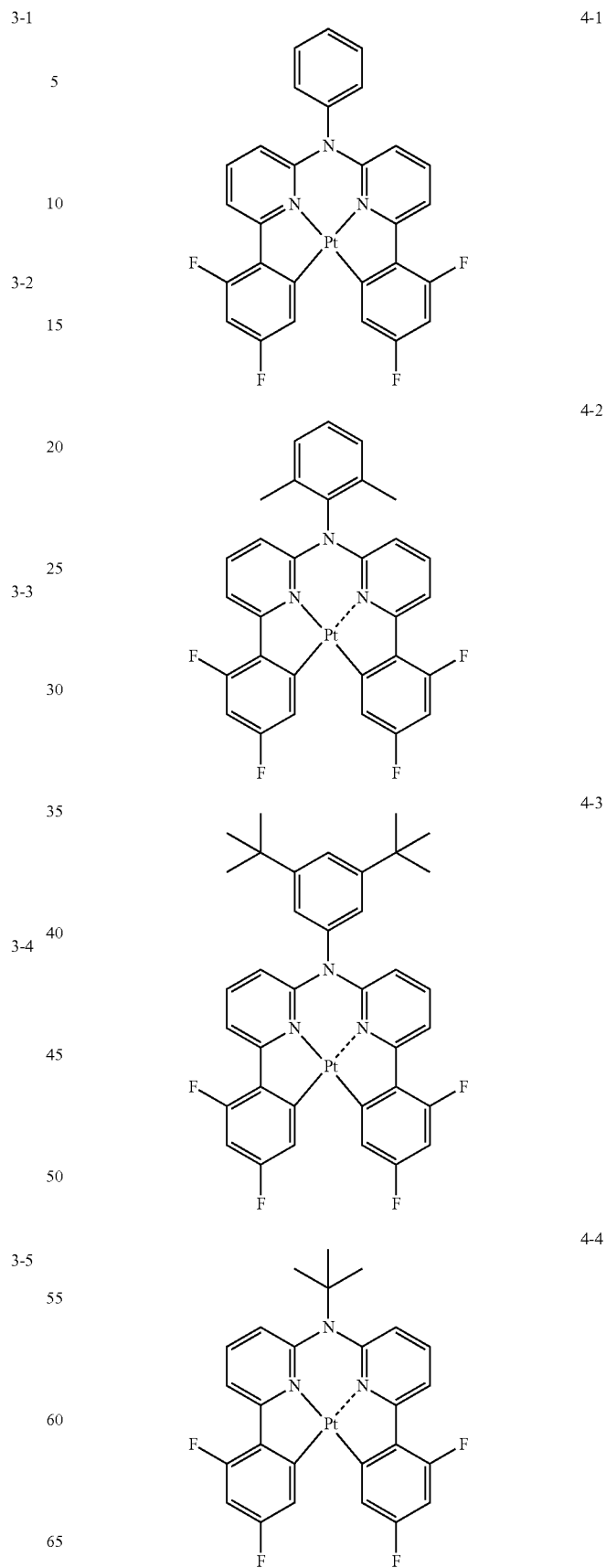
4-1
4-2
4-3
4-4

4-5
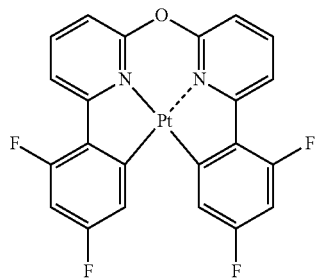
5-1
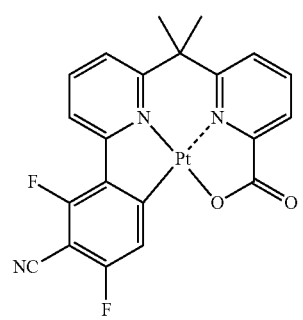
5-2
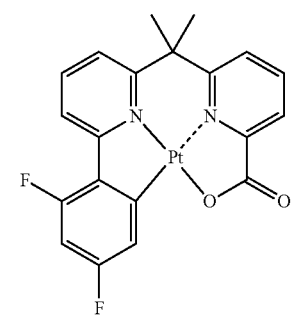
5-3
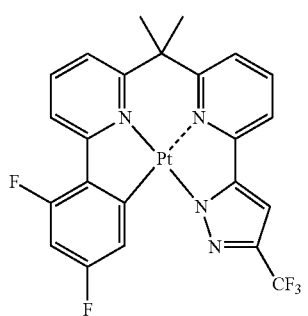
5-5
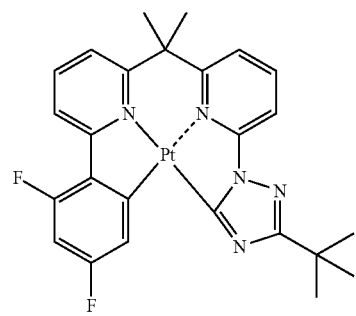
6-1
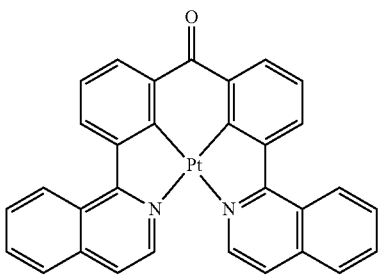
6-2
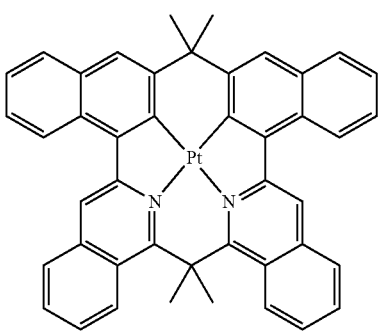
6-3
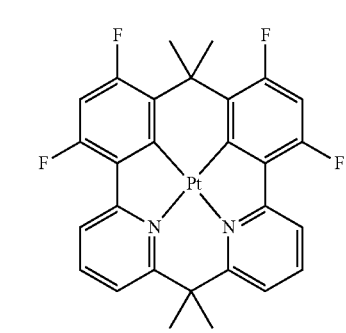
6-4
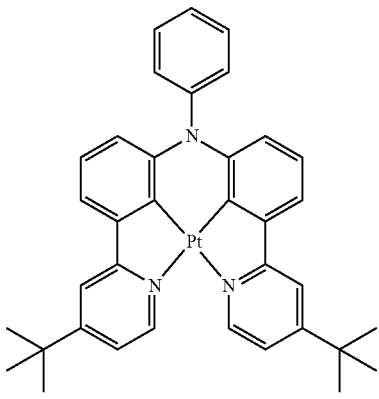

6-6
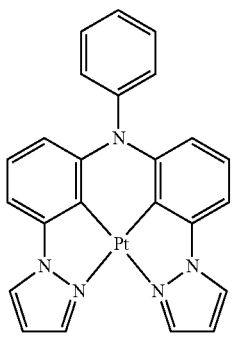
7-1
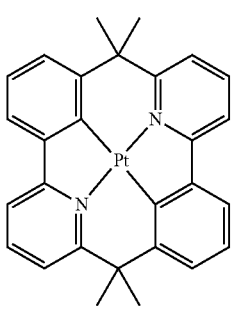
7-2
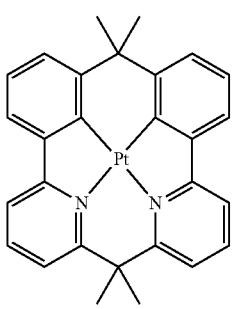
7-3
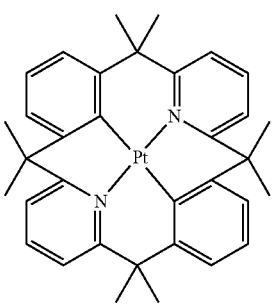
7-4
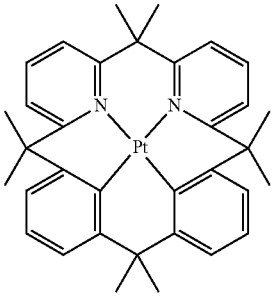
7-5
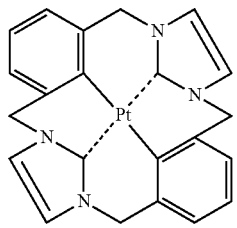
8-1
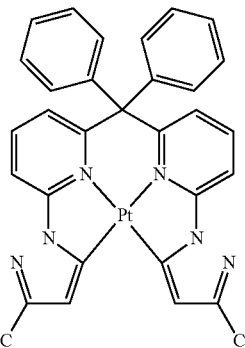
8-2
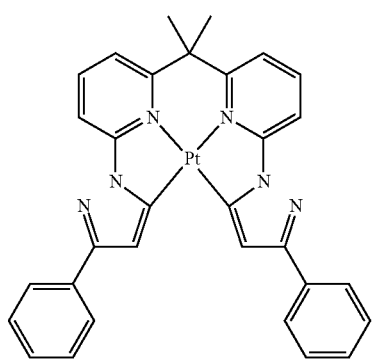
8-3
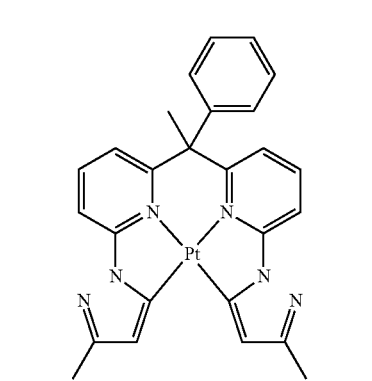
8-4
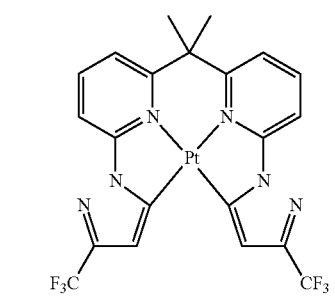

8-5
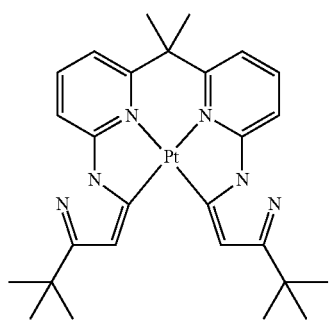
8-6
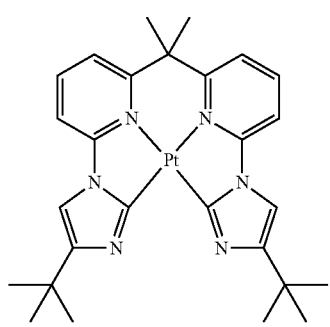
8-8
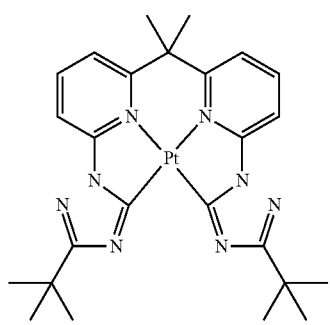
8-9
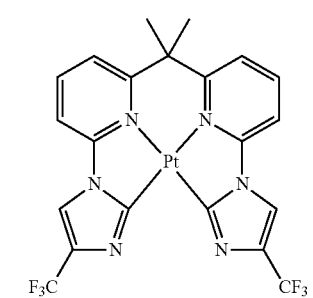
8-10
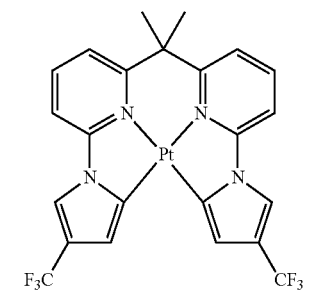
8-11
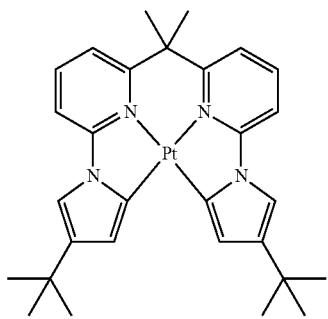
9-1
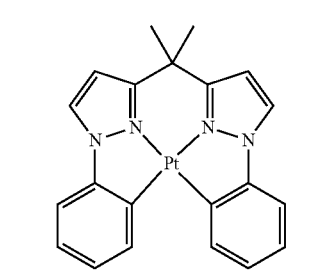
9-2
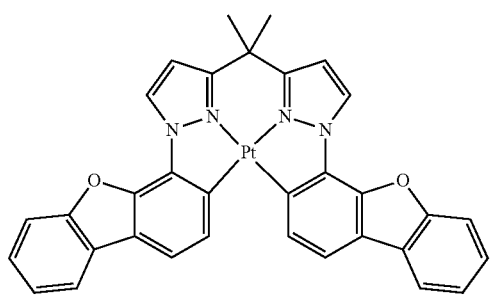
9-3
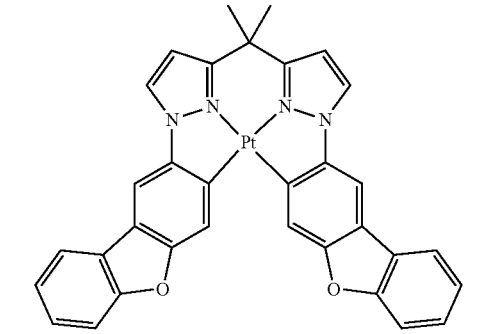
9-4
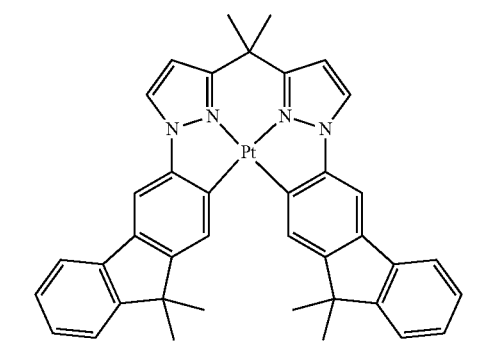

9-5
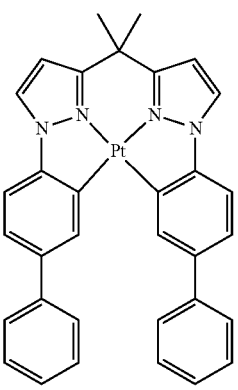
9-6
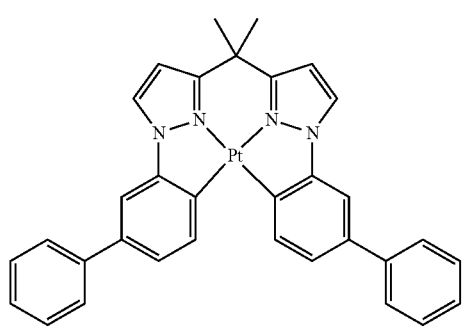
9-7
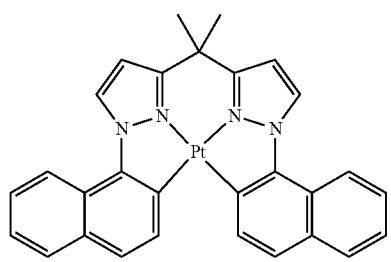
9-8
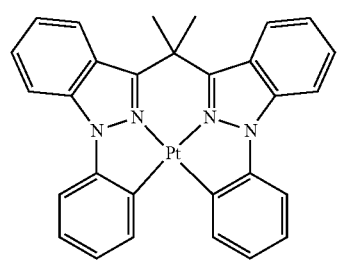
9-9
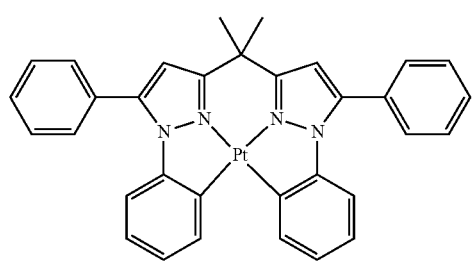
9-10
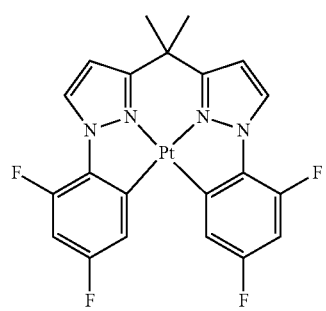
9-11
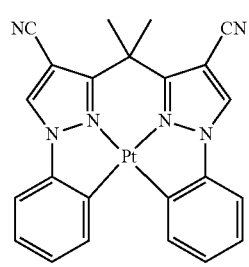
9-12
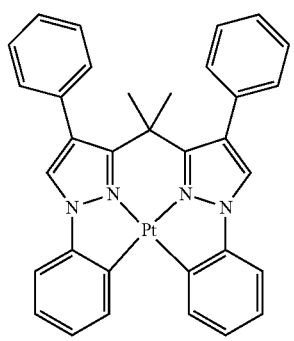
9-13
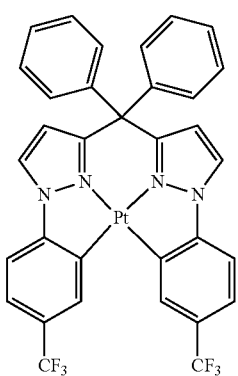

9-14
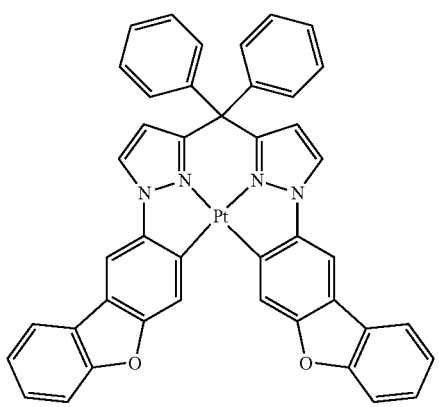

9-15
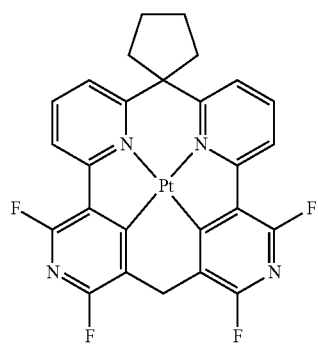

9-16
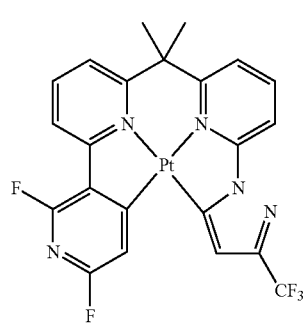

9-17
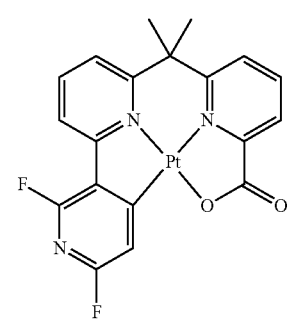

9-18
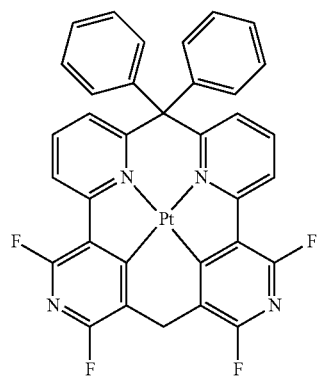

9-19
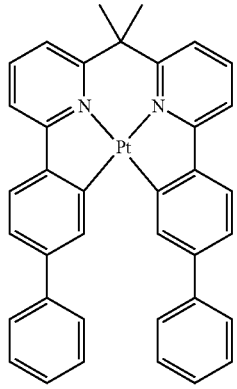

The platinum complex compound represented by Formula (C-1) can be synthesized by various methods, for example: the methods described at page 789, left column, line 53 to right column, line 7 and at page 790, left column, lines 18 to 38 to right column, lines 19 to 30 in G. R. Newkome et al. Journal of Organic Chemistry, 53, 786 (1988), and combinations thereof; and the method described at page 2752, lines 26 to 35 in H. Lexy et al. Chemische Berichte, 113, 2749 (1980).

For example, the platinum complex compound can be obtained by reacting a corresponding ligand or a dissociation product thereof with a corresponding metal compound at a temperature not higher than room temperature or under heating (microwave heating is also effective in addition to ordinary heating) in a solvent (for example, a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent, water or the like) or without a solvent in the presence of a base (for example, an inorganic or organic base, such as sodium methoxide, potassium t-butoxide, triethylamine or potassium carbonate) or in the absence of a base.

In the present invention, the content of the compound represented by Formula (C-1) in the light emitting layer is preferably from 1 to 30% weight, more preferably from 3 to 25% by mass, even more preferably from 5 to 20% by mass.

The iridium complex is preferably one represented by Formula (T-1).

[Compound Represented by Formula (T-1)]

An explanation will be given regarding the compound represented by Formula (T-1).

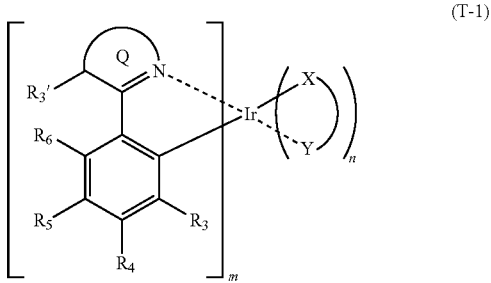

(T-1)

(In Formula (T-1), each of $R_3'$, $R_3$, $R_4$, $R_5$ and $R_6$ independently represents a hydrogen atom, an alkyl group, a cycloalkyl group, an alkenyl group, an alkynyl group, —CN, a perfluoroalkyl group, a trifluorovinyl group, —CO$_2$R$_T$, —C(O)R$_T$, —N(R$_T$)$_2$, —NO$_2$, —OR$_T$, a fluorine atom, an aryl group or a heteroaryl group and may further have a substituent Z.

Q is a 5- or 6-membered aromatic heterocycle or a condensed aromatic heterocycle including one or more nitrogen atoms.

Any two adjacent groups selected from $R_3$, $R_4$, $R_5$ and $R_6$ may be bonded together to form a condensed 4- to 7-membered ring. The condensed 4- to 7-membered ring is a cycloalkyl, aryl or heteroaryl ring and may further have a substituent Z.

$R_3'$ and $R_6$ may be linked to each other through a linking group selected from —C(R$_T$)$_2$—C(R$_T$)$_2$—, —CR$_T$=CR$_T$—, —C(R$_T$)$_2$—, —O—, —NR$_T$—, —O—C(R$_T$)$_2$—, —NR$_T$—C(R$_T$)$_2$— and —N=CR$_T$— to form a ring. Each R$_T$ independently represents a hydrogen atom, an alkyl group, an alkenyl group, an alkynyl group, a heteroalkyl group, an aryl group or a heteroaryl group and may further have a substituent Z.

Each Z independently represents a fluorine atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R'. Each R' independently represents a hydrogen atom, an alkyl group, a perfluoroalkyl group, an alkenyl group, an alkynyl group, a heteroalkyl group, an aryl group or a heteroaryl group. (X—Y) represents a ligand. m represents an integer from 1 to 3 and n represents an integer from 0 to 2, where the sum of m+n is 3).

The alkyl groups may have a substituent and may be saturated or unsaturated. The substituent may be, for example, the substituent Z. Each of the alkyl groups represented by $R_3'$, $R_3$, $R_4$, $R_5$ and $R_6$ is one that preferably has 1 to 8 carbon atoms, more preferably 1 to 6 carbon atoms, for example, a methyl group, an ethyl group, an isopropyl group, a t-butyl group or the like.

The cycloalkyl groups may have a substituent and may be saturated or unsaturated. The substituent may be, for example, the substituent Z. Each of the cycloalkyl groups represented by $R_3'$, $R_3$, $R_4$, $R_5$ and $R_6$ is preferably a 4- to 7-membered cycloalkyl group, more preferably a $C_5$-$C_6$ cycloalkyl group, for example, a cyclopentyl group, a cyclohexyl group or the like.

Each of the alkenyl groups represented by $R_3'$, $R_3$, $R_4$, $R_5$ and $R_6$ is one that preferably has 2 to 30 carbon atoms, more preferably 2 to 20 carbon atoms, particularly preferably 2 to 10 carbon atoms, for example, vinyl, allyl, 1-propenyl, 1-isopropenyl, 1-butenyl, 2-butenyl, 3-pentenyl or the like.

Each of the alkynyl groups represented by $R_3'$, $R_3$, $R_4$, $R_5$, $R_6$ is one that preferably has 2 to 30 carbon atoms, more preferably 2 to 20 carbon atoms, particularly preferably 2 to 10 carbon atoms, for example, ethynyl, propargyl, 1-propynyl 3-pentynyl or the like.

The perfluoroalkyl groups represented by $R_3'$, $R_3$, $R_4$, $R_5$ and $R_6$ may be those in which all hydrogen atoms of the above-described alkyl groups are replaced by fluorine atoms.

The aryl groups represented by $R_3'$, $R_3$, $R_4$, $R_5$ and $R_6$ are preferably $C_6$-$C_{30}$ substituted or unsubstituted aryl groups, for example, phenyl, tolyl, naphthyl groups and the like.

The heteroaryl groups represented by $R_3'$, $R_3$, $R_4$, $R_5$ and $R_6$ are preferably $C_5$-$C_8$ heteroaryl groups, more preferably 5- or 6-membered substituted or unsubstituted heteroaryl groups, for example, pyridyl, pyrazinyl, pyridazinyl, pyrimidinyl, triazinyl, quinolinyl, isoquinolinyl, quinazolinyl, cinnolinyl, phthalazinyl, quinoxalinyl, pyrrolyl, indolyl, furyl, benzofuryl, thienyl, benzothienyl, pyrazolyl, imidazolyl, benzimidazolyl, triazolyl, oxazolyl, benzoxazolyl, thiazolyl, benzothiazolyl, isothiazolyl, benzisothiazolyl, thiaziazolyl, isoxazolyl, benzoisoxazolyl, pyrrolidinyl, piperidinyl, piperazinyl, imidazolidinyl, thiazolinyl, sulforanyl, carbazolyl, dibenzofuryl, dibenzothienyl, pyridoindolyl groups and the like. The heteroaryl groups are preferably pyridyl, pyrimidinyl, imidazolyl and thienyl groups, more preferably pyridyl and pyrimidinyl groups.

$R_3'$, $R_3$, $R_4$, $R_5$ and $R_6$ are preferably selected from hydrogen atoms, alkyl groups, cyano groups, perfluoroalkyl groups, dialkylamino groups, fluorine atoms, aryl groups and heteroaryl groups, more preferably selected from hydrogen atoms, alkyl groups, cyano groups, trifluoromethyl groups, fluorine atoms and aryl groups, even more preferably selected from hydrogen atoms, alkyl groups and aryl groups. The substituent Z is preferably an alkyl group, an alkoxy group, a fluorine atom, a cyano group or a dialkylamino group, more preferably a hydrogen atom.

Any two adjacent groups selected from $R_3$, $R_4$, $R_5$ and $R_6$ may be bonded together to form a condensed 4- to 7-membered ring, the corresponding condensed 4- to 7-membered ring is a cycloalkyl, aryl or heteroaryl ring, and the corresponding condensed 4- to 7-membered ring may further have a substituent Z. The definitions and preferred ranges of the cycloalkyl, aryl and heteroaryl rings are the same as those of the cycloalkyl, aryl and heteroaryl groups defined by $R_3'$, $R_3$, $R_4$, $R_5$ and $R_6$.

Examples of the aromatic heterocyclic ring represented by the ring Q include pyridine, pyrazine, pyrimidine, pyrazole, imidazole, triazole, oxazole, oxadiazole, thiazole, thiadiazole rings and the like. Pyridine and pyrazine rings are preferred, and pyridine rings are more preferred.

Examples of the condensed aromatic heterocycle represented by the ring Q include quinoline, isoquinoline and quinoxaline rings. Quinoline and isoquinoline rings are preferred, and quinoline rings are more preferred.

m is preferably from 1 to 3, more preferably 2 or 3. That is, n is preferably 0 or 1. One or two kinds of ligands are preferably used to constitute the complex. One kind of ligand is more preferred. When a reactive group is introduced into the complex molecule, it is preferred in terms of ease of synthesis that the complex consists of two kinds of ligands.

The metal complex represented by Formula (T-1) may be composed of a combination of a ligand represented by Formula (T-1-A) or its tautomer and a ligand represented by Formula (X—Y) or its tautomer. Alternatively, all ligands of the metal complex represented by Formula (T-1) may be composed of the ligand represented by Formula (T-1-A) or its tautomer only.

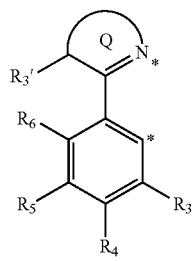
(T-1-A)

($R_3'$, $R_3$, $R_4$, $R_5$, $R_6$ and Q in Formula (T-1-A) have the same meanings as $R_3'$, $R_3$, $R_4$, $R_5$, $R_6$ and Q in Formula (T-1), respectively. * represents the positions coordinated to iridium).

A ligand (also referred to as a 'coordination compound') publicly known to those skilled in the art as the so-called ligand used to form metal complexes may be used as the ligand represented by (X—Y) according to the intended need.

Various ligands are known to form metal complexes, and examples there include halogen ligands (preferably chlorine ligands), nitrogen-containing heteroaryl ligands (such as bipyridyl and phenanthroline) and diketone ligands (such as acetylacetone), which are described, for example, in H. Yersin, "Photochemistry and Photophysics of Coordination Compounds" published by Springer-Verlag Company in 1987, and Akio Yamamoto, "Organometallic Chemistry—Basis and Application—" published by Shokabo Company in 1982. The ligand represented by (X—Y) is preferably a diketone or a picolinic acid derivative. From the viewpoint of achieving high stability and luminous efficiency of the complex, most preferred is acetylacetonate (acac) shown below.

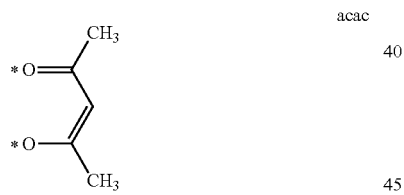
acac

* represents the positions coordinated to iridium.

Specific examples of the ligand represented by (X—Y) include the following ligands, but the present invention is not limited thereto).

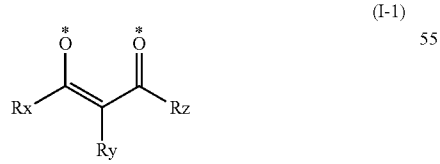
(I-1)

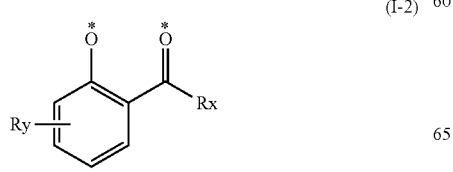
(I-2)

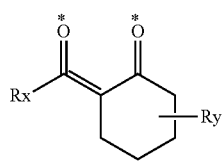
(I-3)

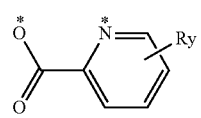
(I-4)

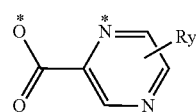
(I-5)

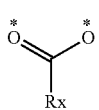
(I-6)

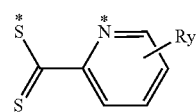
(I-7)

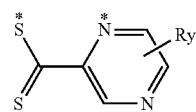
(I-8)

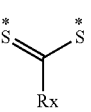
(I-9)

(I-10) 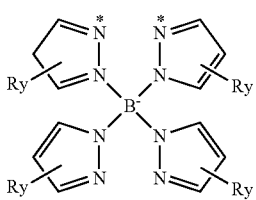

(I-11) 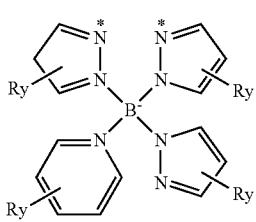

(I-12) 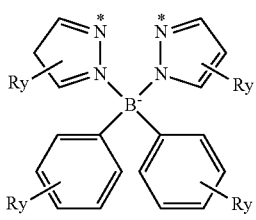

(I-13) 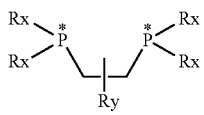

(I-14) 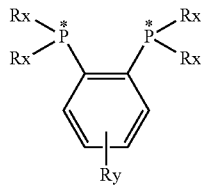

In the examples of the ligand represented by (X—Y), * represents the positions coordinated to iridium in Formula (T-1). Each of Rx, Ry and Rz independently represents a hydrogen atom or a substituent. The substituent may be one selected from the group A of substituents.

Preferably, each of Rx and Rz is independently preferably selected from alkyl groups, perfluoroalkyl groups, fluorine atoms and aryl groups, more preferably selected from $C_1$-$C_4$ alkyl groups, $C_1$-$C_4$ perfluoroalkyl groups, fluorine atoms and substituted or unsubstituted phenyl groups, most preferably selected from methyl groups, ethyl groups, trifluoromethyl groups, fluorine atoms and phenyl groups. Ry is preferably selected from hydrogen atoms, alkyl groups, perfluoroalkyl groups, fluorine atoms and aryl groups, more preferably selected from hydrogen atoms, $C_1$-$C_4$ alkyl groups and substituted or unsubstituted phenyl groups, and most preferably selected from hydrogen atoms and methyl groups. Since these ligands are not thought to be sites that transport charges in the device or where electrons are localized by excitation, Rx, Ry and Rz may be chemically stable substituents and do not affect the effects of the present invention.

The complex is preferably (I-1), (I-4) or (I-5), most preferably (I-1), because of its ease of synthesis.

From the viewpoint of achieving high stability and luminous efficiency of the complex in the present invention, the ligand represented by (X—Y) is most preferably acetylacetonate (acac) shown above.

* represents the positions coordinated to iridium.

The complex having the ligand can be synthesized using a corresponding ligand precursor in accordance with known synthesis examples. For example, the complex may be synthesized using commercially available difluoroacetylacetone in the same manner as the method described at page 46 of International Publication No. 2009-073245, which is shown below.

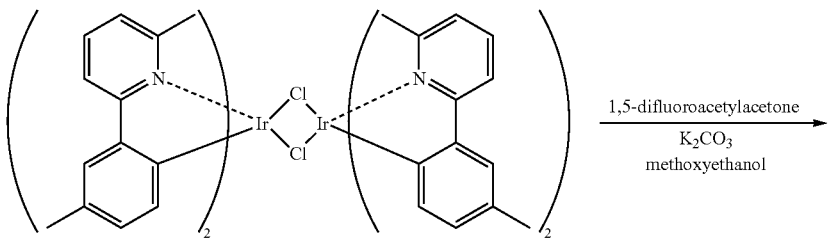

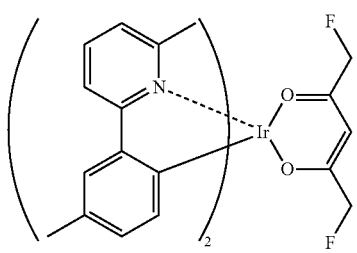

As the ligand, there may also be used a monoanionic ligand represented by Formula (I-15).

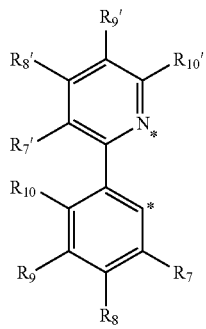

(I-15)

$R_7$ to $R_{10}$ in Formula (I-15) have the same meanings and preferred ranges as $R_3$ to $R_6$ in Formula (T-1), respectively. $R_7'$ to $R_{10}'$ in Formula (I-15) have the same meanings and preferred ranges as $R_3'$ in Formula (T-1). * represents the positions coordinated to iridium in Formula (T-1).

The compound represented by Formula (T-1) is preferably a compound represented by Formula (T-2).

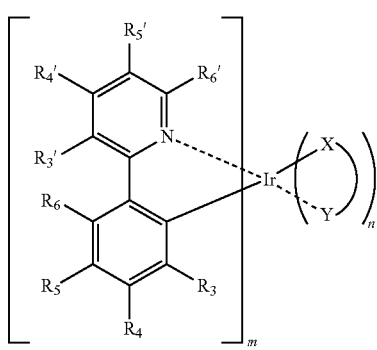

(T-2)

(In Formula (T-2), each of $R_3'$ to $R_6'$ and $R_3$ to $R_6$ independently represents a hydrogen atom, an alkyl group, a cycloalkyl group, an alkenyl group, an alkynyl group, —CN, a perfluoroalkyl group, a trifluorovinyl group, —CO$_2R_T$, —C(O)$R_T$, —N($R_T$)$_2$, —NO$_2$, —O$R_T$, a fluorine atom, an aryl group or a heteroaryl group and may further have a substituent Z.

Any two adjacent groups selected from $R_3$, $R_4$, $R_5$ and $R_6$ are bonded together to form a 4- to 7-membered ring, and the corresponding 4- to 7-membered ring may further have a substituent Z.

$R_3'$ and $R_6$ may be linked to each other through a linking group selected from —C(Rr)$_2$—C(Rr)$_2$—, —CR$_T$=CR$_T\alpha$, —C($R_T$)$_2$—, —O—, —NR$_T$—, —O—C($R_T$)$_2$—, —NR$_T$—C($R_T$)$_2$— and —N=CR$_T$— to form a ring.

Each $R_T$ independently represents a hydrogen atom, an alkyl group, an alkenyl group, an alkynyl group, a heteroalkyl group, an aryl group or a heteroaryl group and may further have a substituent Z.

Each Z independently represents a fluorine atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R'. Each R' independently represents a hydrogen atom, an alkyl group, a perhaloalkyl group, an alkenyl group, an alkynyl group, a heteroalkyl group, an aryl group or a heteroaryl group.

(X—Y) represents a ligand. m represents an integer from 1 to 3 and n represents an from 0 to 2, where the sum of m+n is 3).

$R_3'$, $R_3$ to $R_6$, (X—Y), m and n in Formula (T-2) have the same preferred ranges as $R_3'$, $R_3$ to $R_6$, (X—Y), m and n in Formula (T-1), respectively.

$R_4'$ is preferably a hydrogen atom, an alkyl group, an aryl group or a fluorine atom, more preferably a hydrogen atom.

$R_5'$ and $R_6'$ represent hydrogen atoms or are preferably bonded together to form a 4- to 7-membered cyclic group, and the corresponding 4- to 7-membered cyclic group is more preferably cycloalkyl, cycloheteroalkyl, aryl or heteroaryl, even more preferably aryl.

The substituents Z in $R_4'$ to $R_6'$ are preferably selected from alkyl groups, alkoxy groups, fluorine atoms, cyano groups, alkylamino groups and diarylamino groups, more preferably selected from alkyl groups.

A preferred embodiment of the compound represented by Formula (T-2) is the case where any two adjacent groups selected from $R_3'$, $R_4'$, $R_5'$, $R_6'$, $R_3$, $R_4$, $R_5$ and $R_6$ in Formula (T-2) are not bonded together to form a condensed ring.

A preferred embodiment of the compound represented by Formula (T-2) is a compound represented by Formula (T-3).

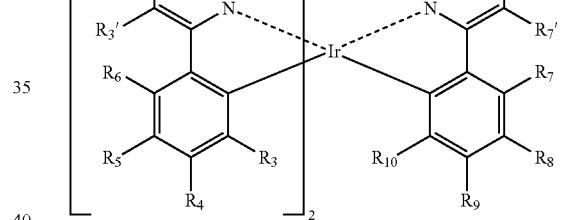

(T-3)

$R_3'$ to $R_6'$ and $R_3$ to $R_6$ in Formula (T-3) have the same meanings and preferred ranges as $R_3'$ to $R_6'$ and $R_3$ to $R_6$ in Formula (T-2), respectively.

$R_7$ to $R_{10}$ have the same meanings and preferred ranges as $R_3$ to $R_6$. $R_7'$ to $R_{10}'$ have the same meanings and preferred ranges as $R_3'$ to $R_6'$.

A preferred embodiment of the compound represented by Formula (T-2) is a compound represented by Formula (T-4).

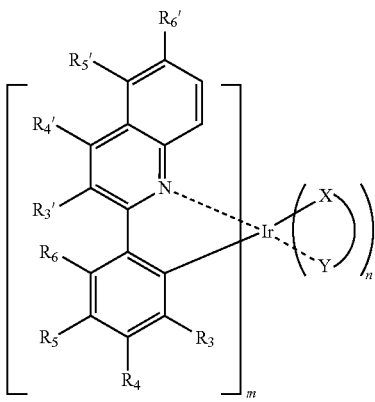

(T-4)

$R_3'$ to $R_6'$, $R_3$ to $R_6$, (X—Y), m and n in Formula (T-4) have the same meanings and preferred ranges as $R_3'$ to $R_6'$, $R_3$ to $R_6$, (X—Y), m and n in Formula (T-2), respectively. It is particularly preferred that none to two of $R_3'$ to $R_6'$ and $R_3$ to $R_6$ are alkyl or phenyl groups and the others are all hydrogen atoms. It is more preferred that one or two of $R_3'$ to $R_6'$ and $R_3$ to $R_6$ are alkyl groups and the others are all hydrogen atoms.

A preferred embodiment of the compound represented by Formula (T-2) is a compound represented by Formula (T-5).

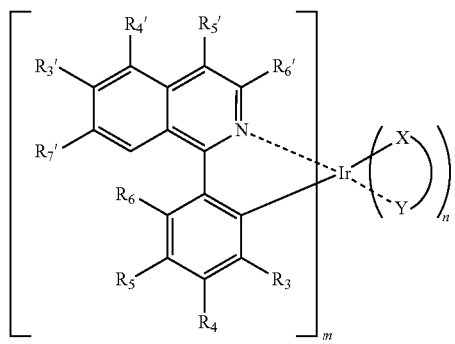

(T-5)

$R_3'$ to $R_7'$, $R_3$ to $R_6$, (X—Y), m and n in Formula (T-5) have the same meanings and preferred ranges as $R_3'$ to $R_6''$, $R_3$ to $R_6$, (X—Y), m and n in Formula (T-2), respectively.

A preferred embodiment of the compound represented by Formula (T-1) is a compound represented by Formula (T-6).

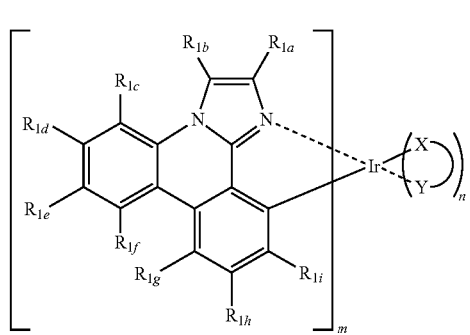

(T-6)

$R_{1a}$ to $R_{1i}$ in Formula (T-6) have the same meanings and preferred ranges as $R_3$ to $R_6$ in Formula (T-1). It is particularly preferred that none to two of $R_{1a}$ to $R_{1i}$ are alkyl or aryl groups and the others are all hydrogen atoms. The definitions and preferred ranges of (X—Y), m and n in Formula (T-6) are the same as those of (X—Y), m and n in Formula (T-1), respectively.

Preferred specific examples of the compound represented by Formula (T-1) include, but are not limited to, the following compounds.

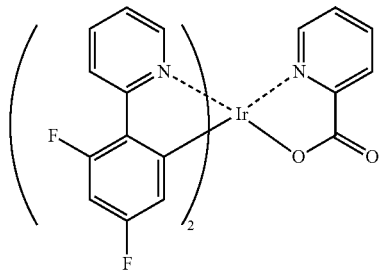

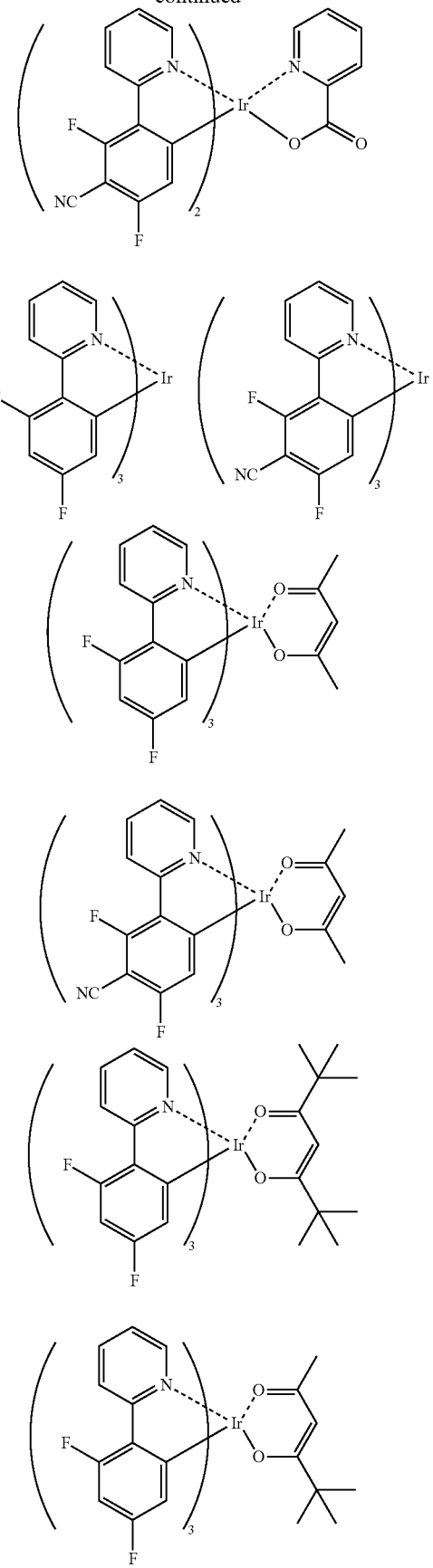

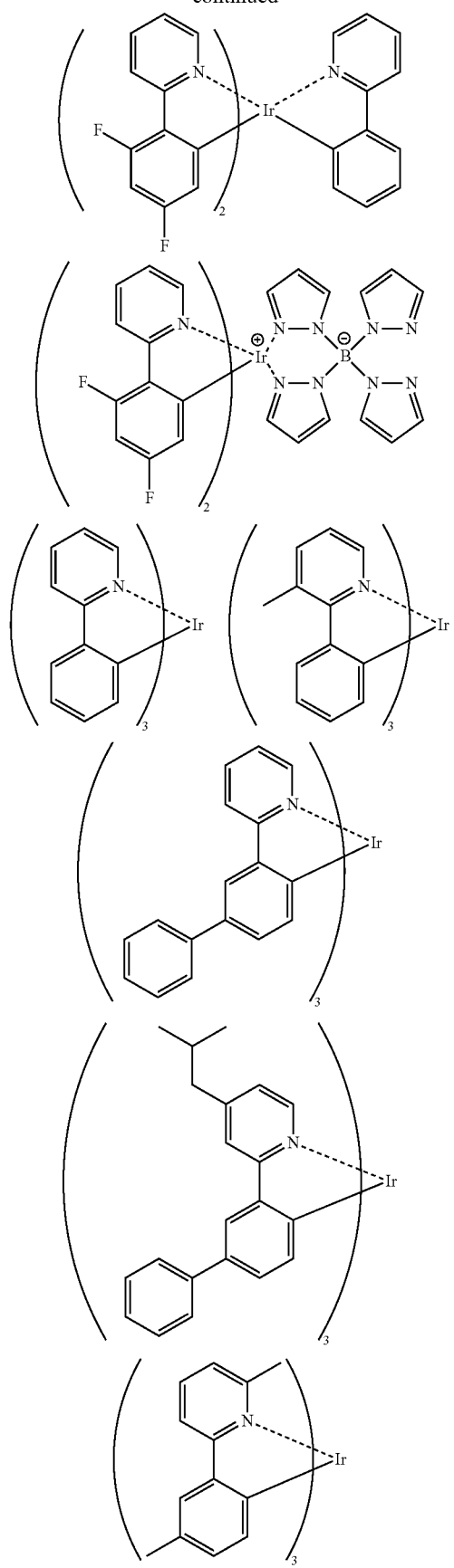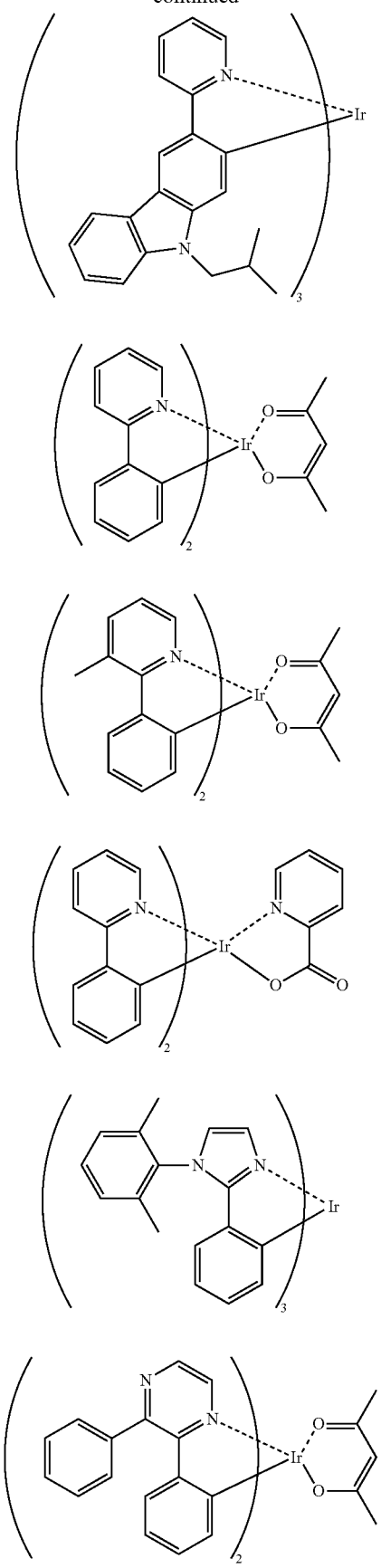

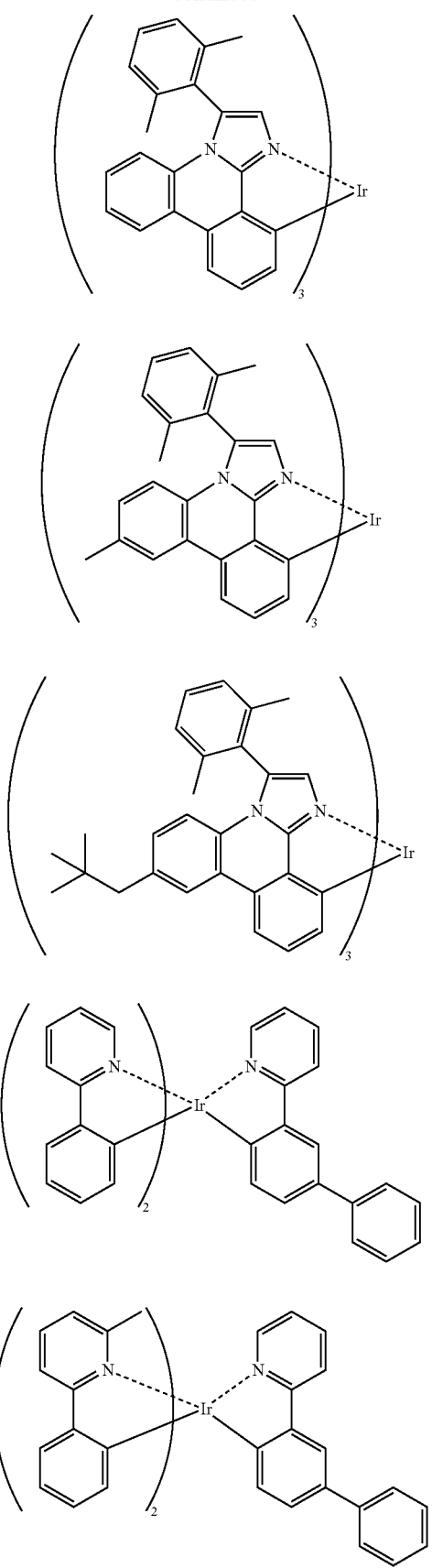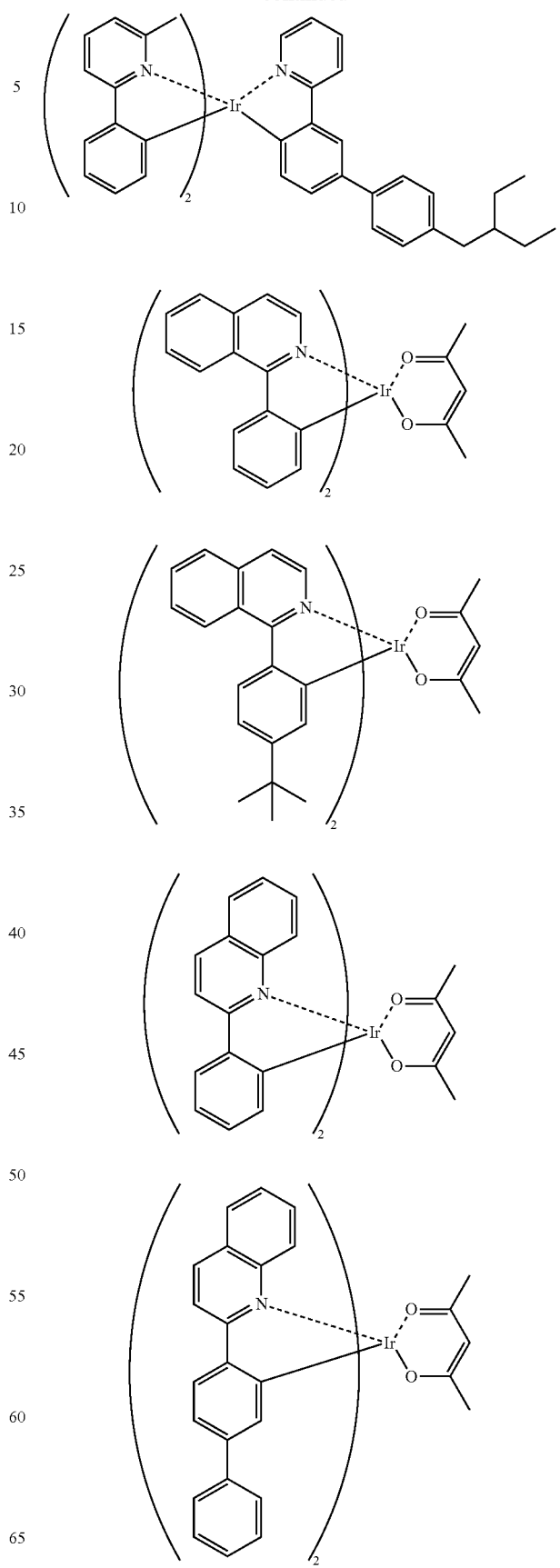

-continued

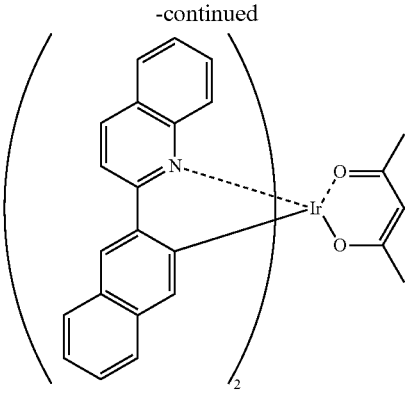
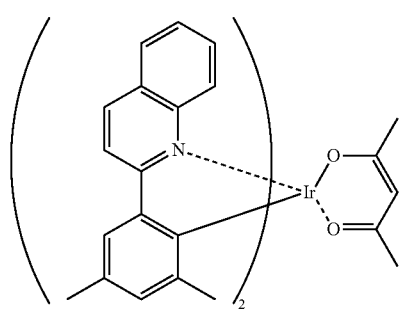
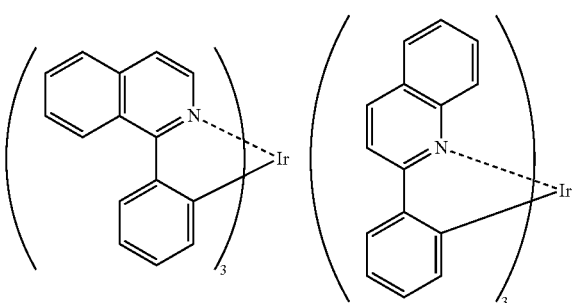
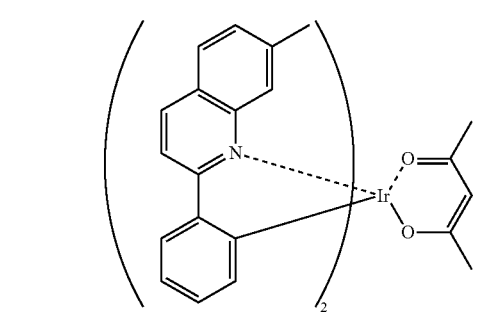
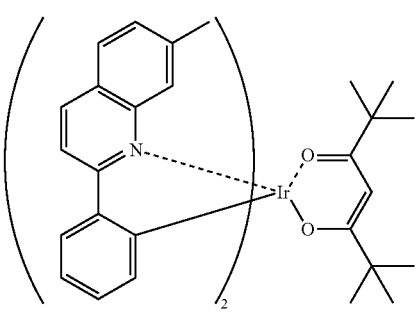

-continued

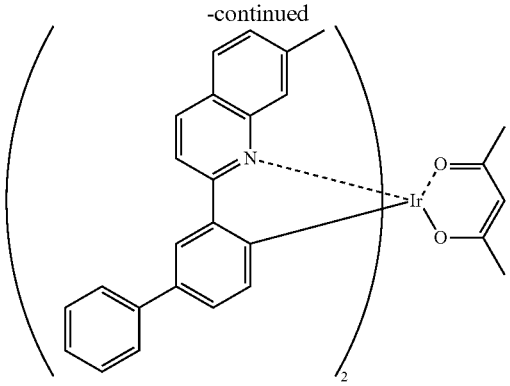
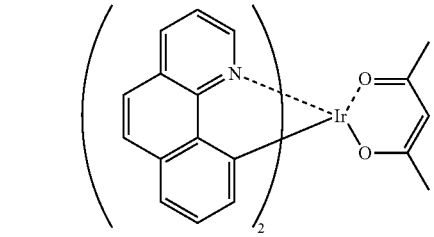

The compounds exemplified as the compound represented by Formula (T-1) can be synthesized by various methods, for example, the method described in Japanese Patent Application Laid-Open No. 2009-99783 and the method described in U.S. Pat. No. 7,279,232. It is preferred to purify the compounds by a suitable process, such as column chromatography or recrystallization, followed by sublimation. The purification by sublimation enables effective removal of inorganic salts or residual solvents as well as separation of the organic impurities. In addition, it is preferred to perform the purification procedure by recrystallization and sublimation several times.

The compound represented by Formula (T-1) is contained in the light emitting layer but is not limited to this use. The compound represented by Formula (T-1) may be contained in any constituent layer of the organic layer.

In addition to the compound represented by Formula (T-1), a compound represented by Formula (T-7) or a compound having a carbene ligand may also be used as the iridium complex.

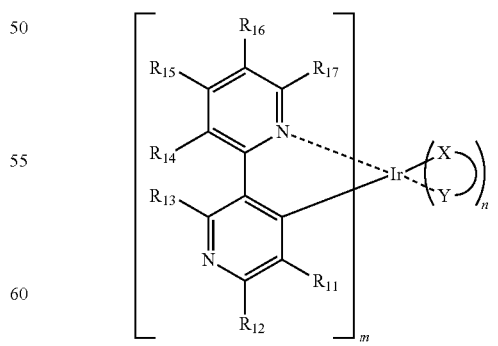

(T-7)

In Formula (T-7), $R_{11}$ to $R_{17}$ have the same meanings and preferred ranges as $R_3$ to $R_6$ in Formula (T-2). (X—Y), n and m in Formula (T-7) have the same meanings and preferred ranges as (X—Y), n and m in Formula (T-2), respectively.

Preferred specific examples of the compound include, but are not limited to, the following compounds.

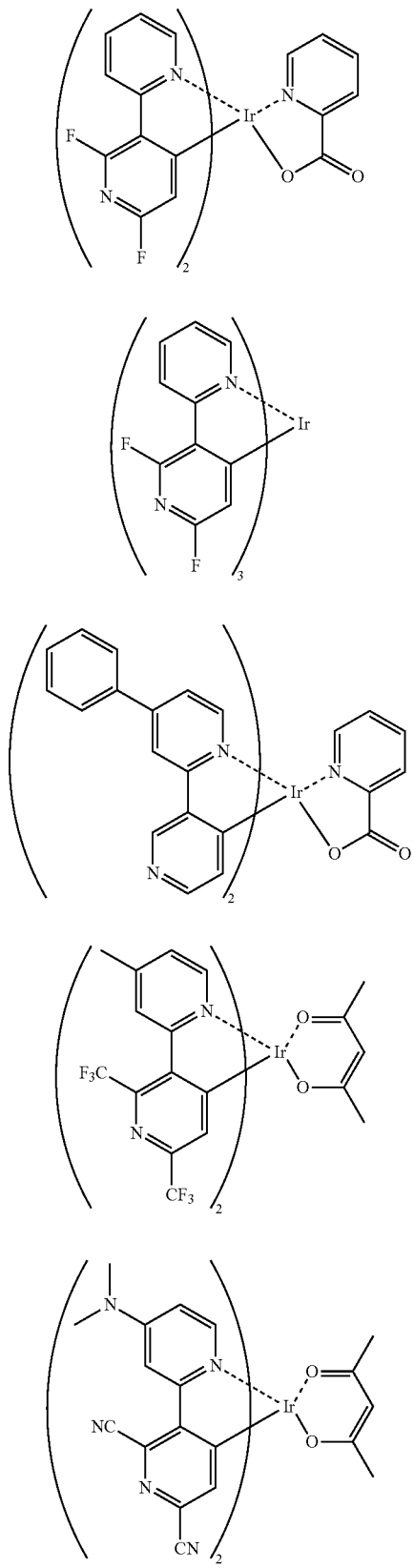

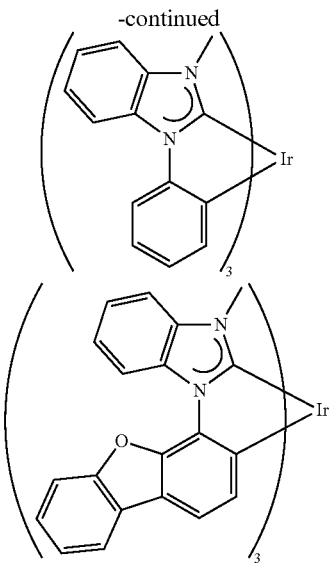

The content of the light emitting material in the light emitting layer is generally from 0.1 to 50% by mass, based on the total mass of all compounds constituting the light emitting layer. From the viewpoint of durability and external quantum efficiency, the light emitting material is preferably contained in an amount of 1 to 50% by mass, more preferably 2 to 40% by mass.

The thickness of the light emitting layer is not particularly limited but is preferably from 2 to 500 nm. From the viewpoint of external quantum efficiency, 3 to 200 nm is more preferably and 5 to 100 nm is even more preferred.

In the device of the present invention, the light emitting layer may be composed of a light emitting material only or may be a mixed layer of a host material and a light emitting material. One or more kinds of light emitting materials may be used. The host material is preferably a charge transporting material. One or more kinds of host materials may be used. For example, the host material may be a mixture of an electron transporting host material and a hole transporting host material. The light emitting layer may include a material that has no ability to transport electrons and does not emit light.

The light emitting layer may have a monolayer structure or a multilayer structure consisting of two or more layers. The individual layers of the multilayer structure may include the same light emitting material or host material or different materials. The light emitting layer may be provided in plurality. In this case, the light emitting layers may emit light of different colors.

<Host Material>

The host material is a compound responsible for the injection and transport of charges in the light emitting layer and does not substantially emit light. The term "not substantially emit light" means that the amount of light emitted from the corresponding compound that does not substantially emit light is preferably 5% or less, more preferably 3% or less, even more preferably 1% or less, based on the total amount of light emitted from the device.

The compound represented by Formula (Cz-1) or (Cz-2) can be used as the host material.

Specific examples of host materials useable in the present invention include the following compounds.

Pyrrole, indole, carbazole, azaindole, azacarbazole, triazole, oxazole, oxadiazole, pyrazole, imidazole, thiophene, polyarylalkanes, pyrazoline, pyrazolone, phenylenediamine, arylamines, amino-substituted chalcones, styrylanthracene, fluorenone, hydrazone, stilbene, silazane, aromatic tertiary amine compounds, styrylamine compounds, porphyrin compounds, polysilane compounds, electrically conductive polymer oligomers, such as poly(N-vinylcarbazole), aniline copolymers, thiophene oligomers and polythiophene, organosilanes, carbon membranes, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidene methane, distyrylpyrazine, fluorinated aromatic compounds, heterocyclic tetracarboxylic anhydrides, such as naphthalene perylene, phthalocyanine, various metal complexes typified by metal complexes of 8-quinolinol derivatives, metal phthalocyanine, and metal complexes having a benzoxazole or benzothiazole ligand, and derivatives thereof (may have a substituent or a condensed ring).

In the present invention, the host material may be combined with a hole transporting host material or an electron transporting host material. A hole transporting host material can be used.

In the present invention, it is preferred that the light emitting layer includes a host material. The host material is preferably a compound represented by Formula (4-1) or (4-2).

In the present invention, the light emitting layer more preferably includes at least one of the compounds that can be represented by Formula (4-1) or (4-2).

In the present invention, when the compound represented by Formula (4-1) or (4-2) is included, the compound represented by Formula (4-1) or (4-2) is contained preferably in an amount of 30 to 100% by mass, more preferably 40 to 100% by mass, particularly preferably 50 to 100% by mass in the light emitting layer. The compound represented by Formula (4-1) or (4-2) may be used in a plurality of constituent layers of the organic layer. In this case, the content of the compound in each of the layer is within the range defined above.

The compound represented by Formula (4-1) or (4-2) may be contained alone in any constituent layer of the organic layer. Alternatively, two or more compounds that can be represented by Formula (4-1) or (4-2) may be contained in combination in any ratio.

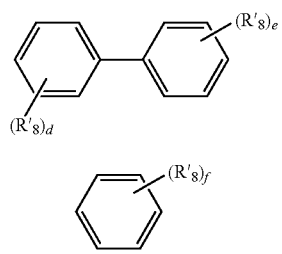

Formula (4-1)

Formula (4-2)

(In Formulae (4-1) and (4-2), d and e represent integers from 0 to 3, with the proviso that at least one of d and e is equal to or greater than 1, f is an integer from 1 to 4, each of $R'_8$ independently represents a substituent, provided that when d, e and f are 2 or greater, each $R'_8$ may be the same as or different from every other $R'_8$, and at least one of the substituents $R'_8$ represents a carbazole group represented by Formula (5)).

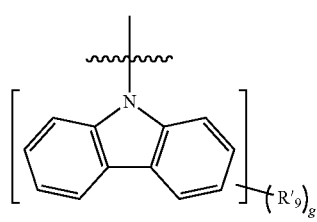

(5)

(In Formula (5), each of $R'_9$ independently represents a substituent and g represents an integer from 0 to 8).

Each of $R'_8$ independently represents a substituent, and specific examples thereof include halogen atoms, alkoxy groups, cyano groups, nitro groups, alkyl groups, aryl groups, heterocyclic groups, and the substituent represented by Formula (5). If $R'_8$ does not represent Formula (5), it is preferably an alkyl group having 10 or less carbon atoms or a substituted or unsubstituted aryl group having 10 or less carbon atoms, more preferably an alkyl group having 6 or less carbon atoms.

Each of $R'_9$ independently represents a substituent, and specific examples thereof include halogen atoms, alkoxy groups, cyano groups, nitro groups, alkyl groups, aryl groups, and heterocyclic groups. Alkyl groups having 10 or less carbon atoms and substituted or unsubstituted aryl group having 10 or less carbon atoms are preferred, and alkyl groups having 6 or less carbon atoms are more preferred.

g represents an integer from 0 to 8. g is preferably from 0 to 4. Within this range, the carbazole structure responsible for charge transport is not excessively blocked. When the carbazole has a substituent, the substituent is symmetric relative to the nitrogen atom, which is preferred in terms of ease of synthesis.

In Formula (4-1), it is preferred that the sum of d and e is 2 or greater from the viewpoint of maintaining the ability to transport charges. Further, it is preferred that the substituents $R'_8$ are in the meta position relative to the other benzene ring. The reason for this is as follows. Since steric hindrance between the adjacent substituents in the ortho position is large, the bonds tend to cleave and the durability deteriorates. Meanwhile, since the molecule having the substituents in the para position is close to a rigid bar in shape and tends to crystallize, the device tends to degrade under high temperature conditions.

Specifically, preferred is a compound represented by the following structure.

$R'_9$ and g in the following structure have the same meanings as $R'_9$ and g in Formula (5).

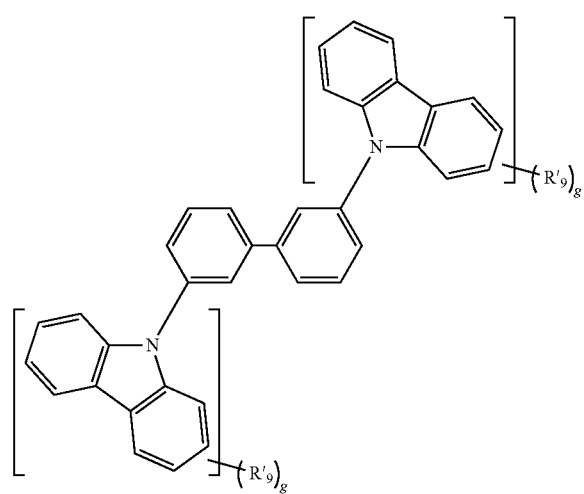

In Formula (4-2), it is preferred that f is 2 or greater from the viewpoint of maintaining the ability to transport charges. When f is 2 or 3, it is preferred that the substituents $R'_8$ are in the meta position relative to each other from the same viewpoint. Specifically, preferred is a compound represented by the following structure. $R'_9$ and g in the following structure have the same meanings as $R'_9$ and g in Formula (5).

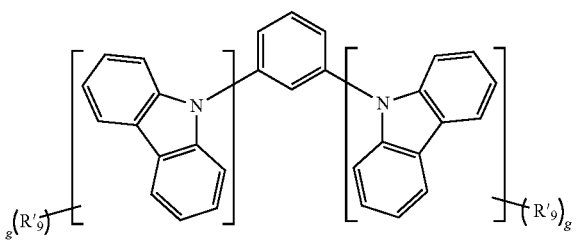

The compounds of Formulae (4-1) and (4-2) may have hydrogen atoms. In this case, the hydrogen atoms are intended to include isotopes thereof (such as deuterium atoms). All of the hydrogen atoms present in the compound may be replaced by hydrogen isotopes. Alternatively, the compound may be present in the form of a mixture of compounds in which the hydrogen atoms are partially replaced by hydrogen isotopes. It is preferred that R'$_9$ in Formula (5) is substituted with a deuterium. Particularly preferred are the following structures.

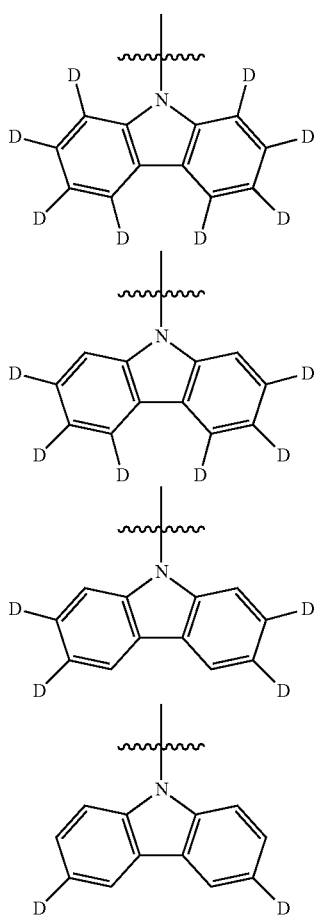

The constituent atoms of the substituents are intended to include isotopes thereof.

The compounds represented by Formulae (4-1) and (4-2) can be synthesized by combinations of various known synthesis methods. As the most common method for the synthesis of carbazole compounds, there can be mentioned the method described in L. F. Tietze and Th. Eicher, "Precision Organic Synthesis", translated by Takano and Ogasawara, p 339 (published by Nankodo) in which a condensate of an aryl hydrazine and a cyclohexane derivative is subjected to an aza-Cope rearrangement reaction, followed by dehydroaromatization. As a coupling reaction between the resulting carbazole compound and an aryl halide compound in the presence of a palladium catalyst, there can be exemplified the methods described in Tetrahedron Letters, vol. 39, p 617 (1998), vol. 39, p 2367 (1998), and vol. 40, p 6393 (1999). The conditions described in the literature can be employed without imposing any particular restriction on the reaction temperature and reaction time. Some commercially available compounds, such as mCP, can be suitably used.

In the present invention, it is preferred to form the compounds represented by Formulae (4-1) and (4-2) into a thin layer by a vapor deposition method. A wet process, such as solution coating, can be suitably employed for thin layer formation. The molecular weight of the compound is preferably limited to 2000 or less, more preferably 1200 or less, particularly preferably 800 or less from the viewpoint of deposition suitability and solubility. Too small a molecular weight of the compound leads to a reduction in vapor pressure and impedes the occurrence of a phase change from gas to solid, making it difficult to form an organic layer. Therefore, the molecular weight of the compound is preferably adjusted to 250 or more, particularly preferably 300 or more, from the viewpoint of deposition suitability.

It is preferred that the compounds represented by Formulae (4-1) and (4-2) have the following structures or are compounds in which one or more of the hydrogen atoms are replaced by deuterium atoms. The substituents R'$_8$ in the following structures have the same meaning as R'$_8$ in Formulae (4-1) and (4-2). The substituents R'$_9$ in the following structures have the same meaning as R'$_9$ in Formula (5).

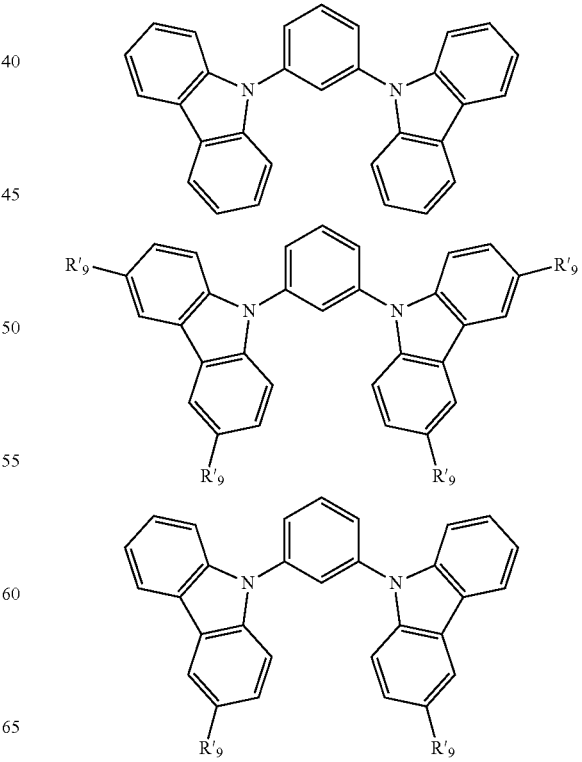

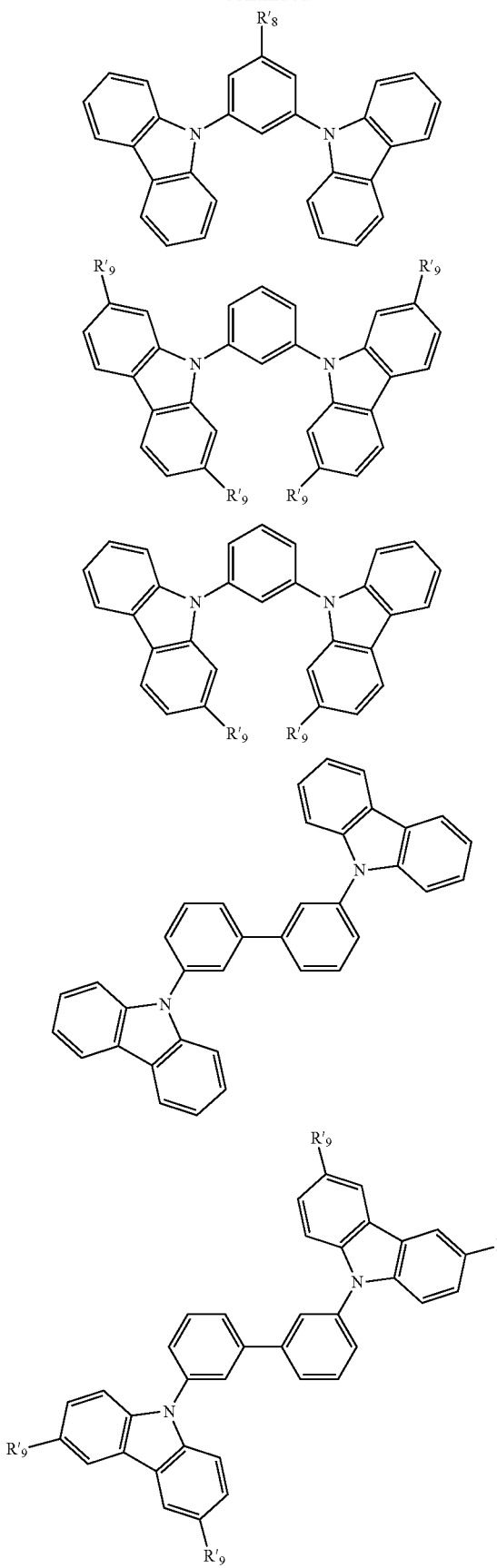

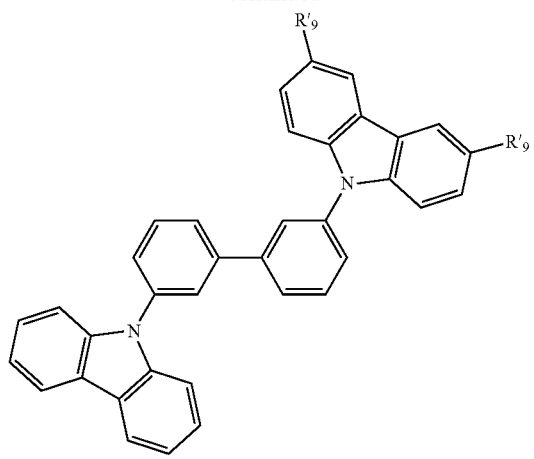
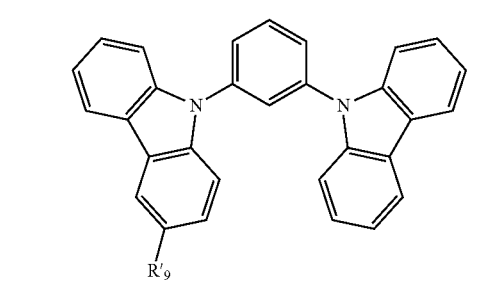
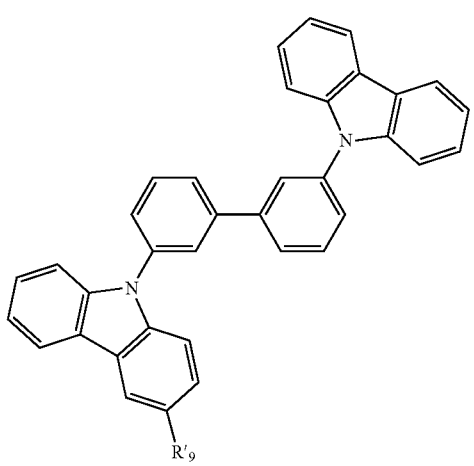
Specific examples of the compounds represented by Formulae (4-1) and (4-2) in the present invention include the following structures, but the present invention is not limited thereto.
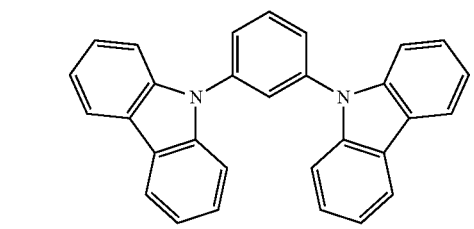
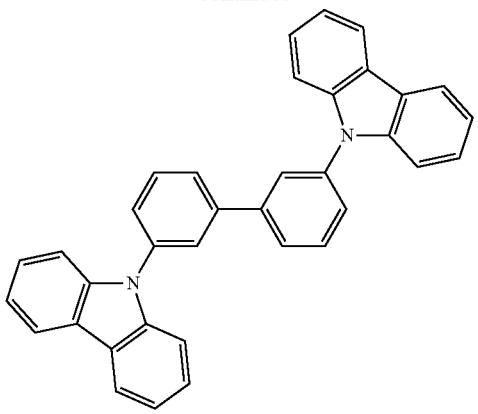
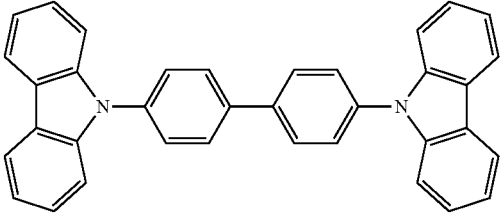
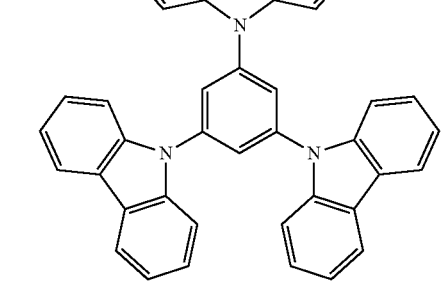
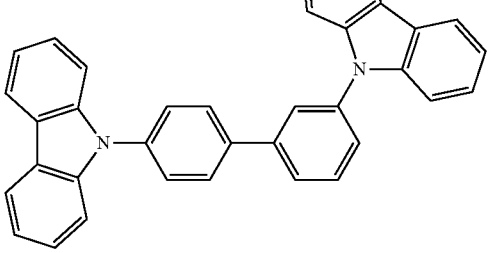

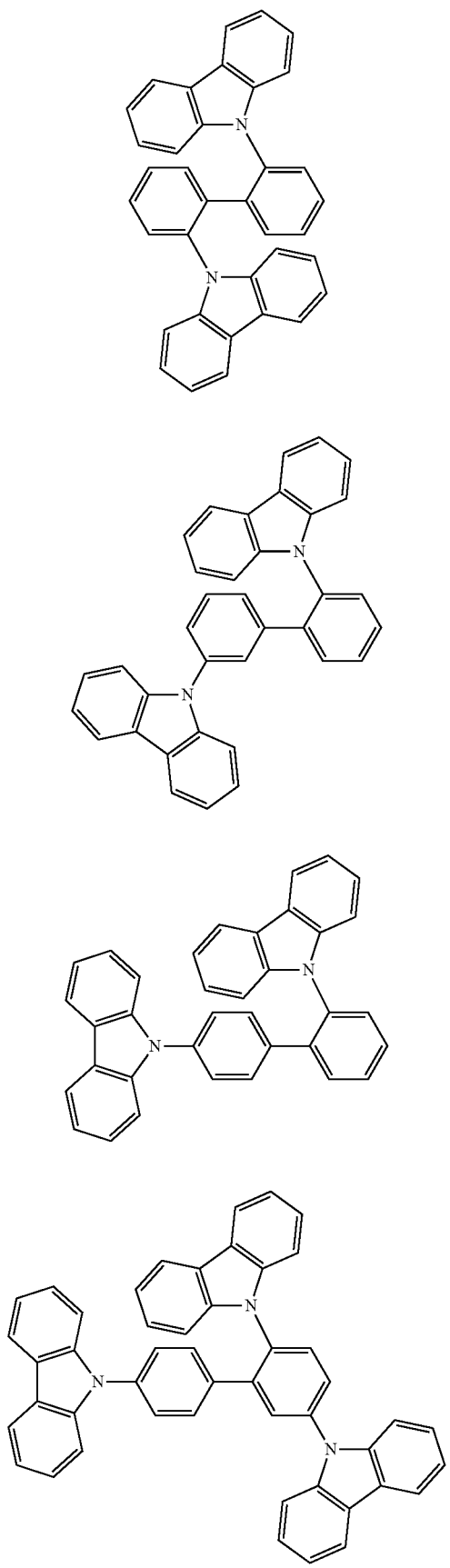
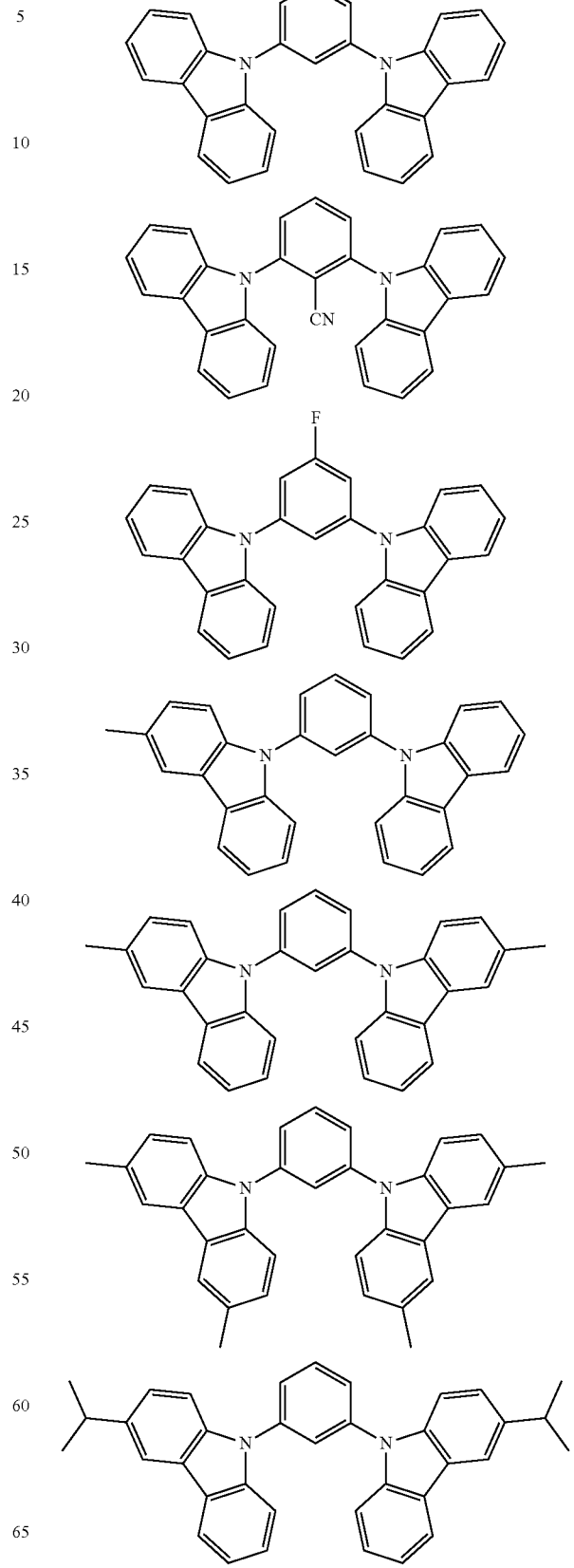

85
-continued
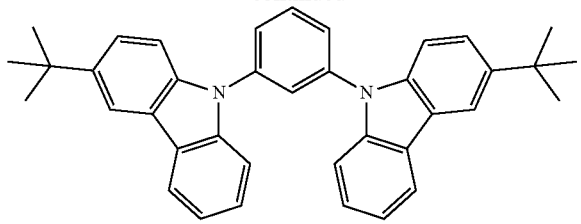
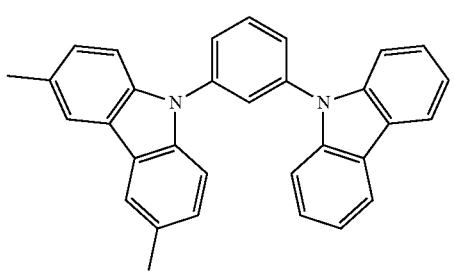
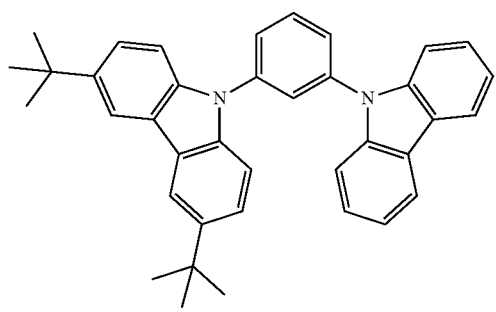
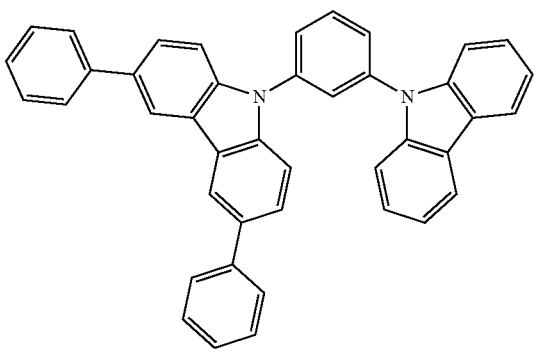
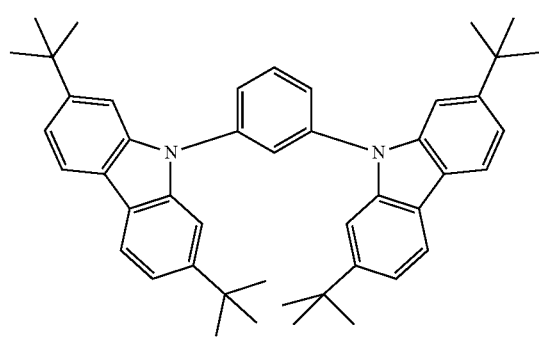
86
-continued
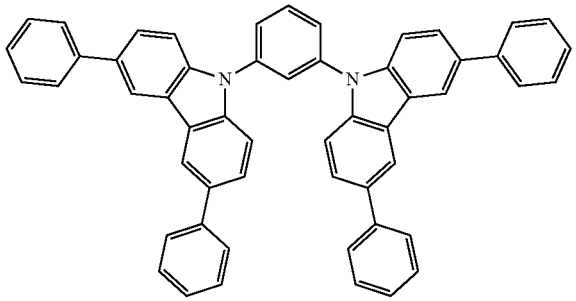
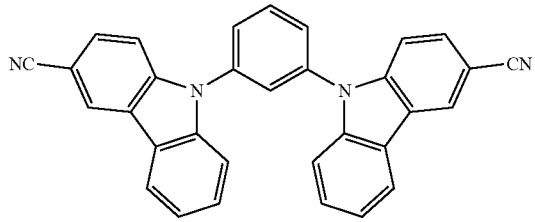
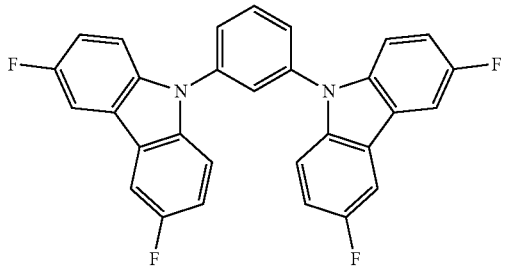
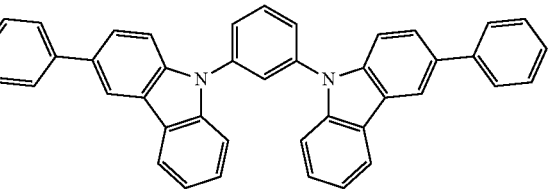
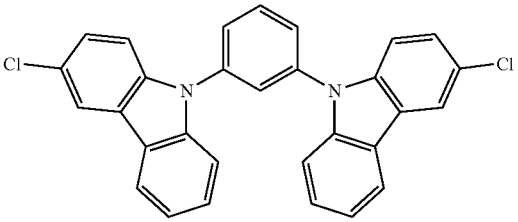
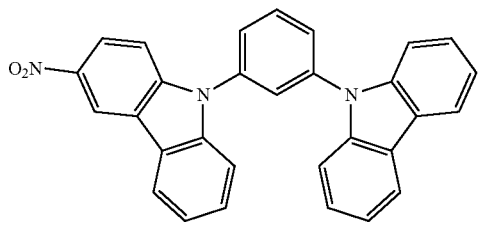
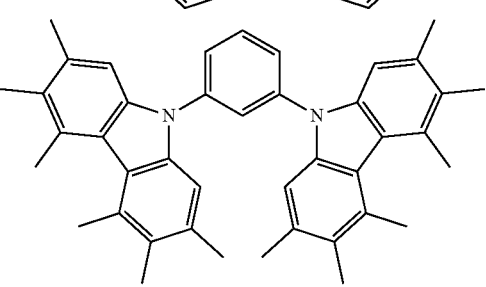

87
-continued
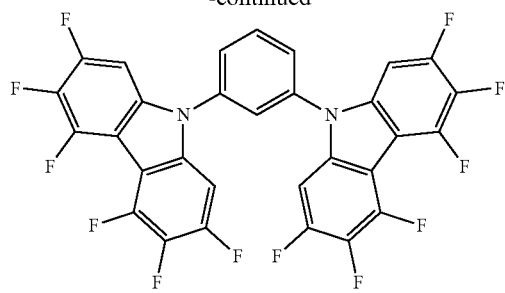
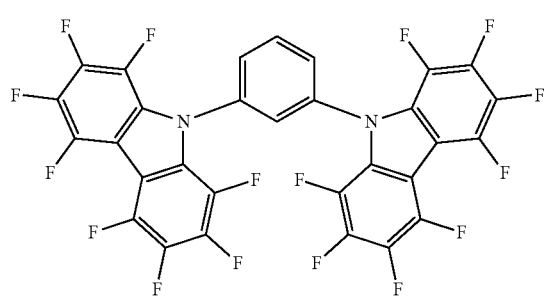
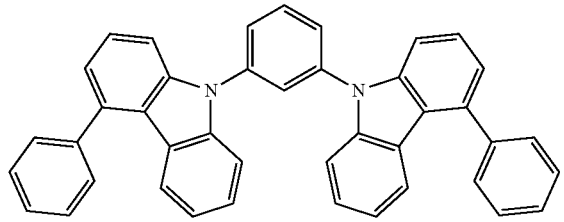
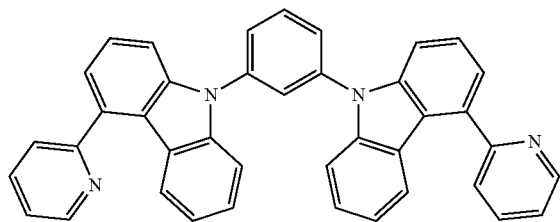
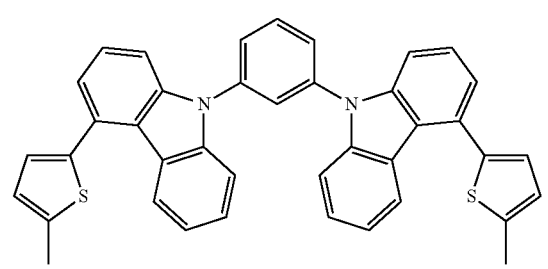
88
-continued
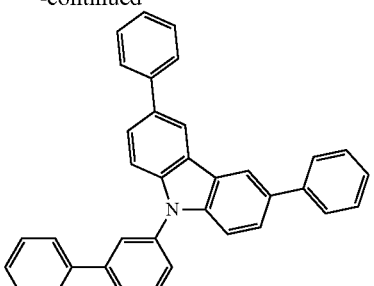
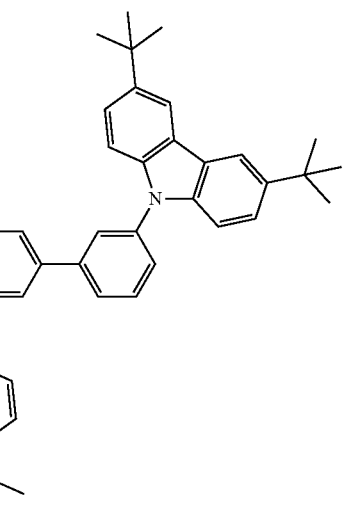
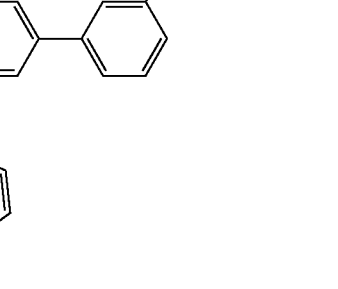

89
-continued
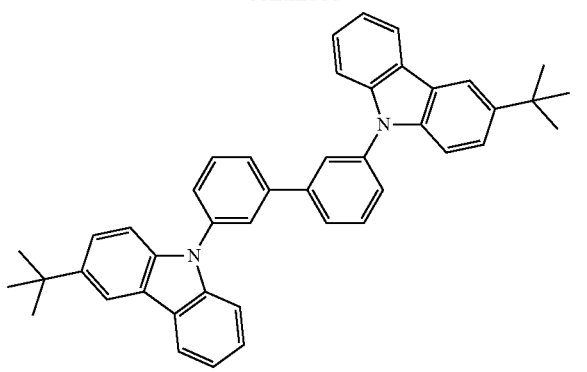
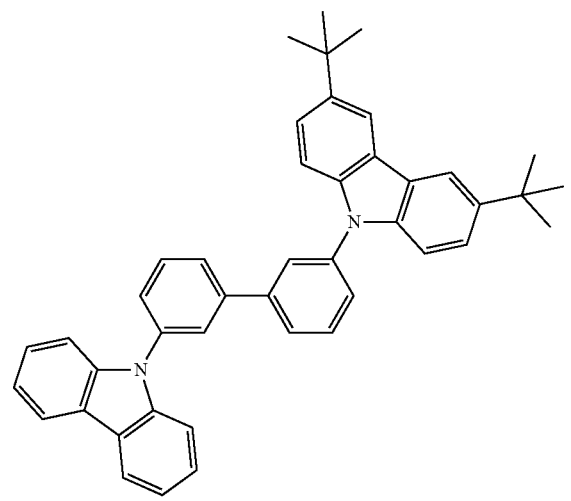
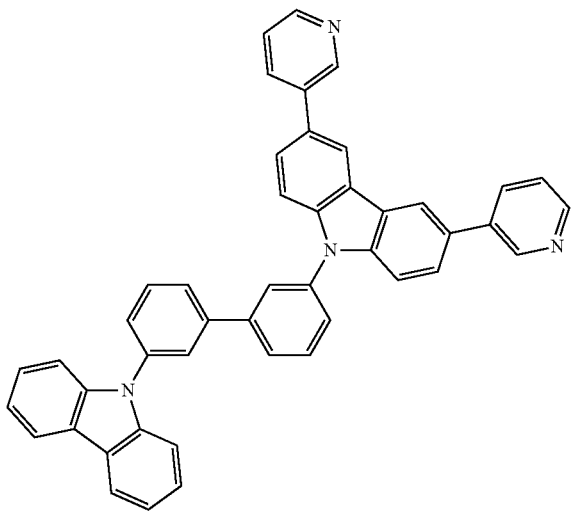
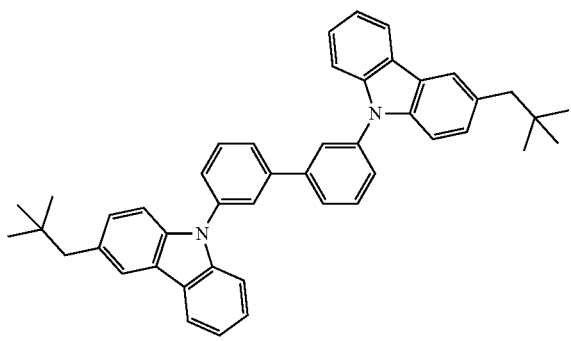
90
-continued
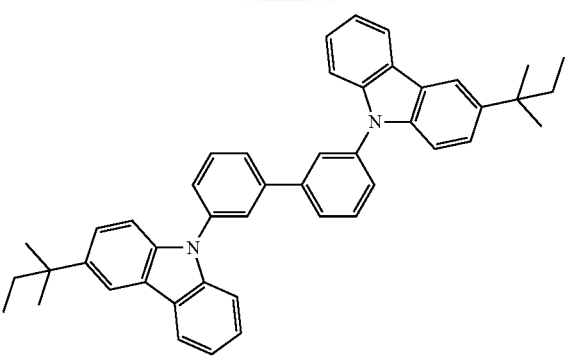
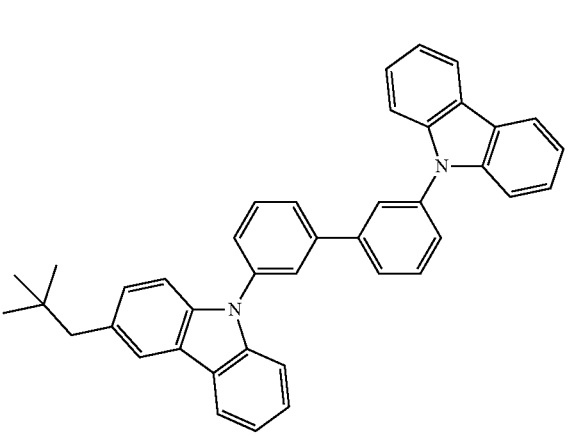
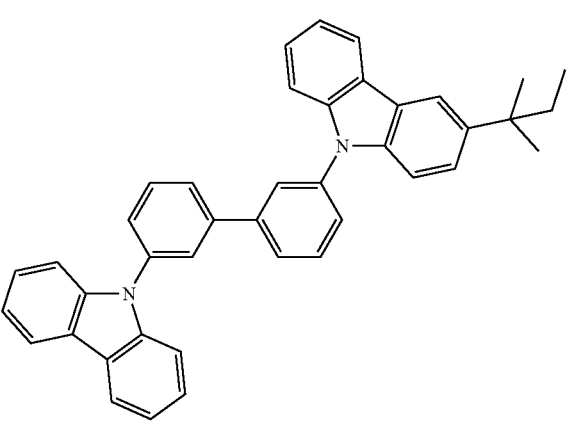

91
-continued
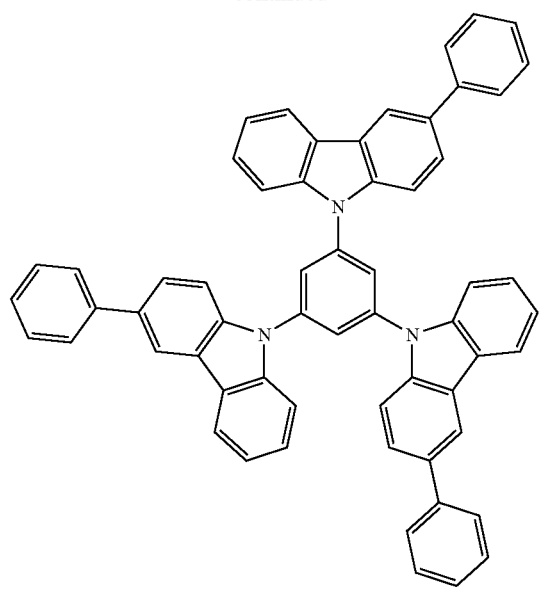
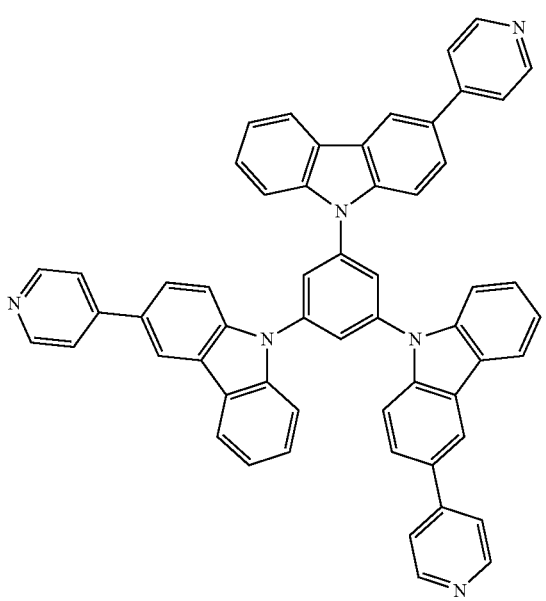
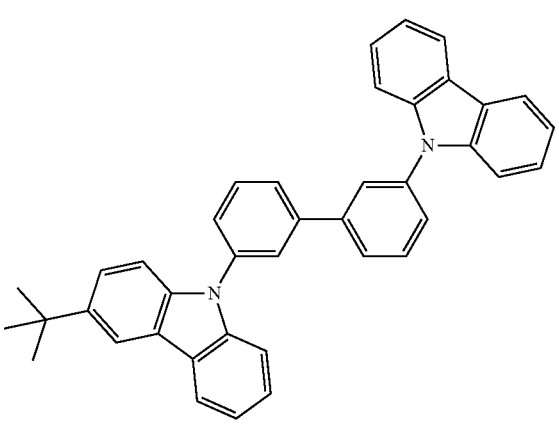
92
-continued
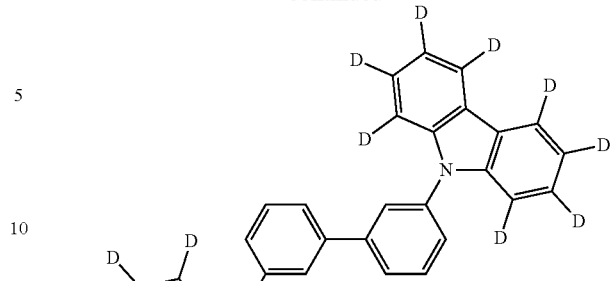
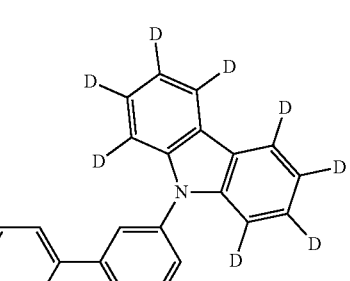
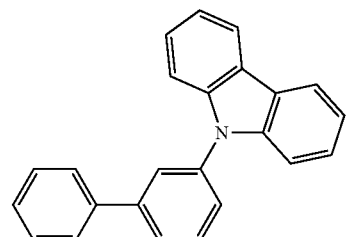

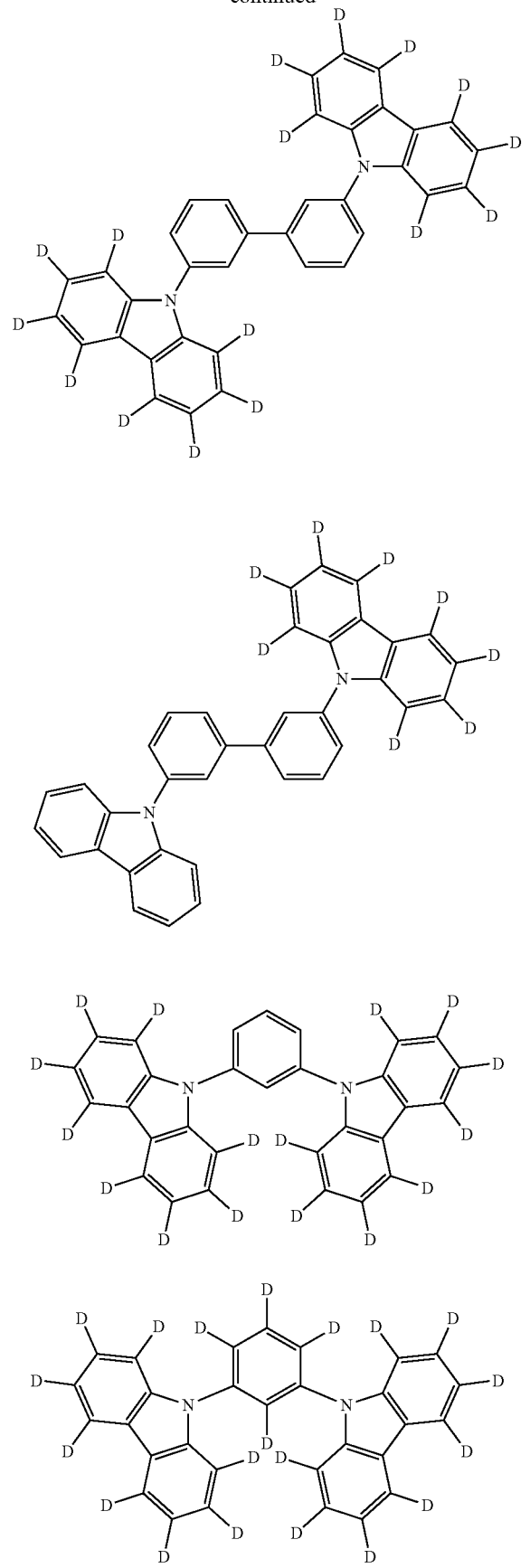

-continued

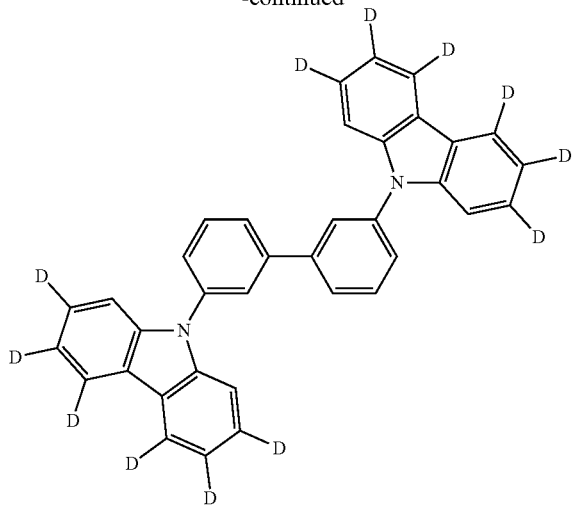

In the present invention, the lowest triplet excitation energy ($T_1$ energy) values of the respective host materials in the light emitting layer are greater than the $T_1$ energy of the phosphorescent material, which is preferred in terms of chromaticity, luminous efficiency and driving durability.

The content of the host material in the present invention is not particularly limited but is preferably from 15% by mass to 95% by mass, based on the total mass of all compounds constituting the light emitting layer from the viewpoint of luminous efficiency and driving voltage.

Preferably, the organic electroluminescence device of the present invention includes an anode as the electrode and has a charge transporting layer between the light emitting layer and the anode wherein the charge transporting layer includes a carbazole compound.

(Charge Transporting Layer)

The charge transporting layer refers to a layer in which charges migrate when a voltage is applied to the organic electroluminescence device. Specifically, charge transporting layer may be a hole injection layer, a hole transporting layer, an electron blocking layer, a light emitting layer, a hole blocking layer, an electron transporting layer or an electron injection layer. Preferably, the charge transporting layer is a hole injection layer, a hole transporting layer, an electron blocking layer or a light emitting layer. The formation of a hole injection layer, a hole transporting layer, an electron blocking layer or a light emitting layer as the charge transporting layer by a coating process enables the fabrication of an organic electroluminescence device with high efficiency at low cost. The charge transporting layer is more preferably a hole injection layer, a hole transporting layer or an electron blocking layer.

—Hole Injection Layer and Hole Transporting Layer—

The hole injection layer and the hole transporting layer are layers that have a function of accepting holes from an anode or an anode side and transporting the holes to a cathode side.

The descriptions of a hole injection layer and a hole transporting layer in Paragraph Nos. [0165] to [0167] of Japanese Patent Application Laid-Open No. 2008-270736 can be applied to the present invention.

It is preferred that the hole injecting layer contains an electron accepting dopant. The presence of the electron accepting dopant improves the ability of the hole injecting layer to inject holes, reduces the driving voltage, brings about efficiency improvement, and the like. The electron accepting dopant may be any organic or inorganic material that can emit electrons from a doped material to generate radical cations, and examples thereof include tetracyanoquinodimethane (TCNQ), tetrafluorotetracyanoquinodimethane ($F_4$-TCNQ), molybdenum oxide and the like.

The content of the electron accepting impurity in the hole injection layer is preferably from 0.01 to 50% by mass, more preferably 0.1 to 40% by mass, even more preferably 0.5 to 30% by mass, based on the total mass of all compounds constituting the hole injection layer.

—Electron Injection Layer and Electron Transporting Layer—

The electron injection layer and the electron transporting layer are layers that have a function of accepting electrons from a cathode or cathode side and transporting the electrons to an anode side. Any low-molecular weight compound or polymer compound may be used as an electron injecting material for the electron injection layer and an electron transporting material for the electron transporting layer.

The electron transporting material may be the compound represented by Formula (Cz-1) or (Cz-2) of the present invention. The other layers is preferably a layer containing a pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidene methane derivatives, distyrylpyrazine derivatives, aromatic tetracarboxylic anhydrides, such as naphthalene and perylene, phthalocyanine derivatives, various metal complexes typified by metal complexes of 8-quinolinol derivatives, metal phthalocyanine, and complexes having a benzoxazole or benzothiazole ligand, or organosilane derivatives typified by silole.

From the viewpoint of low driving voltage, it is preferred to limit the thicknesses of the electron injection layer and the electron transporting layer to 500 nm or less.

The thickness of the electron transporting layer is preferably from 1 nm to 500 nm, more preferably from 5 nm to 200 nm, even more preferably from 10 nm to 100 nm. The thickness of the electron injection layer is preferably from 0.1 nm to 200 nm, more preferably from 0.2 nm to 100 nm, even more preferably from 0.5 nm to 50 nm.

Each of the electron injection layer and the electron transporting layer may have a monolayer structure composed of one or more of the above-described materials or a multilayer structure consisting of two or more layers having the same composition or different compositions.

It is preferred that the electron injection layer contains an electron donating dopant. The presence of the electron donating dopant improves the ability of the electron injection layer to inject electrons, reduces the driving voltage, brings about efficiency improvement, and the like. The electron donating dopant may be any organic or inorganic material that can donate electrons to a doped material to generate radical anions, and examples thereof include tetrathiafulvalene (TTF), tetrathianaphthacene (TTT), lithium, cesium and the like.

The content of the electron donating dopant in the electron injection layer is preferably from 0.01 to 50% by mass, more preferably from 0.1 to 40% by mass, even more preferably from 0.5 to 30% by mass, based on the total mass of all compounds constituting the electron injection layer.

—Hole Blocking Layer—

The hole blocking layer is a layer that has a function of preventing holes transported from an anode side to the light emitting layer from escaping toward a cathode side. In the present invention, the hole blocking layer can be disposed as an organic layer adjacent to the light emitting layer at a cathode side.

Examples of organic compounds constituting the hole blocking layer include aluminum complexes, such as aluminum (III) bis(2-methyl-8-quinolinato)-4-phenylphenolate (hereinafter abbreviated as BAlq), triazole derivatives, and phenanthroline derivatives, such as 2,9-dimethyl-4,7-diphenyl-1,10-phenanthroline (hereinafter abbreviated as BCP).

The thickness of the hole blocking layer is preferably from 1 nm to 500 nm, more preferably from 5 nm to 200 nm, even more preferably from 10 nm to 100 nm.

The hole blocking layer may have a monolayer structure composed of one or more of the above-described materials. Alternatively, the hole blocking layer may have a multilayer structure consisting of two or more layers having the same composition or different compositions.

—Electron Blocking Layer—

The electron blocking layer is a layer that has a function of preventing electrons transported from a cathode side to the light emitting layer from escaping toward an anode side. In the present invention, the electron blocking layer can be disposed as an organic layer adjacent to the light emitting layer at an anode side.

Examples of organic compounds constituting the electron blocking layer include those exemplified as the hole transport material.

The thickness of the electron blocking layer is preferably from 1 nm to 500 nm, more preferably from 5 nm to 200 nm, even more preferably from 10 nm to 100 nm.

The electron blocking layer may have a monolayer structure composed of one or more of the above-described materials. Alternatively, the electron blocking layer may have a multilayer structure consisting of two or more layers having the same composition or different compositions.

<Protective Layer>

In the present invention, a protective layer may be provided to protect the whole structure of the organic EL device.

The description of a protective layer in Paragraph Nos. [0169] to [0170] of Japanese Patent Application Laid-Open No. 2008-270736 can be applied to the present invention.

<Sealing Container>

A sealing container may be used to completely encapsulate the device of the present invention.

The description of a sealing container in Paragraph No. [0171] of Japanese Patent Application Laid-Open No. 2008-270736 can be applied to the present invention.

(Driving)

When a direct current (it may contain an alternating current component, if needed) voltage (usually from 2 to 15 volts) or direct current is applied between the anode and the cathode, the organic electroluminescence device of the present invention can emit light.

The driving methods described in Japanese Patent Application Laid-Open No. Hei 2-148687, Japanese Patent Application Laid-Open No. Hei 6-301355, Japanese Patent Application Laid-Open No. Hei 5-29080, Japanese Patent Application Laid-Open No. Hei 7-134558, Japanese Patent Application Laid-Open No. Hei 8-234685, Japanese Patent Application Laid-Open No. Hei 8-241047, Japanese Patent No. 2784615, U.S. Pat. No. 5,828,429, U.S. Pat. No. 6,023,308, and the like can be applied to drive the organic electroluminescence device of the present invention.

The external quantum efficiency of the organic electroluminescence device of the present invention is preferably 7% or higher, more preferably 10% or higher, even more preferably 12% or higher. The external quantum efficiency can be defined as the maximum value of the external quantum efficiency obtained when the device is driven at 20° C. or the value of the external quantum efficiency at around 300-400 $cd/m^2$ when the device is driven at 20° C.

The internal quantum efficiency of the organic electroluminescence device of the present invention is preferably 30% or higher, more preferably 50% or higher, even more preferably 70% or higher. The internal quantum efficiency of the device is calculated by dividing the external quantum efficiency by light output efficiency. The light output efficiency values of common organic EL devices are about 20%, which can be controlled to 20% or higher by conducting research on the shape of substrates, the shape of electrodes, the thickness of organic layers, the thickness of inorganic layers, the refractive index of organic layers, the refractive index of inorganic layers and the like.

(Applications of the Device of the Present Invention)

The device of the present invention is suitable for use in various applications, for example, display devices, displays, backlights, electron photographs, light sources for illumination, recording, exposure and reading, signs, signboards, interiors, optical communications and the like. Particularly, the device of the present invention is preferably used in devices that are driven in regions where luminance intensity is high, such as light emission apparatuses and display apparatuses.

An explanation will be given about a light emitting apparatus of the present invention with reference to FIG. 2.

Figure 2:
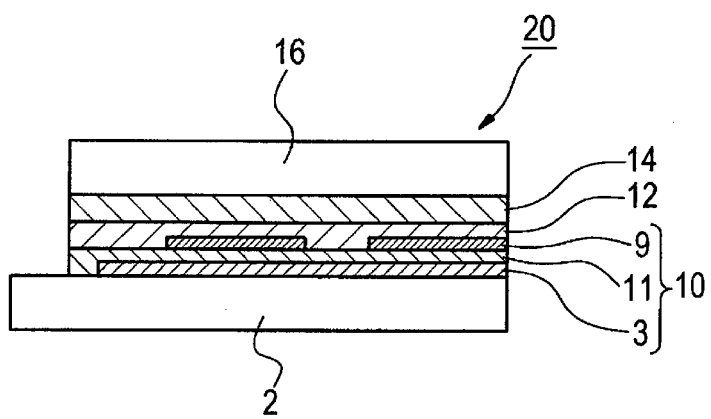
FIG. 2 is a schematic view illustrating an example of a light emission apparatus according to the present invention.

FIG. 2 is a cross-sectional view schematically illustrating an example of a light emitting apparatus of the present invention. The light emitting apparatus 20 of FIG. 2 includes a transparent substrate (a support substrate) 2, an organic electroluminescence device 10, a sealing container 16, and the like.

The organic electroluminescence device 10 is fabricated by laminating an anode (a first electrode) 3, an organic layer 11 and a cathode (a second electrode) 9 in this order on the substrate 2. A protective layer 12 is laminated on the cathode 9. The sealing container 16 is formed on the protective layer 12 through an adhesive layer 14. Parts of each of the electrodes 3 and 9, a barrier, an insulating layer, and the like. are omitted.

A photosetting or thermosetting adhesive may be used to form the adhesive layer 14. For example, a thermosetting adhesive sheet may also be used.

The light emitting apparatus of the present invention can be used for illumination apparatuses and display apparatuses, such as TVs, personal computers, mobile phones and electronic papers, but is not particularly limited to these uses.

(Illumination apparatus)

An explanation will be given about an illumination apparatus of the present invention with reference to FIG. 3.

Figure 3:
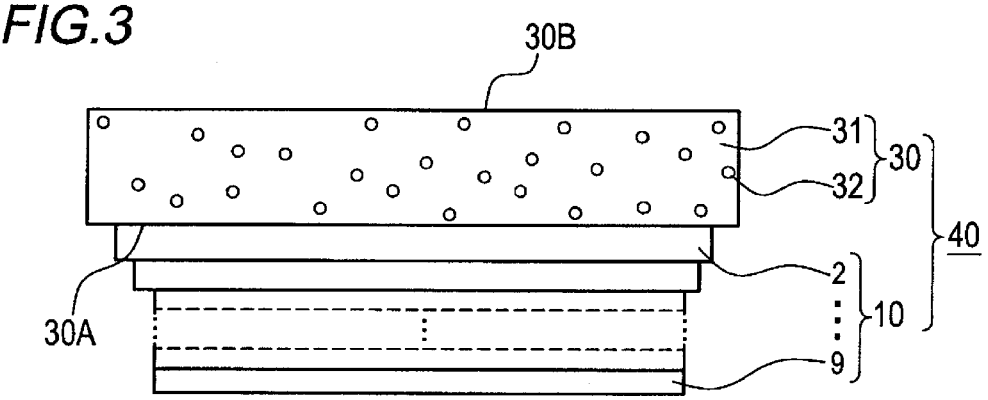
FIG. 3 is a schematic view illustrating an example of an illumination apparatus according to the present invention.

FIG. 3 is a cross-sectional view schematically illustrating an example of an illumination apparatus of the present invention. As illustrated in FIG. 3, the illumination apparatus 40 is equipped with the above-described organic electroluminescence device 10 and a light scattering member 30. More specifically, the illumination apparatus 40 is constructed such that the substrate 2 of the organic electroluminescence device 10 is brought into contact with the light scattering member 30.

The light scattering member 30 is not particularly limited so long as it can scatter light. In FIG. 3, the light scattering member 30 includes a transparent substrate 31 and fine particulates 32 dispersed therein. For example, a glass substrate can be suitably used as the transparent substrate 31 and fine particulates of a transparent resin can be suitably used as the fine particulates 32. Known glass substrates and transparent resin fine particulates can be used. When light from the organic electroluminescence device 10 is incident on a light incident plane 30A of the light scattering member 30 of the illumination apparatus 40, the light scattering member 30 scatters the incident light, which is then emitted as illumination light from a light exit plane 30B.

EXAMPLES

The present invention will be explained in more detail with reference to the following examples. However, these examples are not intended to limit the present invention.

Example 1

Synthesis Examples

Example 1-1

Synthesis of the Exemplified Compound (1)

The exemplified compound (1) was synthesized and purified by the method described in Synthesis Example 2 of International Publication No. 2004/074399. As a result, the exemplified compound (1) was obtained in the form of a crude crystal (hereinafter referred to as "Crude 1"). The crude crystal was purified by sublimation as described in the above patent publication to obtain a purified crystal of the exemplified compound (1) (hereinafter referred to as "Sublimated 1").

Purification of Crude 1 by silica gel column chromatography (eluting solvent: toluene/hexane=(1/1, v/v)) afforded a crude crystal (hereinafter referred to as "Crude 2"). Recrystallization of Crude 2 from toluene/hexane (1/1, v/v)) afforded a crude crystal (hereinafter referred to as "Crude 3"). Additional recrystallization of Crude 3 from toluene/hexane (1/1, v/v)) afforded a crude crystal (hereinafter referred to as "Crude 4"). A crystal purified from Crude 2 by sublimation is referred to as "Sublimated 2" a crystal purified from Crude 3 by sublimation is referred to as "Sublimated 3" and a crystal purified from Crude 4 by sublimation is referred to as "Sublimated 4". Sublimated 4 was further purified by sublimation to obtain a crystal (hereinafter referred to as "Sublimated 5"). For comparison, a slight amount of a powder of 3,5-(diphenyl)phenylboric acid as an intermediate for synthesis was added to a sample obtained from Sublimated 5 and ground in a mortar to obtain a powder having a uniform composition (hereinafter referred to as "Comparative 1"). In the same manner as above, a slight amount of a powder of 1,3,5-tribromobenzene as a starting material was added to a sample obtained from Sublimated 5 and ground in a mortar to obtain a powder having a uniform composition (hereinafter referred to as "Comparative 2").

Example 1-2

Synthesis of the Exemplified Compound (2)

The exemplified compound (2) was synthesized in the same manner as in Example 1-1, except that 3,5-bis(3'-biphenyl)phenylboric acid was used instead of the intermediate (D) described in Synthesis Example 2 of International Publication No. 2004/074399. The purification procedure of the exemplified compound (1) in Example 1-1 was repeated to obtain the same named crystals ("Crude 1", "Sublimated 1" and the like).

Example 1-3

Synthesis of the Exemplified Compound (9)

The exemplified compound (9) was synthesized in the same manner as in Example 1-1, except that 3-t-butylcarbazole was used instead of carbazole described in Synthesis Example 2 of International Publication No. 2004/074399. The purification procedure of the exemplified compound (1) in Example 1-1 was repeated to obtain the same named crystals ("Crude 1", "Sublimated 1" and the like).

Example 1-4

Synthesis of the Exemplified Compound (11)

The exemplified compound (11) was synthesized in the same manner as in Example 1-1, except that 3,6-diphenylcarbazole was used instead of carbazole described in Synthesis Example 2 of International Publication No. 2004/074399. The purification procedure of the exemplified compound (1) in Example 1-1 was repeated to obtain the same named crystals ("Crude 1", "Sublimated 1" and the like).

Example 1-5

Synthesis of the Exemplified Compound (13)

The exemplified compound (13) was synthesized in the same manner as in Example 1-1, except that 3-triphenylsilylcarbazole was used instead of carbazole described in Synthesis Example 2 of International Publication No. 2004/074399. The purification procedure of the exemplified compound (1) in Example 1-1 was repeated to obtain the same named crystals ("Crude 1", "Sublimated 1" and the like).

Example 1-6

Synthesis of the Exemplified Compound (20)

The exemplified compound (20) was synthesized and purified by the method described in Synthesis Example 5 of International Publication No. 2004/074399. As a result, the exemplified compound (20) was obtained in the form of a white powder (hereinafter referred to as "Crude 1"). Purification of Crude 1 by silica gel column chromatography (eluting solvent: toluene/hexane=(1/1, v/v)) afforded a crude crystal (hereinafter referred to as "Crude 2"). Recrystallization of Crude 2 from toluene/hexane (1/1, v/v)) afforded obtain a crude crystal (hereinafter referred to as "Crude 3"). A crystal purified from Crude 1 by sublimation is referred to as "Sublimated 1," a crystal purified from Crude 2 by sublimation is referred to as "Sublimated 2," and a crystal purified from Crude 3 by sublimation is referred to as "Sublimated 3." Sublimated 3 was further purified by sublimation to obtain a purified crystal (hereinafter referred to as "Sublimated 4").

Example 1-7

Synthesis of the Exemplified Compound (25)

The exemplified compound (25) was synthesized and purified by the method described in Synthesis Example 9 of International Publication No. 2004/074399. As a result, the exemplified compound (25) was obtained in the form of a white powder (hereinafter referred to as "Crude 1"). The purification procedure of the exemplified compound (20) was repeated while using the same Lot numbers to obtain to manufacture samples with different purities according to the different purification methods.

The purities and impurity contents of the products obtained in Examples 1-1 to 1-7 were analyzed by high-performance liquid chromatography (TSKgel ODS-100Z, Tosoh). The proportions of the absorption intensity areas at 254 nm were defined as the purities (%) and impurity contents (%). The high-performance liquid chromatography (HPLC) was conducted under the following analysis conditions.

(Analysis Conditions for HPLC)

HPLC system: HPLC manufactured by Shimadzu Corporation (LC-10 ADVP pump, CTO-10 ACVP column oven, SIL-10 ADVP autosampler, RID-10 A differential refractive index detector, CLASS-VP analysis software)

Column: TSKgel ODS-100Z, Tosoh

Mobile layer, flow rate: 60% aqueous tetrahydrofuran (THF) solution, 1.0 ml/min

Column temperature: 40° C.

Sample concentration: 0.05 mass %

The concentrations of the samples provided for the HPLC analysis were 0.05 mass %, which is higher than a common sample concentration for HPLC, thus enabling effective detection of impurities at a level of 0.001%.

Example 2

Example 2-1

Fabrication of Devices

A glass substrate having an ITO film with 0.5 mm thickness and 2.5 cm square (Geomatec, surface resistivity=10 Ω/sq.) was cleaned in 2-propanol in a cleaning container by sonication, followed by UV ozone treatment for 30 min. The following organic compound layers were sequentially formed on the ITO film as a transparent anode by vacuum deposition.

First layer: CuPC: film thickness 10 nm
Second layer: NPD: film thickness 30 nm
Third layer: Sublimated 5 of the compound (1) and GD-1 (mass ratio=95:5): film thickness 40 nm
Fourth layer: BAlq: film thickness 10 nm
Fifth layer: Alq: film thickness 20 nm Lithium fluoride and aluminum were sequentially deposited to thicknesses of 0.1 nm and 100 nm, respectively, on the fifth layer to form a cathode.

The resulting structure was placed in a glove box purged with nitrogen gas without being exposed to the atmosphere and encapsulated with a glass encapsulation can and a UV curable adhesive (XNR5516HV, Nagase Ciba Co., Ltd.) to fabricate an organic electroluminescence device 1-1.

Devices 1-2 to 1-6 and Comparative Devices 1-1 to 1-5 were fabricated in the same manner as described above, except the materials shown in Table 1 were used instead of the compound (1) as a host material of the third layer.

(Evaluation of Performance of the Organic Electroluminescence Devices)

The devices were tested for efficiency and durability by the following methods. The results are shown in Table 1.

(a) Efficiency

Using Source Measure Unit 2400 (Toyo Technica), a direct current voltage was applied to each of the devices to allow the device to emit light. The luminance intensity of light emitted from the device was measured using a luminance meter (BM-8, Topcon Corporation). The emission spectrum and emission wavelengths were measured using a spectral analyzer (PMA-11, Hamamatsu Photonics). Based on these values, the external quantum efficiency of the device at a luminance intensity of around 1000 cd/m$^2$ was calculated by a luminance intensity conversion method. The external quantum efficiency of the device was expressed as a relative value to that of the device using "Sublimated 5" set as 10. The greater the value, the better the efficiency, which is preferable.

(b) Durability

A direct current was applied to each of the devices until the luminance intensity reached 1000 cd/m$^2$ to allow the device to continuously emit light. The time needed to reach a luminance intensity of 500 cd/m$^2$ was defined as indicative of durability. The durability of the device was expressed as a relative value to that of the device using "Sublimated 5" set as 10. The symbol "<" in the durability evaluation is a sign of inequality and, for example, "<1" implies that the relative value of durability is less than 1.

The crystals of the compound (1) used, the purities (%) of the compound (1), the amounts (%) of the impurities, and the efficiency and durability values of the devices are shown in Table 1. No impurities other than the impurities (1-1), (1-2) and (1-3) shown in Table 1 were detected by HPLC. The structures of the impurities (1-1), (1-2) and (1-3) are as follows.

TABLE 1

| Device No. | Compound (1) | Purity (%) | Impurity (1-1) (%) | Impurity (1-2) (%) | Impurity (1-3) (%) | Efficiency (relative value) | Durability (relative value) | Remarks |
|---|---|---|---|---|---|---|---|---|
| Device 1-1 | Sublimated 5 | 100.000 | 0.000 | 0.000 | 0.000 | 10 | 10 | Inventive |
| Device 1-2 | Sublimated 4 | 99.977 | 0.023 | 0.000 | 0.000 | 10 | 10 | Inventive |
| Device 1-3 | Sublimated 3 | 99.94 | 0.06 | 0.00 | 0.00 | 10 | 10 | Inventive |
| Comparative device 1-1 | Sublimated 2 | 99.75 | 0.25 | 0.00 | 0.00 | 10 | 5 | Comparative |
| Comparative device 1-2 | Sublimated 1 | 99.35 | 0.65 | 0.00 | 0.00 | 9 | 3 | Comparative (Synthesis purification method described in WO2004/074399) |
| Device 1-4 | Crude 4 | 99.92 | 0.08 | 0.00 | 0.00 | 10 | 10 | Inventive |
| Comparative device 1-3 | Crude 3 | 99.85 | 0.15 | 0.00 | 0.00 | 10 | 7 | Comparative |
| Comparative device 1-4 | Crude 2 | 98.80 | 1.20 | 0.00 | 0.00 | 9 | <1 | Comparative |
| Comparative device 1-5 | Crude 1 | 97.92 | 1.75 | 0.33 | 0.00 | 7 | <1 | Comparative |

TABLE 1-continued

| Device No. | Compound (1) | Purity (%) | Impurity (1-1) (%) | Impurity (1-2) (%) | Impurity (1-3) (%) | Efficiency (relative value) | Durability (relative value) | Remarks |
|---|---|---|---|---|---|---|---|---|
| Device 1-5 | Comparative 1 | 99.329 | 0.000 | 0.671 | 0.000 | 10 | 10 | Inventive |
| Device 1-6 | Comparative 2 | 99.451 | 0.000 | 0.000 | 0.549 | 10 | 10 | Inventive |

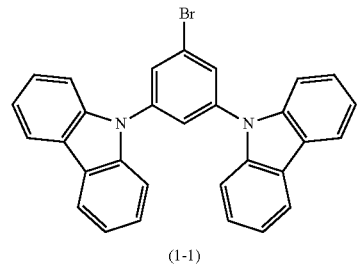 [SMILES: Brc1cc(-n2c3ccccc3c3ccccc32)cc(-n2c3ccccc3c3ccccc32)c1]

(1-1)

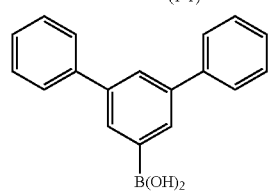

(1-2)

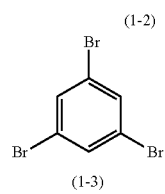

(1-3)

As can be known from the results in Table 1, the efficiency and durability values of the devices, particularly the durability values, are not necessarily consistent with the purity order of the compound (1), and instead they have a close correlation with the particular impurity represented by Formula (I-1). In addition, the efficiency and durability of the device 1-6 were not affected by the presence of 1,3,5-tribromobenzene, which is the same kind of bromo compound as the impurity represented by Formula (I-1). From this observation, it can be known that all bromo compounds do not adversely affect the device performance and the impurity represented by Formula (I-1) specifically adversely affects on the device performance.

Example 2-2

Devices were fabricated in the same manner as the procedure of Example 2-1 for the fabrication of the device 1-1, except that GD-2 was used as a light emitting material instead of GD-1. The results of evaluations of the devices are shown in Table 2.

TABLE 2

| Device No. | Compound (1) | Efficiency (relative value) | Durability (relative value) | Remarks |
|---|---|---|---|---|
| Device 2-1 | Sublimated 5 | 10 | 10 | Inventive |
| Comparative device 2-1 | Sublimated 2 | 10 | 4 | Comparative |
| Comparative device 2-2 | Sublimated 1 | 9 | 2 | Comparative (Synthesis purification method described in WO2004/074399) |
| Device 2-2 | Comparative 1 | 10 | 10 | Inventive |
| Device 2-3 | Comparative 2 | 10 | 10 | Inventive |

Example 2-3

Devices were fabricated in the same manner as the procedure of Example 2-1 for the fabrication of the device 1-1, except that BD-1 was used as a light emitting material instead of GD-1. The results of evaluations of the devices are shown in Table 3.

TABLE 3

| Device No. | Compound (1) | Efficiency (relative value) | Durability (relative value) | Remarks |
|---|---|---|---|---|
| Device 3-1 | Sublimated 5 | 10 | 10 | Inventive |
| Comparative device 3-1 | Sublimated 2 | 9 | 3 | Comparative |

TABLE 3-continued

| Device No. | Compound (1) | Efficiency (relative value) | Durability (relative value) | Remarks |
|---|---|---|---|---|
| Comparative device 3-2 | Sublimated 1 | 8 | <1 | Comparative (Synthesis purification method described in WO2004/074399) |
| Device 3-2 | Comparative 1 | 10 | 10 | Inventive |
| Device 3-3 | Comparative 2 | 10 | 10 | Inventive |

Example 2-4

Devices were fabricated in the same manner as the procedure of Example 2-1 for the fabrication of the device 1-1, except that RD-1 was used as a light emitting material instead of GD-1. The results of evaluations of the devices are shown in Table 4.

TABLE 4

| Device No. | Compound (1) | Efficiency (relative value) | Durability (relative value) | Remarks |
|---|---|---|---|---|
| Device 4-1 | Sublimated 5 | 10 | 10 | Inventive |
| Comparative device 4-1 | Sublimated 2 | 10 | 6 | Comparative |

TABLE 4-continued

| Device No. | Compound (1) | Efficiency (relative value) | Durability (relative value) | Remarks |
|---|---|---|---|---|
| Comparative device 4-2 | Sublimated 1 | 10 | 3 | Comparative (Synthesis purification method described in WO2004/074399) |
| Device 4-2 | Comparative 1 | 10 | 10 | Inventive |
| Device 4-3 | Comparative 2 | 10 | 10 | Inventive |

From these results, it can be seen that only the particular impurity represented by Formula (I-1) adversely affects the durability of the devices despite different structures of the light emitting materials combined and different colors of light emitted from the light emitting materials.

Example 3

Devices were fabricated in the same manner as the procedure of Example 2-1 for the fabrication of the device 1-1, except that the compound (2) was used as a host material instead of the compound (1). The results of evaluations of the devices, together with the purities (%) of the compound (2) and the contents of the impurities (%) as a result of the respective purification methods, are shown in Table 5. No impurities other than the impurities (2-1), (2-2) and (2-3) shown in Table 5 were detected by HPLC. The structures of the impurities (2-1), (2-2) and (2-3) are shown below. The efficiency and durability results of the devices were expressed as relative values to those of the device using "Sublimated 5" each set as 10.

TABLE 5

| Device No. | Compound (2) | Purity (%) | Impurity (2-1) (%) | Impurity (2-2) (%) | Impurity (2-3) (%) | Efficiency (relative value) | Durability (relative value) | Remarks |
|---|---|---|---|---|---|---|---|---|
| Device 5-1 | Sublimated 5 | 100.000 | 0.000 | 0.000 | 0.000 | 10 | 10 | Inventive |
| Device 5-2 | Sublimated 4 | 99.999 | 0.001 | 0.000 | 0.000 | 10 | 10 | Inventive |
| Device 5-3 | Sublimated 3 | 99.982 | 0.018 | 0.000 | 0.000 | 10 | 10 | Inventive |
| Device 5-4 | Sublimated 2 | 99.91 | 0.09 | 0.00 | 0.00 | 10 | 10 | Inventive |
| Comparative device 5-1 | Sublimated 1 | 99.59 | 0.41 | 0.00 | 0.00 | 10 | 6 | Comparative |
| Device 5-5 | Crude 4 | 99.997 | 0.003 | 0.000 | 0.000 | 10 | 10 | Inventive |
| Comparative device 5-2 | Crude 3 | 99.87 | 0.13 | 0.00 | 0.00 | 10 | 8 | Comparative |
| Comparative device 5-3 | Crude 2 | 98.57 | 1.43 | 0.00 | 0.00 | 9 | <1 | Comparative |
| Comparative device 5-4 | Crude 1 | 97.35 | 2.20 | 0.45 | 0.00 | 7 | <1 | Comparative |
| Device 5-6 | Comparative 1 | 99.456 | 0.000 | 0.544 | 0.000 | 10 | 10 | Inventive |
| Device 5-7 | Comparative 2 | 99.561 | 0.000 | 0.000 | 0.439 | 10 | 10 | Inventive |

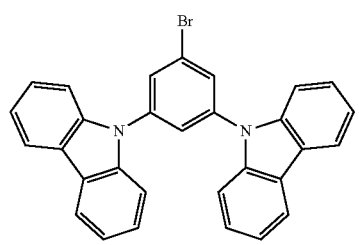

(2-1)

TABLE 5-continued

| Device No. | Compound (2) | Purity (%) | Impurity (2-1) (%) | Impurity (2-2) (%) | Impurity (2-3) (%) | Efficiency (relative value) | Durability (relative value) | Remarks |
|---|---|---|---|---|---|---|---|---|

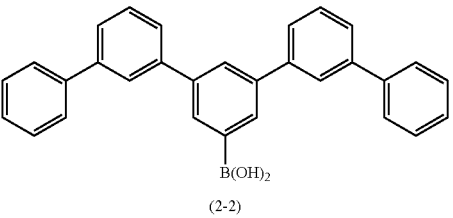 [SMILES: OB(O)c1cc(-c2cccc(-c3ccccc3)c2)cc(-c2cccc(-c3ccccc3)c2)c1]

(2-2)

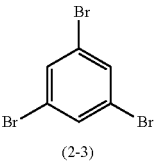

(2-3)

Example 4

Devices were fabricated in the same manner as the procedure of Example 2-1 for the fabrication of the device 1-1, except that the compound (9) was used as a host material instead of the compound (1). The results of evaluations of the devices, together with the purities (%) of the compound (9) and the contents of the impurities (%) as a result of the respective purification methods, are shown in Table 6. No impurities other than the impurities (9-1), (9-2) and (9-3) shown in Table 6 were detected by HPLC. The structures of the impurities (9-1), (9-2) and (9-3) are shown below. The efficiency and durability results of the devices were expressed as relative values to those of the device using "Sublimated 5" each set as 10.

TABLE 6

| Device No. | Compound (9) | Purity (%) | Impurity (9-1) (%) | Impurity (9-2) (%) | Impurity (9-3) (%) | Efficiency (relative value) | Durability (relative value) | Remarks |
|---|---|---|---|---|---|---|---|---|
| Device 6-1 | Sublimated 5 | 100.000 | 0.000 | 0.000 | 0.000 | 10 | 10 | Inventive |
| Device 6-2 | Sublimated 4 | 99.948 | 0.052 | 0.000 | 0.000 | 10 | 10 | Inventive |
| Comparative device 6-1 | Sublimated 3 | 99.89 | 0.11 | 0.00 | 0.00 | 10 | 8 | Comparative |
| Comparative device 6-2 | Sublimated 2 | 99.76 | 0.24 | 0.00 | 0.00 | 10 | 5 | Comparative |
| Comparative device 6-3 | Sublimated 1 | 99.47 | 0.53 | 0.00 | 0.00 | 10 | 3 | Comparative |
| Comparative device 6-4 | Crude 4 | 99.87 | 0.13 | 0.00 | 0.00 | 10 | 7 | Comparative |
| Comparative device 6-5 | Crude 3 | 99.75 | 0.25 | 0.00 | 0.00 | 10 | 5 | Comparative |
| Comparative device 6-6 | Crude 2 | 99.17 | 0.83 | 0.00 | 0.00 | 9 | 1 | Comparative |
| Comparative device 6-7 | Crude 1 | 98.24 | 1.51 | 0.25 | 0.00 | 7 | <1 | Comparative |
| Device 6-3 | Comparative 1 | 99.377 | 0.000 | 0.623 | 0.000 | 10 | 10 | Inventive |
| Device 6-4 | Comparative 2 | 99.423 | 0.000 | 0.000 | 0.577 | 10 | 10 | Inventive |

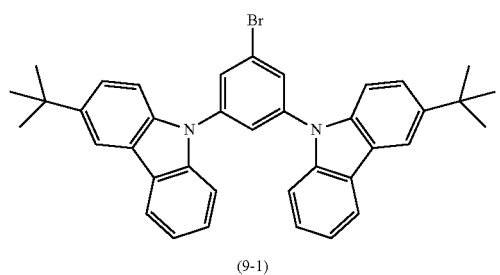 [SMILES: CC(C)(C)c1ccc2c(c1)c1ccccc1n2-c1cc(Br)cc(-n2c3ccccc3c3cc(C(C)(C)C)ccc32)c1]

(9-1)

TABLE 6-continued

| Device No. | Compound (9) | Purity (%) | Impurity (9-1) (%) | Impurity (9-2) (%) | Impurity (9-3) (%) | Efficiency (relative value) | Durability (relative value) | Remarks |
|---|---|---|---|---|---|---|---|---|

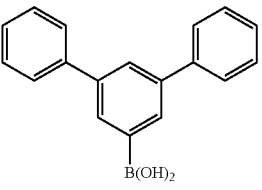

(9-2)

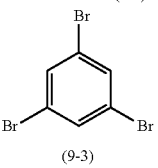

(9-3)

Example 5

Devices were fabricated in the same manner as the procedure of Example 2-1 for the fabrication of the device 1-1, except that the compound (11) was used as a host material instead of the compound (1). The results of evaluations of the devices, together with the purities (%) of the compound (11) and the contents of the impurities (%) as a result of the respective purification methods, are shown in Table 7. No impurities other than the impurities (11-1), (11-2) and (11-3) shown in Table 7 were detected by HPLC. The structures of the impurities (11-1), (11-2) and (11-3) are shown below. The efficiency and durability results of the devices were expressed as relative values to those of the device using "Sublimated 5" each set as 10.

TABLE 7

| Device No. | Compound (11) | Purity (%) | Impurity (11-1) (%) | Impurity (11-2) (%) | Impurity (11-3) (%) | Efficiency (relative value) | Durability (relative value) | Remarks |
|---|---|---|---|---|---|---|---|---|
| Device 7-1 | Sublimated 5 | 100.000 | 0.000 | 0.000 | 0.000 | 10 | 10 | Inventive |
| Device 7-2 | Sublimated 4 | 99.998 | 0.002 | 0.000 | 0.000 | 10 | 10 | Inventive |
| Device 7-3 | Sublimated 3 | 99.996 | 0.004 | 0.000 | 0.000 | 10 | 10 | Inventive |
| Comparative device 7-1 | Sublimated 2 | 99.88 | 0.12 | 0.00 | 0.00 | 10 | 8 | Comparative |
| Comparative device 7-2 | Sublimated 1 | 99.75 | 0.25 | 0.00 | 0.00 | 10 | 7 | Comparative |
| Device 7-4 | Crude 4 | 99.980 | 0.020 | 0.000 | 0.000 | 10 | 10 | Inventive |
| Device 7-5 | Crude 3 | 99.93 | 0.07 | 0.00 | 0.00 | 10 | 10 | Inventive |
| Comparative device 7-3 | Crude 2 | 99.21 | 0.79 | 0.00 | 0.00 | 10 | 2 | Comparative |
| Comparative device 7-4 | Crude 1 | 98.43 | 1.23 | 0.34 | 0.00 | 9 | 1 | Comparative |
| Device 7-6 | Comparative 1 | 99.480 | 0.000 | 0.520 | 0.000 | 10 | 10 | Inventive |
| Device 7-7 | Comparative 2 | 99.526 | 0.000 | 0.000 | 0.474 | 10 | 10 | Inventive |

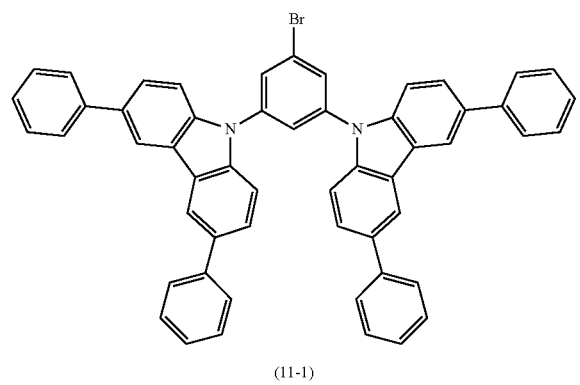 [SMILES: Brc1cc(-n2c3ccc(-c4ccccc4)cc3c3cc(-c4ccccc4)ccc32)cc(-n2c3ccc(-c4ccccc4)cc3c3cc(-c4ccccc4)ccc32)c1]

(11-1)

TABLE 7-continued

| Device No. | Compound (11) | Purity (%) | Impurity (11-1) (%) | Impurity (11-2) (%) | Impurity (11-3) (%) | Efficiency (relative value) | Durability (relative value) | Remarks |
|---|---|---|---|---|---|---|---|---|

(11-2)

(11-3)

Example 6

Devices were fabricated in the same manner as the procedure of Example 2-1 for the fabrication of the device 1-1, except that the compound (13) was used as a host material instead of the compound (1). The results of evaluations of the devices, together with the purities (%) of the compound (13) and the contents of the impurities (%) as a result of the respective purification methods, are shown in Table 8. No impurities other than the impurities (13-1), (13-2) and (13-3) shown in Table 8 were detected by HPLC. The structures of the impurities (13-1), (13-2) and (13-3) are shown below. The efficiency and durability results of the devices were expressed as relative values to those of the device using "Sublimated 5" each set as 10.

TABLE 8

| Device No. | Compound (13) | Purity (%) | Impurity (13-1) (%) | Impurity (13-2) (%) | Impurity (13-3) (%) | Efficiency (relative value) | Durability (relative value) | Remarks |
|---|---|---|---|---|---|---|---|---|
| Device 8-1 | Sublimated 5 | 99.999 | 0.001 | 0.000 | 0.000 | 10 | 10 | Inventive |
| Device 8-2 | Sublimated 4 | 99.978 | 0.022 | 0.000 | 0.000 | 10 | 10 | Inventive |
| Device 8-3 | Sublimated 3 | 99.92 | 0.08 | 0.00 | 0.00 | 10 | 10 | Inventive |
| Comparative device 8-1 | Sublimated 2 | 99.88 | 0.12 | 0.00 | 0.00 | 10 | 8 | Comparative |
| Comparative device 8-2 | Sublimated 1 | 99.67 | 0.33 | 0.00 | 0.00 | 10 | 6 | Comparative |
| Comparative device 8-3 | Crude 4 | 99.85 | 0.15 | 0.00 | 0.00 | 10 | 7 | Comparative |
| Comparative device 8-4 | Crude 3 | 99.78 | 0.22 | 0.00 | 0.00 | 10 | 6 | Comparative |
| Comparative device 8-5 | Crude 2 | 99.50 | 0.50 | 0.00 | 0.00 | 9 | 3 | Comparative |
| Comparative device 8-6 | Crude 1 | 97.81 | 1.88 | 0.31 | 0.00 | 9 | <1 | Comparative |
| Device 8-4 | Comparative 1 | 99.393 | 0.001 | 0.606 | 0.000 | 10 | 10 | Inventive |
| Device 8-5 | Comparative 2 | 99.428 | 0.001 | 0.000 | 0.571 | 10 | 10 | Inventive |

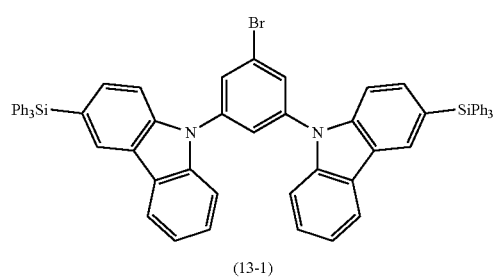

(13-1)

TABLE 8-continued

| Device No. | Compound (13) | Purity (%) | Impurity (13-1) (%) | Impurity (13-2) (%) | Impurity (13-3) (%) | Efficiency (relative value) | Durability (relative value) | Remarks |
|---|---|---|---|---|---|---|---|---|

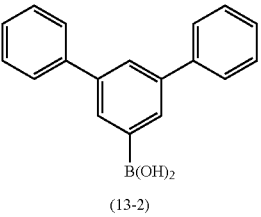 [SMILES: OB(O)c1cc(-c2ccccc2)cc(-c2ccccc2)c1]

(13-2)

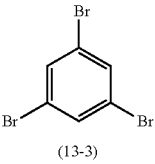

(13-3)

Example 7

Devices were fabricated in the same manner as the procedure of Example 2-1 for the fabrication of the device 1-1, except that the compound (20) was used as a host material instead of the compound (1). The results of evaluations of the devices, together with the purities (%) of the compound (20) and the contents of the impurities (%) as a result of the respective purification methods, are shown in Table 9. No impurities other than the impurities (20-1), (20-2) and (20-3) shown in Table 9 were detected by HPLC. The structures of the impurities (20-1), (20-2) and (20-3) are shown below. The efficiency and durability results of the devices were expressed as relative values to those of the device using "Sublimated 4" each set as 10.

TABLE 9

| Device No. | Compound (20) | Purity (%) | Impurity (20-1) (%) | Impurity (20-2) (%) | Impurity (20-3) (%) | Efficiency (relative value) | Durability (relative value) | Remarks |
|---|---|---|---|---|---|---|---|---|
| Device 9-1 | Sublimated 4 | 100.000 | 0.000 | 0.000 | 0.000 | 10 | 10 | Inventive |
| Device 9-2 | Sublimated 3 | 99.999 | 0.001 | 0.000 | 0.000 | 10 | 10 | Inventive |
| Device 9-3 | Sublimated 2 | 99.92 | 0.08 | 0.00 | 0.00 | 10 | 10 | Inventive |
| Comparative device 9-1 | Sublimated 1 | 99.88 | 0.12 | 0.00 | 0.00 | 10 | 8 | Comparative |
| Comparative device 9-2 | Crude 3 | 99.83 | 0.17 | 0.00 | 0.00 | 10 | 7 | Comparative |
| Comparative device 9-3 | Crude 2 | 99.45 | 0.55 | 0.00 | 0.00 | 10 | 4 | Comparative |
| Comparative device 9-4 | Crude 1 | 99.08 | 0.72 | 0.20 | 0.00 | 9 | 3 | Comparative (Synthesis purification method described in WO2004/074399) |
| Device 9-4 | Comparative 1 | 99.421 | 0.000 | 0.579 | 0.000 | 10 | 10 | Inventive |
| Device 9-5 | Comparative 2 | 99.487 | 0.000 | 0.000 | 0.513 | 10 | 10 | Inventive |

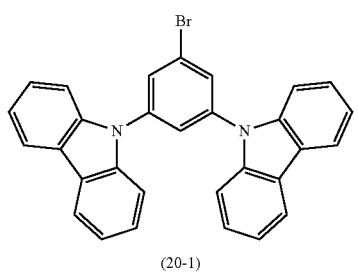 [SMILES: Brc1cc(-n2c3ccccc3c3ccccc32)cc(-n2c3ccccc3c3ccccc32)c1]

(20-1)

TABLE 9-continued

| Device No. | Compound (20) | Purity (%) | Impurity (20-1) (%) | Impurity (20-2) (%) | Impurity (20-3) (%) | Efficiency (relative value) | Durability (relative value) | Remarks |
|---|---|---|---|---|---|---|---|---|

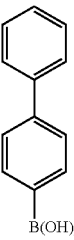

(20-2)

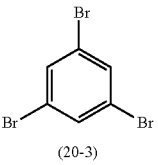

(20-3)

Example 8

Devices were fabricated in the same manner as the procedure of Example 2-1 for the fabrication of the device 1-1, except that the compound (25) was used as a host material instead of the compound (1). The results of evaluations of the devices, together with the purities (%) of the compound (25) and the contents of the impurities (%) as a result of the respective purification methods, are shown in Table 10. No impurities other than the impurities (25-1), (25-2) and (25-3) shown in Table 10 were detected by HPLC. The structures of the impurities (25-1), (25-2) and (25-3) are shown below. The efficiency and durability results of the devices were expressed as relative values to those of the device using "Sublimated 4" each set as 10.

TABLE 10

| Device No. | Compound (25) | Purity (%) | Impurity (25-1) (%) | Impurity (25-2) (%) | Impurity (25-3) (%) | Efficiency (relative value) | Durability (relative value) | Remarks |
|---|---|---|---|---|---|---|---|---|
| Device 10-1 | Sublimated 4 | 100.000 | 0.000 | 0.000 | 0.000 | 10 | 10 | Inventive |
| Device 10-2 | Sublimated 3 | 99.968 | 0.032 | 0.000 | 0.000 | 10 | 10 | Inventive |
| Comparative device 10-1 | Sublimated 2 | 99.88 | 0.12 | 0.00 | 0.00 | 10 | 8 | Comparative |
| Comparative device 10-2 | Sublimated 1 | 99.81 | 0.19 | 0.00 | 0.00 | 10 | 7 | Comparative |
| Device 10-3 | Crude 3 | 99.91 | 0.09 | 0.00 | 0.00 | 10 | 10 | Inventive |
| Comparative device 10-3 | Crude 2 | 99.62 | 0.38 | 0.00 | 0.00 | 10 | 6 | Comparative |
| Comparative device 10-4 | Crude 1 | 99.40 | 0.49 | 0.11 | 0.00 | 10 | 5 | Comparative (Synthesis purification method described in WO2004/074399) |
| Device 10-4 | Comparative 1 | 99.339 | 0.000 | 0.661 | 0.000 | 10 | 10 | Inventive |
| Device 10-5 | Comparative 2 | 99.381 | 0.000 | 0.000 | 0.619 | 10 | 10 | Inventive |

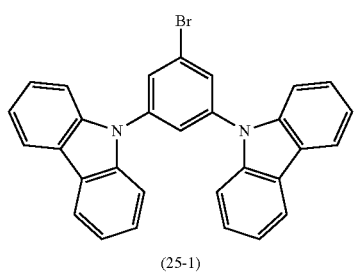 [SMILES: Brc1cc(-n2c3ccccc3c3ccccc32)cc(-n2c3ccccc3c3ccccc32)c1]

(25-1)

TABLE 10-continued

| Device No. | Compound (25) | Purity (%) | Impurity (25-1) (%) | Impurity (25-2) (%) | Impurity (25-3) (%) | Efficiency (relative value) | Durability (relative value) | Remarks |
|---|---|---|---|---|---|---|---|---|

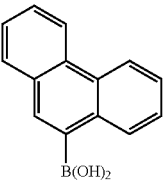

(25-2)

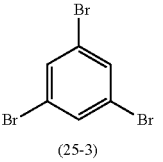

(25-3)

As seen from Tables 5 to 10, the similar results as the results in Table 1 were obtained even when the compound (1) was changed to the exemplified compounds.

Example 9

Example 9-1

A glass substrate with 0.5 mm thickness and 2.5 cm square having an ITO film (Geomatec, surface resistivity=10 Ω/sq.) was cleaned in 2-propanol in a cleaning container by sonication, followed by UV ozone treatment for 30 min. An aqueous solution of PEDOT (poly(3,4-ethylenedioxythiophene))/PSS (polystyrene sulfonic acid) (BaytronP (standard grade)) was spin coated (4000 rpm, 60 sec) on the ITO film as a transparent anode and dried at 120° C. for 10 min to form a hole transporting layer (150 nm thick).

Subsequently, a solution of 1 mass % of the compound (1) and 0.05 mass % of GD-1 in toluene was spin coated (2000 rpm, 60 sec) on the hole transporting layer to form a light emitting layer (50 nm thick).

BAlq was deposited to a thickness of 50 nm on the light emitting layer by vacuum deposition to form an electron transporting layer Lithium fluoride and aluminum were sequentially deposited to thicknesses of 0.1 nm and 100 nm, respectively, on the electron transporting layer to form a cathode.

The resulting structure was placed in a glove box purged with nitrogen gas without being exposed to the atmosphere and encapsulated with a glass encapsulation can and a UV curable adhesive (XNR5516HV, Nagase Ciba Co., Ltd.) to fabricate organic electroluminescence devices 11-1 and 11-2 and Comparative Devices 11-1 and 11-2. The efficiency and durability results of the devices were expressed as relative values to those of the device using "Sublimated 5" each set as 10.

TABLE 11

| Device No. | Compound (1) | Efficiency (relative value) | Durability (relative value) | Remarks |
|---|---|---|---|---|
| Device 11-1 | Sublimated 5 | 10 | 10 | Inventive |
| Device 11-2 | Crude 4 | 10 | 10 | Inventive |

TABLE 11-continued

| Device No. | Compound (1) | Efficiency (relative value) | Durability (relative value) | Remarks |
|---|---|---|---|---|
| Comparative device 11-1 | Sublimated 2 | 9 | 7 | Comparative |
| Comparative device 11-2 | Sublimated 1 | 9 | 5 | Comparative (Synthesis purification method described in WO2004/074399) |

Example 9-2

Devices were fabricated in the same manner as the procedure of Example 9-1 for the fabrication of the device 11-1, except that the compound (9) was used instead of the compound (1). The results of evaluations of the devices are shown in Table 12. The efficiency and durability results of the devices were expressed as relative values to those of the device using "Sublimated 5" each set as 10.

TABLE 12

| Device No. | Compound (9) | Efficiency (relative value) | Durability (relative value) | Remarks |
|---|---|---|---|---|
| Device 12-1 | Sublimated 5 | 10 | 10 | Inventive |
| Device 12-2 | Sublimated 4 | 10 | 10 | Inventive |
| Comparative device 12-1 | Sublimated 2 | 10 | 8 | Comparative |
| Comparative device 12-2 | Sublimated 1 | 10 | 5 | Comparative |

Example 9-3

Devices were fabricated in the same manner as the procedure of Example 9-1 for the fabrication of the device 11-1, except that the compound (11) was used instead of the compound (1). The results of evaluations of the devices are shown in Table 13. The efficiency and durability results of the devices were expressed as relative values to those of the device using "Sublimated 5" each set as 10.

TABLE 13

| Device No. | Compound (11) | Efficiency (relative value) | Durability (relative value) | Remarks |
|---|---|---|---|---|
| Device 13-1 | Sublimated 5 | 10 | 10 | Inventive |
| Comparative device 13-1 | Sublimated 1 | 10 | 8 | Comparative |
| Device 13-2 | Crude 3 | 10 | 10 | Inventive |
| Comparative device 13-2 | Crude 2 | 9 | 5 | Comparative |

Example 9-4

Devices were fabricated in the same manner as the procedure of Example 9-1 for the fabrication of the device 11-1, except that the compound (13) was used instead of the compound (1). The results of evaluations of the devices are shown in Table 14. The efficiency and durability results of the devices were expressed as relative values to those of the device using "Sublimated 5" each set as 10.

TABLE 14

| Device No. | Compound (13) | Efficiency (relative value) | Durability (relative value) | Remarks |
|---|---|---|---|---|
| Device 14-1 | Sublimated 5 | 10 | 10 | Inventive |
| Device 14-2 | Sublimated 3 | 10 | 10 | Inventive |
| Comparative device 14-1 | Crude 3 | 10 | 8 | Comparative |
| Comparative device 14-2 | Crude 2 | 9 | 5 | Comparative |

As can be seen from the results in Tables 11-14, the inventive devices could be manufactured with good performance even when the light emitting layers were formed by a solution coating method.

In pixels of light emission apparatuses, display apparatuses and illumination apparatuses, instantaneous light emission with high luminance intensity through high current density is needed. In response to this need, the luminescence device of the present invention is designed to have high luminous efficiency. Therefore, the luminescence device of the present invention can be advantageously used in the apparatuses.

In addition, the device of the present invention has high luminous efficiency and good durability even in high-temperature environments, such as on-board apparatuses. Therefore, the device of the present invention is suitable for use in light emission apparatuses, display apparatuses and illumination apparatuses.

The structures of the compounds used in Examples 2-1 to 9-4 are as follows.

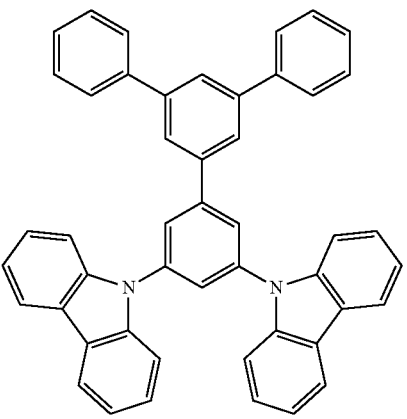

(1)

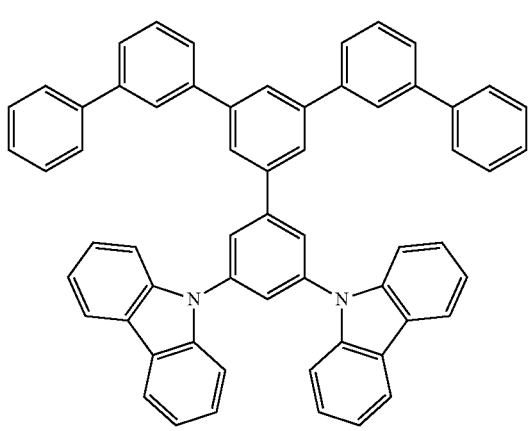

(2)

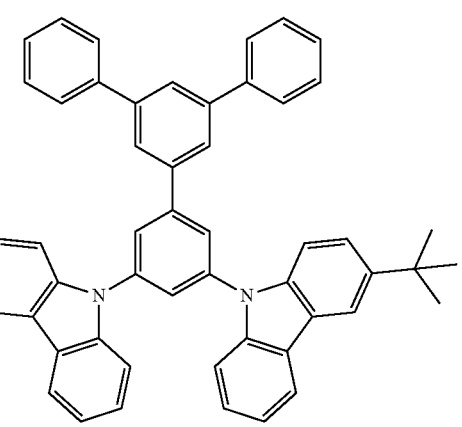

(9)

(11)
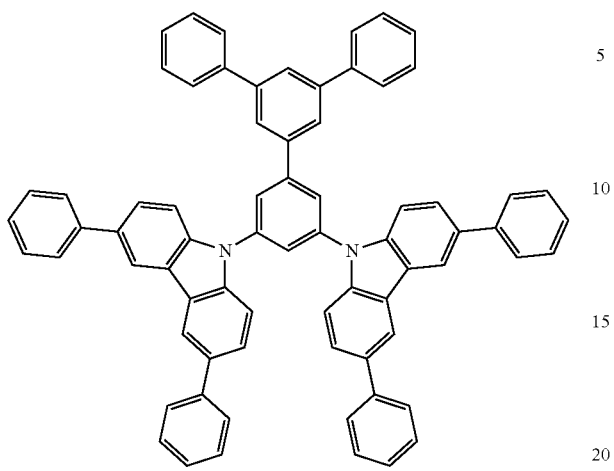
(13)
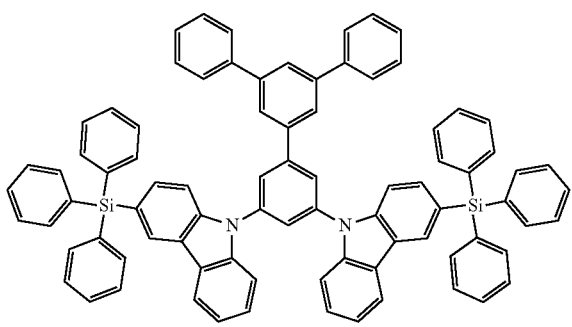
(20)
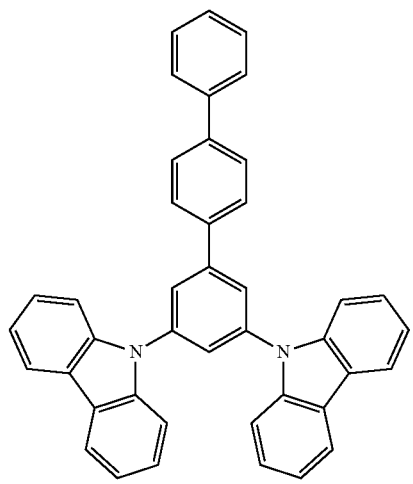
(25)
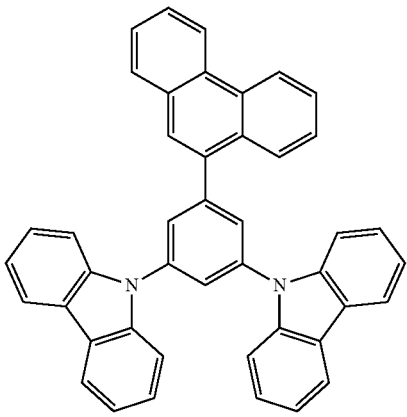
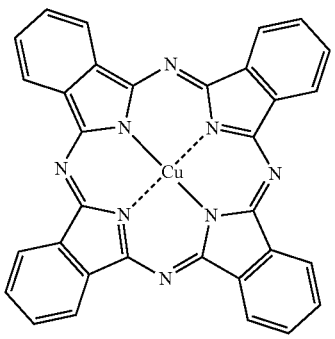
CuPc
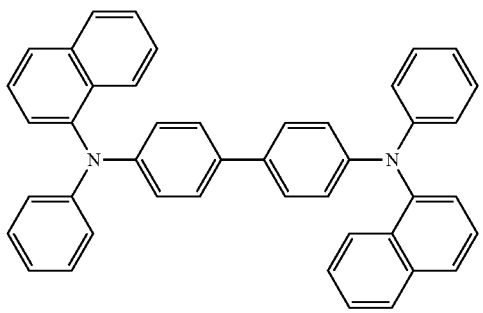
NPD
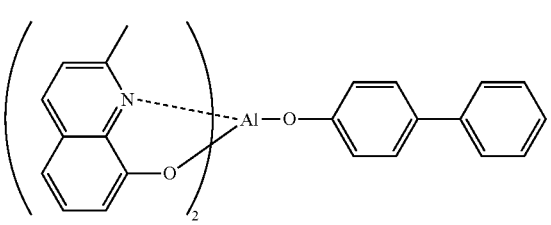
BAlq
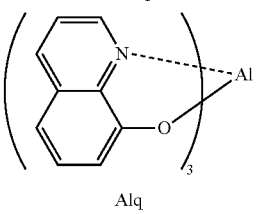
Alq

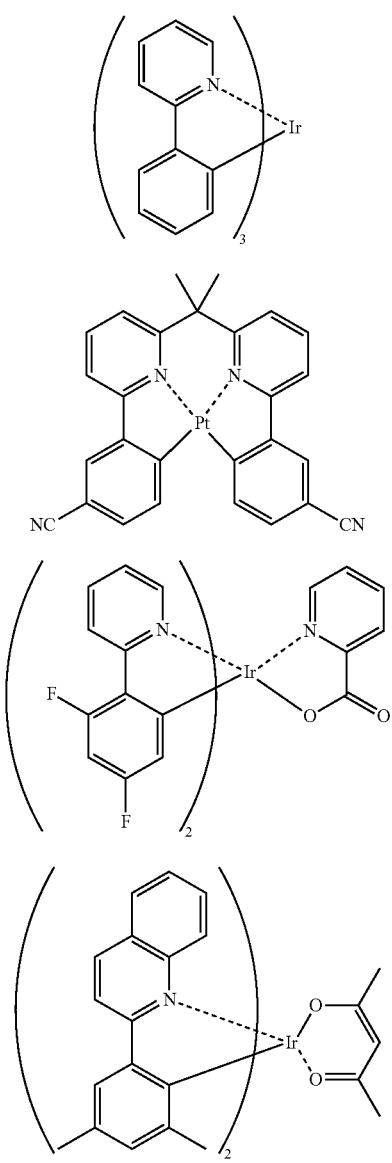

INDUSTRIAL APPLICABILITY

According to the present invention, an organic electroluminescence device with high luminous efficiency and good durability can be provided.

While the present invention has been described in detail and with reference to specific embodiments thereof, it will be apparent to one skilled in the art that various changes and modifications can be made therein without departing from the spirit and scope thereof.

This application is based on Japanese Patent Application Nos. 2010-007535 filed on Jan. 15, 2010, 2010-116666 filed on May 20, 2010 and 2010-247908 filed on Nov. 4, 2010, the entire contents of which are incorporated hereinto by reference.

EXPLANATION OF REFERENCE NUMERALS AND SYMBOLS

2: Substrate
3: Anode
4: Hole injection layer
5: Hole transporting layer
6: Light emitting layer
7: Hole blocking layer
8: Electron transporting layer
9: Cathode
10: Organic electroluminescence device (organic EL device)
11: Organic layer
12: Protective layer
14: Adhesive layer
16: Sealing container
20: Light emission apparatus
30: Light scattering member
30A: Light incident plane
30B: Light exit plane
31: Transparent substrate
32: Fine particles
40: Illumination apparatus

The invention claimed is:

1. A charge transporting material, comprising:
a compound represented by Formula (Cz-1),
wherein a content of an impurity represented by Formula (I-1) in the charge transporting material is from 0.000% to 0.10% when the content is calculated as a proportion of an absorption intensity area of the impurity represented by Formula (I-1) with respect to a total absorption intensity area of the charge transporting material, as measured by high-performance liquid chromatography at a measurement wavelength of 254 nm:

Formula (Cz-1)

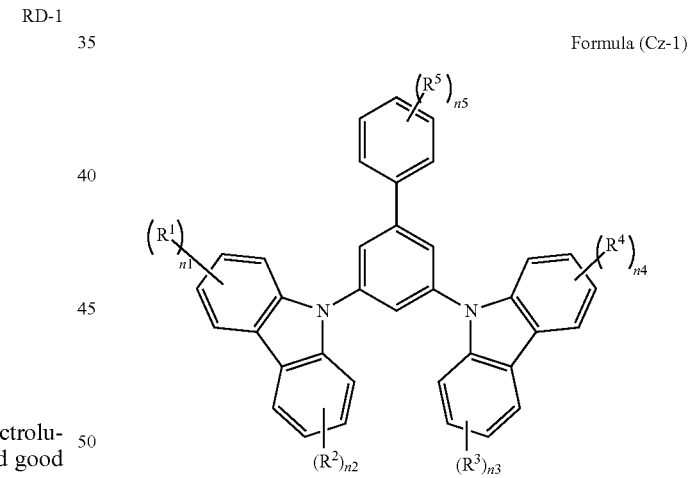

wherein in Formula (Cz-1), each of $R^1$ to $R^4$ independently represents a fluorine atom, an alkyl group, an aryl group, a silyl group or a cyano group, provided that when $R^1$ to $R^4$ respectively exist in plurality, a plurality of $R^1$'s to a plurality of $R^4$'s may be the same or different respectively;

$R^5$ represents an alkyl group, an aryl group or a silyl group, provided that $R^5$ does not represent a carbazolyl group or a perfluoroalkyl group, and when $R^5$ exists in plurality, a plurality of $R^5$'s may be the same or different or a plurality of $R^5$'s may be bonded together to form an aryl ring;

each of n1 to n4 independently represents an integer from 0 to 4; and n5 represents an integer from 0 to 5:

Formula (I-1)

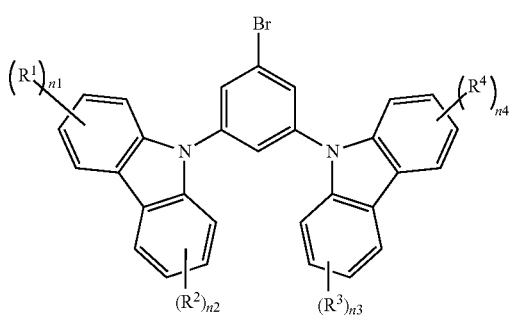

wherein in Formula (I-1), $R^1$ to $R^4$ are the same atoms or groups as defined for $R^1$ to $R^4$ in Formula (Cz-1) respectively; and n1 to n4 are the same integers as defined for n1 to n4 in Formula (Cz-1) respectively.

2. The charge transporting material according to claim 1, wherein a proportion of a sum of absorption intensity areas of the compound represented by Formula (Cz-1), the impurity represented by Formula (I-1), an impurity represented by Formula (II-1) and 1,3,5-tribromobenzene with respect to the total absorption intensity area of the charge transporting material, as measured by high-performance liquid chromatography at a measurement wavelength of 254 nm, is 100%:

Formula (II-1)

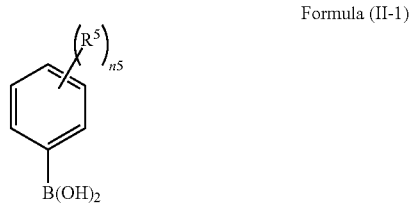

wherein in Formula (II-1), $R^5$ is the same group as defined for $R^5$ in Formula (Cz-1); and n5 is the same integer as defined for n5 in Formula (Cz-1).

3. The charge transporting material according to claim 1, wherein the compound represented by Formula (Cz-1) is represented by Formula (Cz-2) and the impurity represented by Formula (I-1) is represented by Formula (I-2):

Formula (Cz-2)

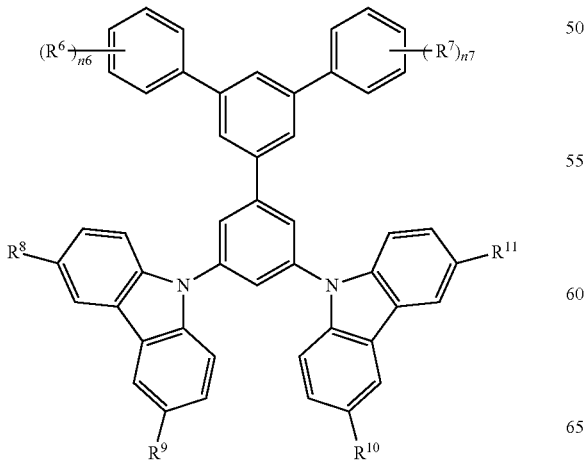

wherein in Formula (Cz-2), each of $R^8$ to $R^{11}$ independently represents a hydrogen atom, a fluorine atom, an alkyl group, an aryl group, a silyl group or a cyano group;

each of $R^6$ and $R^7$ independently represents an alkyl group, an aryl group, a cyano group or a fluorine atom, provided that when $R^6$ and $R^7$ respectively exist in plurality, a plurality of $R^6$'s and a plurality of $R^7$'s may be the same or different respectively or a plurality of $R^6$'s and a plurality of $R^7$'s may be bonded together to form an aryl ring that may have an alkyl group respectively; and each of n6 and n7 independently represents an integer from 0 to 5:

Formula (I-2)

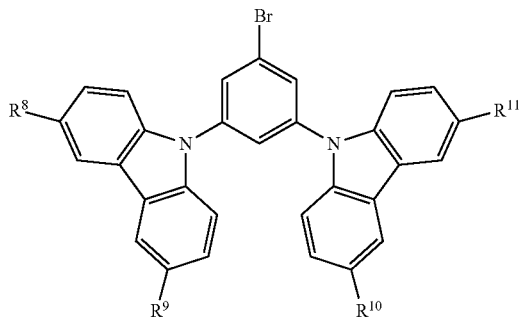

wherein in Formula (I-2), $R^8$ to $R^{11}$ are the same atoms or groups as defined for $R^8$ to $R^{11}$ in Formula (Cz-2) respectively.

4. The charge transporting material according to claim 3, wherein a proportion of a sum of absorption intensity areas of the compound represented by Formula (Cz-2), the impurity represented by Formula (I-2), an impurity represented by Formula (II-2) and 1,3,5-tribromobenzene with respect to the total absorption intensity area of the charge transporting material, as measured by high-performance liquid chromatography at a measurement wavelength of 254 nm, is 100%:

Formula (II-2)

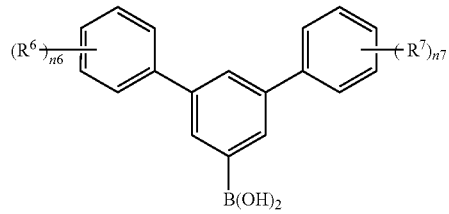

wherein in Formula (II-2), $R^6$ and $R^7$ are the same atoms or groups as defined for $R^6$ and $R^7$ in Formula (Cz-2) respectively; and n6 and n7 are the same integers as defined for n6 and n7 in Formula (Cz-2) respectively.

5. The charge transporting material according to claim 3, wherein in Formula (Cz-2), $R^6$ and $R^7$ represent phenyl groups and each of n6 and n7 independently represents 0 or 1, and in Formulae (Cz-2) and (I-2), each of $R^8$ to $R^{11}$ independently represents a hydrogen atom, a t-butyl group, a phenyl group, a trimethylsilyl group or a triphenylsilyl group.

6. A composition, comprising:
the charge transporting material according to claim 1.

7. A thin film, comprising:
the charge transporting material according to claim 1.

8. An organic electroluminescence device, comprising on a substrate:
- a pair of electrodes; and
- at least one layer of an organic layer including a light emitting layer between the electrodes,
- wherein any layer of the at least one layer of an organic layer contains the charge transporting material according to claim 1.

9. The organic electroluminescence device according to claim 8,
wherein the light emitting layer contains the charge transporting material.

10. The organic electroluminescence device according to claim 8,
wherein at least one layer of the organic layer between the pair of electrodes is formed by a solution Coating method.

11. A light emission apparatus using the organic electroluminescence device according to claim 8.

12. A display apparatus using the organic electroluminescence device according to claim 8.

13. An illumination apparatus using the organic electroluminescence device according to claim 8.

14. The charge transporting material according to claim 1,
wherein the content of the impurity represented by Formula (I-1) in the charge transporting material is from greater than 0.000% to 0.10%.

15. The charge transporting material according to claim 14,
wherein the content of the impurity represented by Formula (I-1) in the charge transporting material is from 0.001% to 0.10%.

* * * * *